(12) United States Patent
Goehring et al.

(10) Patent No.: US 9,045,435 B2
(45) Date of Patent: Jun. 2, 2015

(54) QUINAZOLINE COMPOUNDS AS SODIUM CHANNEL BLOCKERS

(75) Inventors: R. Richard Goehring, Yardley, PA (US); Laykea Tafesse, Robbinsville, NJ (US); Jiangchao Yao, Princeton, NJ (US)

(73) Assignee: Purdue Pharma, L.P., Stamford, CT (US)

( * ) Notice: Subject to any disclaimer, the term of this patent is extended or adjusted under 35 U.S.C. 154(b) by 60 days.

(21) Appl. No.: 13/878,004

(22) PCT Filed: Oct. 5, 2011

(86) PCT No.: PCT/IB2011/002362
§ 371 (c)(1),
(2), (4) Date: Jun. 24, 2013

(87) PCT Pub. No.: WO2012/046132
PCT Pub. Date: Apr. 12, 2012

(65) Prior Publication Data
US 2013/0289044 A1 Oct. 31, 2013

Related U.S. Application Data

(60) Provisional application No. 61/390,084, filed on Oct. 5, 2010.

(51) Int. Cl.
C07D 239/74 (2006.01)
C07D 239/84 (2006.01)
A01N 43/54 (2006.01)
A61K 31/517 (2006.01)
C07D 401/04 (2006.01)
C07D 401/12 (2006.01)
C07D 403/04 (2006.01)
C07D 403/12 (2006.01)
C07D 471/08 (2006.01)

(52) U.S. Cl.
CPC ............ *C07D 239/74* (2013.01); *C07D 239/84* (2013.01); *C07D 401/04* (2013.01); *C07D 401/12* (2013.01); *C07D 403/04* (2013.01); *C07D 403/12* (2013.01); *C07D 471/08* (2013.01)

(58) Field of Classification Search
CPC ..... C07D 239/74; C07D 239/84; A01N 43/54
USPC ....................................... 514/266.1; 544/284
See application file for complete search history.

(56) References Cited

U.S. PATENT DOCUMENTS

| | | | |
|---|---|---|---|
| 5,948,782 A | 9/1999 | Sohda et al. | |
| 6,136,839 A | 10/2000 | Isakson et al. | |
| 6,352,989 B1 | 3/2002 | Miyazaki et al. | |
| 6,800,644 B2 | 10/2004 | Miyazaki et al. | |
| 2006/0154935 A1 | 7/2006 | Wilson et al. | |
| 2006/0154962 A1 | 7/2006 | Yang | |
| 2009/0062539 A1 | 3/2009 | Yamamoto et al. | |
| 2010/0145046 A1 | 6/2010 | Coates et al. | |

FOREIGN PATENT DOCUMENTS

| | | |
|---|---|---|
| EP | 1 764 235 A1 | 3/2007 |
| EP | 2 105 480 A1 | 9/2009 |
| FR | 2 940 309 A1 | 6/2010 |
| JP | 2-52360 A | 2/1990 |
| WO | WO 01/68612 A2 | 9/2001 |
| WO | WO 02/076976 A2 | 10/2002 |
| WO | WO 03/029359 A1 | 4/2003 |
| WO | WO 2004/078733 A1 | 9/2004 |
| WO | WO 2005/118575 A1 | 12/2005 |
| WO | WO 2006/028904 A1 | 3/2006 |
| WO | WO 2006/108689 A2 | 10/2006 |
| WO | WO 2006/108693 A2 | 10/2006 |
| WO | WO 2006/136617 A2 | 12/2006 |
| WO | WO 2007/039528 A1 | 4/2007 |
| WO | WO 2007/058989 A2 | 5/2007 |
| WO | WO 2007/098169 A1 | 8/2007 |
| WO | WO 2007/103456 A2 | 9/2007 |
| WO | WO 2008/012326 A1 | 1/2008 |
| WO | WO 2008/021891 A2 | 2/2008 |

(Continued)

OTHER PUBLICATIONS

Vippagunta et al. (2001).*
Banker et al (1997).*
Wolff et al (1997).*
Anger, T., et al., "Medicinal chemistry of neuronal voltage-gated sodium channel blockers," *J. Med. Chem* 44(2):115-137, American Chemical Society, United States (2001).
Baker, M.D. and Wood, J.N., "Involvement of Na+ channels in pain pathways," *Trends Pharmacol. Sci.* 22(1):27-31, Elsevier, England (2001).
Barthó, L., et al., "Involvement of capsaicin-sensitive neurones in hyperalgesia and enhanced opioid antinociception in inflammation," *Naunyn-Schmiedebergs Arch. Pharmacol.* 342(6):666-670, Springer-Verlag, Germany (1990).
Benjamin, E.R., et al., "Validation of a fluorescent imaging plate reader membrane potential assay for high-throughput screening of glycine transporter modulators," *J. Biomol. Screen.* 10(4):365-372, Sage Publications, United States (2005).

(Continued)

*Primary Examiner* — Paul V. Ward
(74) *Attorney, Agent, or Firm* — Purdue Pharma L.P.; Alan L. Koller; Weiying Yang

(57) ABSTRACT

The invention relates to aryl substituted quinazolines of Formula I, and pharmaceutically acceptable salts, prodrugs, or solvates thereof, wherein G, A, and $R^1$-$R^4$ are defined as set forth in the specification. The invention is also directed to the use of compounds of Formula I to treat a disorder responsive to the blockade of sodium channels. Compounds of the present invention are especially useful for treating pain.

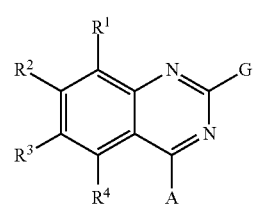

I

50 Claims, No Drawings

(56) References Cited

FOREIGN PATENT DOCUMENTS

| | | |
|---|---|---|
| WO | WO 2008/028689 A1 | 3/2008 |
| WO | WO 2008/028690 A1 | 3/2008 |
| WO | WO 2008/028960 A1 | 3/2008 |
| WO | WO 2009/014637 A2 | 1/2009 |
| WO | WO 2009/020683 A2 | 2/2009 |
| WO | WO 2011/000566 A2 | 1/2011 |
| WO | WO 2012/046132 A1 | 4/2012 |

OTHER PUBLICATIONS

Bingham, A.L., et al., "Over one hundred solvates of sulfathiazole," *Chem. Commun.*: 603-604, The Royal Society of Chemistry, England (2001).

Black, J.A., et al., "Sensory neuron-specific sodium channel SNS is abnormally expressed in the brains of mice with experimental allergic encephalomyelitis and humans with multiple sclerosis," *Proc. Natl. Acad, Sci. USA* 97(21):11598-11602, National Academy of Sciences, United States (2000).

Brower, V., "New paths to pain relief," *Nat. Biotechnol.* 18(4):387-391, Nature America Publishing, United States (2000).

Brown, C.M., et al., "Neuroprotective properties of lifarizine compared with those of other agents in a mouse model of focal cerebral ischaemia," *Br. J. Pharmacol.* 115(8):1425-1432, Stockton Press, England (1995).

Bundgaard, H., "(C) Means to Enhance Penetration: (1) Prodrugs as a means to improve the delivery of peptide drugs," *Adv. Drug Delivery Revs.* 8:1-38, Elsevier Science Publishers, B.V., Netherlands (1992).

Caira, M.R., et al., "Preparation and crystal characterization of a polymorph, a monohydrate, and an ethyl acetate solvate of the antifungal fluconazole," *J. Pharm. Sci.* 93(3):601-611, Wiley-Liss, United States (2004).

Cannon, S.C., "Spectrum of sodium channel disturbances in the nondystrophic myotonias and periodic paralyses," *Kidney Int.* 57(3):772-779, International Society of Nephrology, United States (2000).

Chahine, M., et al., "Voltage-gated sodium channels in neurological disorders," *CNS Neurol. Disord. Drug Targets* 7(2):144-158, Bentham Science Publishers Ltd., United Arab Emirates (2008).

Catterall, W.A., "Common modes of drug action on $Na^+$ channels: local anesthetics, antiarrhythmics and anticonvulsants," *Trends Pharmacol. Sci.* 8:57-65, Elsevier Science Publishers, B.V., Netherlands (1987).

Clare, J.J., et al., "Voltage-gated sodium channels as therapeutic targets," *Drug Discov. Today* 5(11):506-520, Elsevier Science Ltd., England (2000).

Cummins, T.R., et al., "Slow closed-state inactivation: a novel mechanism underlying ramp currents in cells expressing the hNE/PN1 sodium channel," *J. Neurosci.* 18(23):9607-9619, Society for Neuroscience, United States (1998).

Donaldson, I., "Tegretol: a double blind trial in tinnitus," *J. Laryngol. Otol.* 95(9):947-951, Cambridge University Press, England (1981).

Graham, S.H., et al., "Neuroprotective effects of a use-dependent blocker of voltage-dependent sodium channels, BW619C89, in rat middle cerebral artery occlusion," *J. Pharmacol. Exp. Ther.* 269(2):854-859, American Society for Pharmacology and Experimental Therapeutics, United States (1994).

Hanks, J.H. and Wallace, R.E., "17131. Relation of oxygen and temperature in the preservation of tissues by refrigeration," *Proc. Soc. Exp. Biol. Med.* 71(2):196-200, Blackwell Science, United States (1949).

Harootitnian, A.T., et al., "Fluorescence ratio imaging of cytosolic free $Na^+$ in individual fibroblasts and lymphocytes," *J. Biol. Chem.* 264(32):19458-19467, American Society for Biochemistry and Molecular Biology, United States (1989).

Hübner, C.A. and Jentsch, T.J., "Ion channel diseases," *Hum. Mol. Genet.* 11(20):2435-2445, Oxford University Press, England (2002).

Hunskaar, S., et al., "Formalin test in mice, a useful technique for evaluating mild analgesics," *J. Neurosci. Methods* 14(1):69-76, ElsevierScience Publishers B.V., Netherlands (1985).

Ilyin, V.I., et al., "V102862 (Co 102862): a potent, broad-spectrum state-dependent blocker of mammalian voltage-gated sodium channels," *Br. J. Pharmacol.* 144(6):801-812, Nature Publishing Group, England (2005).

Kakeya, N., et al., "Studies on prodrugs of cephalosporins. I. Synthesis and Biological Properties of Glycyloxybenzoyloxymethyl and Glycylaminobenzoyloxymethyl Esters of 7β-[2-(2-aminothiazol-4-yl)-(Z)-2-metfroxyiminoacetamido]-3-methyl-3-cephem-4-carboxylic Acid," *Chem. Parm. Bull. (Tokyo)* 32(2):692-698, Pharmaceutical Society of Japan, Japan (1984).

Kim, H.-L., et al., "Rat brain expresses an alternatively spliced form of the dihydropyridine-sensitive L-type calcium channel α2 subunit," *Proc. Natl. Acad. Sci. USA* 89:3251:3255, National Academy of Sciences, United States (1992).

Kyle, D.J., and Ilyin, V.I., "Sodium Channel Blockers," *J. Med. Chem.* 50(11):2583-2588, American Chemical Society, United States (2007).

Lai, J., et al., "The role of voltage-gated sodium channels in neuropathic pain," *Curr. Opin. Neurobiol.* 13(3):291-297, Elsevier Science Ltd., England (2003).

Lai, J., et al., "Voltage-gated sodium channels and hyperalgesia," *Annu. Rev. Pharmacol. Toxicol.* 44:371-397, Annual Reviews, United States (2004).

Laird, J.M.A., et al., "Deficits in visceral pain and referred hyperalgesia in Nav1.8 (SNS/PN3)-null mice," *J. Neurosci.* 22(19):8352-8356, Society for Neuroscience, United States (2002).

Liu, H., et al., "Mutations in cardiac sodium channels: clinical implications," *Am. J. Pharmacogenomics* 3(3):173-179, Adis Data Information BV, New Zealand (2003).

Majumdar, B., et al., "An electrocochleographic study of the effects of lignocaine on patients with tinnitus," *Clin. Otolaryngol. Allied Sci.* 8(3):175-180, Blackwell Scientific Publications, England (1983).

Meisler, M.H. and Kearney, J.A., "Sodium channel mutations in epilepsy and other neurological disorders," *J. Clin. Invest.* 115(8):2010-2017, American Society for Clinical Investigation, United States (2005).

Møller, A.R., "Similarities between chronic pain and tinnitus," *Am. J. Otol.* 18(5):577-585, Lippincott-Raven, United States (1997).

Nassar, M.A., et al., "Nociceptor-specific gene deletion reveals a major role for $Na_v1.7$ (PN1) in acute and inflammatory pain," *Proc. Natl. Acad. Sci. USA* 101(34):12706-12711, National Academy of Sciences, United States (2004).

Nielsen, N.M. and Bundgaard, H., "Glycolamide esters as biolabile prodrugs of carboxylic acid agents: synthesis, stability, bioconversion, and physicochemical properties," *J. Pharm. Sci.* 77(4):285-298, American Pharmaceutical Assn., United States (1988).

Noble, D., "Unraveling the genetics and mechanisms of cardiac arrhythmia," *Proc. Natl. Sci. USA* 99(9):5755-5756, National Academy of Sciences, United States (2002).

Seltzer, Z., et al., "A novel behavioral model of neuropathic pain disorders produced in rats by partial sciatic nerve injury," *Pain* 43(2):205-218, ElsevierScience Publishers B.V., Netherlands (1990).

Shao, B., et al., "Phenoxyphenyl pyridines as novel state-dependent, high-potency sodium channel inhibitors," *J. Med. Chem.* 47:4277-4285, American Chemical Society, United States (2004).

Simpson, J.J. and Davies, W.E., "Recent advances in the pharmacological treatment of tinnitus," *Trends Pharmacol. Sci.* 20(1):12-18, Elsevier Science, England (1999).

Srivatsa, U., et al., "Mechanisms of antiarrhythmic drug actions and their clinical relevance for controlling disorders of cardiac rhythm," *Curr. Cardiol. Rep.* 4(5):401-410, Current Science Inc., United States (2002).

Stein, C., et al., "Unilateral Inflammation of the Hindpaw in Rats as a Model of Prolonged Noxious Stimulation: Alterations in Behavior and Nociceptive Thresholds," *Pharmacology Biochemistry & Behavior* 31:445-451, Pergamon Press plc, United States (1988).

Taylor, C.P. and Meldrum, B.S., "$Na^+$ channels as targets for neuroprotective drugs," *Trends Pharmacol. Sci.* 16(9)309-316, Elsevier Science Ltd., England (1995).

(56) References Cited

OTHER PUBLICATIONS

Toledo-Aral, J.J., et al., "Identification of PN1, a predominant voltage-dependent sodium channel expressed principally in peripheral neurons," *Proc. Natl. Acad. Sci. USA* 94(4):1527-1532, National Academy of Sciences, United States (1997).

Tonndorf, J., "The analogy between tinnitus and pain: a suggestion for physiological basis of chronic tinnitus," *Hearing Research* 28(2-3):271-275, Elsevier Science Publishers B.V., Netherlands (1987).

Van Tonder, E.C., et al., "Preparation and physicochemical characterization of 5 niclosamide solvates and 1 hemisolvate," *AAPS PharmSci Tech* 5(1):1-10, Springer, United States (2004).

Wood, J.N., et al., "Voltage-gated sodium channels and pain pathways," *J. Neurobiol.* 61(1):55-71, Wiley Periodicals, Inc., United States (2004).

Yogeeswari, P., et al., "Ion channels as important targets for antiepileptic drug design," *Curr. Drug Targets* 5(7):589-602, Bentham Science Publishers Ltd., Netherlands (2004).

Yokoyama, K., et al., "Potent and orally bioavailable CCR4 antagonists: Synthesis and structure-activity relationship study of 2-aminoquinazolines," *Bioorg. Med. Chem.* 17(1):64-73, Elsevier Science, England (2009).

Mason, J.J. and Bergman, J., "Total synthesis of luotonin A and 14-substituted analogues," *Org. Biomol. Chem.* 5(15):2486-2490, The Royal Society of Chemistry, England (2007).

\* cited by examiner

QUINAZOLINE COMPOUNDS AS SODIUM CHANNEL BLOCKERS

BACKGROUND OF THE INVENTION

1. Field of the Invention

This invention is in the field of medicinal chemistry. The invention relates to novel aryl and heteroaryl substituted quinazolyl compounds and the use of these compounds as blockers of sodium ($Na^+$) channels.

2. Background Art

Voltage-gated sodium channels (VGSCs) are found in all excitable cells. In neuronal cells of the central nervous system (CNS) and peripheral nervous system (PNS) sodium channels are primarily responsible for generating the rapid upstroke of the action potential. In this manner sodium channels are essential to the initiation and propagation of electrical signals in the nervous system. Proper function of sodium channels is therefore necessary for normal function of the neuron. Consequently, aberrant sodium channel function is thought to underlie a variety of medical disorders (See Hubner et al., *Hum. Mol. Genet.* 11:2435-2445 (2002) for a general review of inherited ion channel disorders) including epilepsy (Yogeeswari et al, *Curr. Drug Target* 5:589-602 (2004)), arrhythmia (Noble, *Proc. Natl. Acad. Sci. USA* 99:5755-5756 (2002)), myotonia (Cannon, *Kidney Int.* 57:772-779 (2000)), and pain (Wood et al., *J. Neurobiol.*, 61:55-71 (2004)).

VGSCs are composed of one α-subunit, which forms the core of the channel and is responsible for voltage-dependent gating and ion permeation, and several auxiliary β-subunits (see, e.g., Chahine et al., *CNS & Neurological Disorders-Drug Targets* 7: 144-158 (2008) and Kyle and Ilyin, *J. Med. Chem.* 50:2583-2588 (2007)). α-Subunits are large proteins composed of four homologous domains. Each domain contains six α-helical transmembrane spanning segments. There are currently 9 known members of the family of voltage-gated sodium channel α-subunits. Names for this family include SCNx, SCNAx, and $Na_v$x.x (see Table 1, below). The VGSC family has been phylogenetically divided into two subfamilies $Na_v$1.x (all but SCN6A) and $Na_v$2.x (SCN6A). The $Na_v$1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v$1.5, H1) is almost exclusively expressed in cardiac tissue and has been shown to underlie a variety of cardiac arrhythmias and other conduction disorders (Liu et al., *Am. J. Pharmacogenomics* 3:173-179 (2003)). Consequently, blockers of $Na_v$1.5 have found clinical utility in treatment of such disorders (Srivatsa et al., *Curr. Cardiol. Rep.* 4:401-410 (2002)). The remaining TTX-resistant sodium channels, $Na_v$1.8 (SCN10A, PN3, SNS) and $Na_v$1.9 (SCN11A, NaN, SNS2) are expressed in the peripheral nervous system and show preferential expression in primary nociceptive neurons. Human genetic variants of these channels have not been associated with any inherited clinical disorder. However, aberrant expression of $Na_v$1.8 has been found in the CNS of human multiple sclerosis (MS) patients and also in a rodent model of MS (Black et al., *Proc. Natl. Acad. Sci. USA* 97:11598-115602 (2000)). Evidence for involvement in nociception is both associative (preferential expression in nociceptive neurons) and direct (genetic knockout). $Na_v$1.8-null mice exhibited typical nociceptive behavior in response to acute noxious stimulation but had significant deficits in referred pain and hyperalgesia (Laird et al., *J. Neurosci.* 22:8352-8356 (2002)).

TABLE 1

Voltage-gated sodium channel gene family

| Type | Gene Symbol | Tissue Distribution | TTX $IC_{50}$ (nM) | Disease Association | Indications |
|---|---|---|---|---|---|
| $Na_v$1.1 | SCN1A | CNS/PNS | 10 | Epilepsy | Pain, seizures, neurodegeneration |
| $Na_v$1.2 | SCN2A | CNS | 10 | Epilepsy | Epilepsy, neurodegeneration |
| $Na_v$1.3 | SCN3A | CNS | 15 | — | Pain |
| $Na_v$1.4 | SCN4A | Skeletal muscle | 25 | Myotonia | Myotonia |
| $Na_v$1.5 | SCN5A | Heart muscle | 2,000 | Arrhythmia | Arrhythmia |
| $Na_v$1.6 | SCN8A | CNS/PNS | 6 | — | Pain, movement disorders |
| $Na_v$1.7 | SCN9A | PNS | 25 | Erythermalgia | Pain |
| $Na_v$1.8 | SCN10A | PNS | 50,000 | — | Pain |
| $Na_v$1.9 | SCN11A | PNS | 1,000 | — | Pain |

The $Na_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA* 94:1527-1532 (1997)).

An increasing body of evidence suggests that $Na_v$1.7 may play a key role in various pain states, including acute, inflammatory and/or neuropathic pain. Deletion of the SCN9A gene in nociceptive neurons of mice led to an increase in mechanical and thermal pain thresholds and reduction or abolition of inflammatory pain responses (Nassar et al., *Proc Natl. Acad. Sci. USA* 101:12706-12711 (2004)).

Sodium channel-blocking agents have been reported to be effective in the treatment of various disease states, and have found particular use as local anesthetics, e.g., lidocaine and bupivacaine, and in the treatment of cardiac arrhythmias, e.g., propafenone and amiodarone, and epilepsy, e.g., lamotrigine, phenyloin and carbamazepine (see Clare et al., *Drug Discovery Today* 5:506-510 (2000); Lai et al., *Annu. Rev. Pharmacol. Toxicol.* 44:371-397 (2004); Anger et al., *J. Med. Chem.* 44:115-137 (2001), and Catterall, *Trends Pharmacol. Sci.* 8:57-65 (1987)). Each of these agents is believed to act by interfering with the rapid influx of sodium ions.

Other sodium channel blockers such as BW619C89 and lifarizine have been shown to be neuroprotective in animal models of global and focal ischemia (Graham et al., *J. Pharmacol. Exp. Ther.* 269:854-859 (1994); Brown et al., *British J. Pharmacol.* 115:1425-1432 (1995)).

It has also been reported that sodium channel-blocking agents may be useful in the treatment of pain, including acute, chronic, inflammatory, neuropathic, and other types of pain such as rectal, ocular, and submandibular pain typically associated with paroxysmal extreme pain disorder; see, for example, Kyle and Ilyin, *J. Med. Chem.* 50:2583-2588 (2007); Wood et al., *J. Neurobiol.* 61:55-71 (2004); Baker et al., *TRENDS in Pharmacological Sciences* 22:27-31 (2001); and Lai et al., *Current Opinion in Neurobiology* 13:291-297 (2003); the treatment of neurological disorders such as epilepsy, seizures, epilepsy with febrile seizures, epilepsy with benign familial neonatal infantile seizures, inherited pain disorders, e.g., primary erthermalgia and paroxysmal extreme pain disorder, familial hemiplegic migraine, and movement disorder; and the treatment of other psychiatric disorders such as autism, cerebeller atrophy, ataxia, and mental retardation; see, for example, Chahine et al., *CNS & Neurological Disorders-Drug Targets* 7:144-158 (2008) and Meisler and Kearney, *J. Clin. Invest.* 115:2010-2017 (2005). In addition to the above-mentioned clinical uses, carbamazepine, lidocaine and phenyloin are occasionally used to treat neuropathic pain, such as from trigeminal neuralgia, diabetic neuropathy and other forms of nerve damage (Taylor and Meldrum, *Trends Pharmacol. Sci.* 16:309-316 (1995)). Furthermore, based on a number of similarities between chronic pain and tinnitus, (Moller, *Am. J. Otol.* 18:577-585 (1997); Tonndorf, *Hear. Res.* 28:271-275 (1987)) it has been proposed that tinnitus should be viewed as a form of chronic pain sensation (Simpson, et al., *Tip.* 20:12-18 (1999)). Indeed, lidocaine and carbamazepine have been shown to be efficacious in treating tinnitus (Majumdar, B. et al., *Clin. Otolaryngol.* 8:175-180 (1983); Donaldson, *Laryngol. Otol.* 95:947-951 (1981)).

Many patients with either acute or chronic pain disorders respond poorly to current pain therapies, and the development of resistance or insensitivity to opiates is common. In addition, many of the currently available treatments have undesirable side effects.

In view of the limited efficacy and/or unacceptable side-effects of the currently available agents, there is a pressing need for more effective and safer analgesics that work by blocking sodium channels.

BRIEF SUMMARY OF THE INVENTION

The present invention is related to the use of quinazolyl compounds represented by Formula I, below, and the pharmaceutically acceptable salts, prodrugs and solvates thereof (collectively referred to herein as "Compounds of the Invention"), as blockers of sodium ($Na^+$) channels.

The present invention is also related to treating a disorder responsive to the modulation, in particular blockade of sodium channels in a mammal suffering from excess activity of said channels by administering an effective amount of a Compound of the Invention as described herein.

Compounds useful in the present invention have not been heretofore reported. Thus, one aspect of the present invention is directed to novel compounds of Formula I, as well as their pharmaceutically acceptable salts, prodrugs and solvates.

Another aspect of the present invention is directed to the use of the novel compounds of Formula I, and their pharmaceutically acceptable salts, prodrugs and solvates, as modulators, in particular blockers of sodium channels.

A further aspect of the present invention is to provide a method for treating pain (e.g., acute pain, chronic pain, which includes but is not limited to, neuropathic pain, postoperative pain and inflammatory pain, or surgical pain) by administering an effective amount of a Compound of the Invention to a mammal in need of such treatment. Specifically, the present invention provides a method for preemptive or palliative treatment of pain by administering an effective amount of a Compound of the Invention to a mammal in need of such treatment.

A further aspect of the present invention is to provide a method for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, by administering an effective amount of a Compound of the Invention to a mammal in need of such treatment.

A further aspect of the present invention is to provide a pharmaceutical composition useful for treating a disorder responsive to the blockade of sodium ion channels, said pharmaceutical composition containing an effective amount of a Compound of the Invention in a mixture with one or more pharmaceutically acceptable carriers.

Also, an aspect of the present invention is to provide a method of modulating, preferably blocking, sodium channels in a mammal, wherein said method comprises administering to the mammal an effective amount of at least one Compound of the Invention.

A further aspect of the present invention is to provide a Compound of the Invention for use in treating pain (e.g., acute pain, chronic pain, which includes but is not limited to, neuropathic pain, postoperative pain and inflammatory pain, or surgical pain) in a mammal.

A further aspect of the present invention is to provide a Compound of the Invention for use in the treatment of stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia in a mammal.

A further aspect of the present invention is to provide radiolabeled Compounds of the Invention and the use of such compounds as radioligands in any appropriately selected competitive binding assays and screening methodologies. Thus, the present invention further provides a method for screening a candidate compound for its ability to bind to a sodium channel or a sodium channel subunit using a radiolabeled Compound of the Invention. In certain embodiments, the compound is radiolabeled with $^3H$, $^{11}C$, or $^{14}C$. This competitive binding assay can be conducted using any appropriately selected methodology. In one embodiment, the screening method comprises i) introducing a fixed concentration of the radiolabeled compound to an in vitro preparation comprising a soluble or membrane-associated sodium channel, subunit or fragment under conditions that permit the radiolabeled compound to bind to the channel, subunit or fragment, respectively, to form a conjugate; ii) titrating the mixture with a candidate compound; and iii) determining the ability of the candidate compound to displace the radiolabeled compound from said channel, subunit or fragment.

A further aspect of the present invention is to provide the use of a Compound of the Invention in the manufacture of a medicament for treating pain in a mammal. In one embodiment, the invention provides the use of a Compound of the invention in the manufacture of a medicament for palliative or preemptive treatment of pain, such as acute pain, chronic pain, or surgical pain.

A further aspect of the present invention is to provide the use of a Compound of the Invention in the manufacture of a medicament for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia in a mammal.

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention as claimed.

DETAILED DESCRIPTION OF THE INVENTION

One aspect of the present invention is based on the use of compounds of Formula I, and the pharmaceutically acceptable salts, prodrugs and solvates thereof, as blockers of $Na^+$ channels. In view of this property, compounds of Formula I, and the pharmaceutically acceptable salts, prodrugs and solvates thereof, are useful for treating disorders responsive to the blockade of sodium ion channels.

The compounds useful in this aspect of the invention are compounds represented by Formula I:

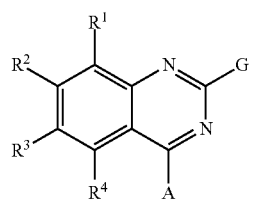

I and the pharmaceutically acceptable salts, prodrugs and solvates thereof, wherein:

$R^1$, $R^2$, $R^3$, and $R^4$ are each independently selected from the group consisting of hydrogen, alkyl, alkenyl, alkynyl, halogen, hydroxy, hydroxyalkyl, haloalkyl, cyano; amino, alkylamino, dialkylamino, alkoxy, aminocarbonyl, alkylaminocarbonyl, dialkylaminocarbonyl, alkylcarbonylamino, alkylcarbonyloxy, carboxy, alkoxycarbonyl, amino sulfonyl, alkylsulfonylamino, (alkylsulfonylamino)alkyl, ureido, (aminocarbonyl)alkylamino, and (carboxyalkyl)amino;

G is $G^1$, $G^2$, $G^3$, or $G^4$, wherein
$G^1$ is —$NR^5R^6$, wherein
$R^5$ is H, alkyl, or $NH_2$,
$R^6$ is
a) H,
b) alkyl,
c) hydroxyalkyl,
d) (aminocarbonyl)alkyl,
e) (aminocarbonyl)(hydroxy)alkyl;
f) aminoalkyl,
g) alkylaminoalkyl,
h) dialkylaminoalkyl,
i) cycloalkyl, unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;

j) (cycloalkyl)alkyl, wherein the cycloalkyl is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;

k) aryl, unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;

l) arylalkyl, wherein the aryl group is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;

m) heteroaryl, unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;

n) heteroarylalkyl, wherein the heteroaryl group is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;

o) heterocyclo, unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano; or p) heterocycloalkyl, wherein the heterocyclo is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano; or $R^5$ and $R^6$ together with the nitrogen atom to which they are attached form a 5- or 6-membered heterocyclic ring having carbon atoms and 1 or 2 nitrogen atoms, wherein the heterocyclic ring is unsubstituted or substituted with one or more substituents each independently selected from the group consisting of oxo, alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;

$G^2$ is

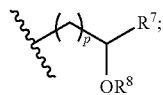

p is 0, 1 or 2;
$R^7$ is
a) —$(CH_2)_qOH$, wherein q is 0-5; or
b) selected from the group consisting of hydrogen, amino, alkylamino, dialkylamino, and alkoxy; and
$R^8$ is hydrogen or a bond (i.e. —$OR^8$ is =O);

$G^3$ is a 5- or 6-membered heteroaryl containing at least one nitrogen atom, wherein the heteroaryl is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano; and $G^4$ is —$OR^9$, wherein $R^9$ is alkyl, alkenyl, alkynyl, hydroxyalkyl, aminoalkyl, alkylamino alkyl, dialkylaminoalkyl, aminocarbonylalkyl, carboxyalkyl, alkoxycarbonylalkyl, arylalkyl, heteroarylalkyl, aryl or heteroaryl, wherein said aryl and heteroaryl groups are unsubstituted or substituted with one or more substituents selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;

A is

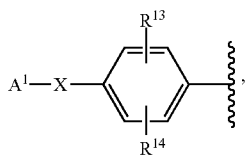

wherein $A^1$ is aryl or heteroaryl, any of which is optionally substituted;

X is —O—, —SO—, —$SO_2$—, —$CH_2$—, or —NH—; and $R^{13}$ and $R^{14}$ are each independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl.

In one embodiment, Compounds of the Invention are compounds of Formula I, and the pharmaceutically acceptable salts, prodrugs and solvents thereof, as defined above, with the proviso that when G is $G^1$, where $R^5$ is hydrogen or alkyl and $R^6$ is hydrogen, alkyl or cycloalkyl, and X is O, then no two of $R^1$, $R^2$, $R^3$ and $R^4$ are alkoxy at the same time.

In one embodiment, Compounds of the Invention are compounds of Formula I, where G is $G^1$, that is —$NR^5R^6$, wherein $R^5$ and $R^6$ are as defined above for Formula I.

In another embodiment, Compounds of the Invention are compounds of Formula I, wherein G is $G^1$, and where $R^5$ in $G^1$ is H and $R^6$ is as defined above for Formula I.

In another embodiment, Compounds of the Invention are compounds of Formula I, wherein G is $G^1$, and where $R^5$ in $G^1$ is alkyl and $R^6$ is as defined above for Formula I. Useful alkyl groups for $R^5$ include straight chain and branched chain $C_{1-6}$ alkyl groups. Preferably, $R^5$ is $C_{1-4}$ alkyl. Useful alkyl groups for $R^5$ include methyl, ethyl, propyl, isopropyl, butyl, tert-butyl, and sec-butyl, and typically methyl and ethyl.

In another embodiment, Compounds of the Invention are compounds of Formula I, wherein G is $G^1$, and where $R^5$ in $G^1$ is $NH_2$ and $R^6$ is as defined above for Formula I.

In another embodiment, Compounds of the Invention are compounds of Formula I, wherein G is $G^1$, and where $R^6$ in $G^1$ is hydrogen and $R^5$ is as defined above for Formula I. In another embodiment, Compounds of the Invention are compounds of Formula I, wherein $G^1$ is —$NH_2$ or —$NH(NH_2)$.

In another embodiment, Compounds of the Invention are compounds of Formula I, wherein G is $G^1$, and where $R^6$ in $G^1$ is alkyl and $R^5$ is as defined above for Formula I. Useful alkyl groups for $R^6$ include straight chain and branched chain $C_{1-6}$ alkyl groups. Preferably, $R^6$ is $C_{1-4}$ alkyl. Useful alkyl groups for $R^6$ include methyl, ethyl, propyl, isopropyl, butyl, tert-butyl, and sec-butyl, and typically methyl and ethyl. In another embodiment, Compounds of the Invention are compounds of Formula I, wherein $G^1$ is —$NH(C_{1-4}$ alkyl), —$N(C_{1-4}$ alkyl)($C_{1-4}$alkyl), or —$N(NH_2)(C_{1-4}$ alkyl).

In another embodiment, Compounds of the Invention are compounds of Formula I, wherein G is $G^1$, and where $R^6$ in $G^1$ is hydroxyalkyl and $R^5$ is as defined above for Formula I. Useful hydroxyalkyl groups for $R^6$ include straight chain or branched chain mono-, di-, and tri-hydroxyalkyl groups, and typically straight chain or branched chain mono- and dihydroxyalkyl groups. Useful monohydroxyalkyl groups include monohydroxy($C_{2-6}$)alkyl groups, and preferably monohydroxy($C_{2-4}$)alkyl groups, such as 2-hydroxyethyl, 2-hydroxypropyl, 3-hydroxypropyl, 2-hydroxybutyl, 3-hydroxybutyl, 4-hydroxybutyl, 2-hydroxy-1-methylethyl, and 2-hydroxy-1-methylpropyl. Useful dihydroxyalkyl groups include dihydroxy($C_{2-6}$)alkyl groups, and preferably dihydroxy($C_{2-4}$) alkyl groups, such as 1,2-dihydroxyethyl, 2,3-dihydroxypropyl, 2-hydroxy-1-hydroxymethylethyl, and 1,3-dihydroxyprop-2-yl. In one embodiment, $R^6$ is any hydroxyalkyl as defined above and $R^5$ is H. In another embodiment, $R^6$ is any hydroxyalkyl as defined above and $R^5$ is $NH_2$. In another embodiment, $R^6$ is any hydroxyalkyl as defined above and $R^5$ is $C_{1-4}$ alkyl. In another embodiment, Compounds of the Invention are compounds of Formula I, where G is $G^1$, $R^5$ is H, $NH_2$ or $C_{1-4}$ alkyl, and $R^6$ is selected from the group consisting of

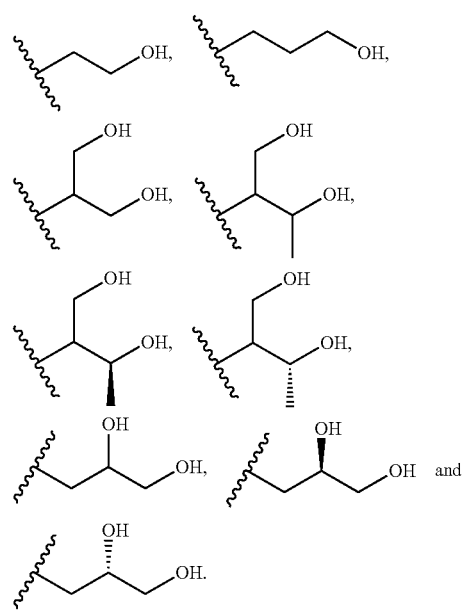

In another embodiment, Compounds of the Invention are compounds of Formula I, wherein $G^1$ is selected from the group consisting of

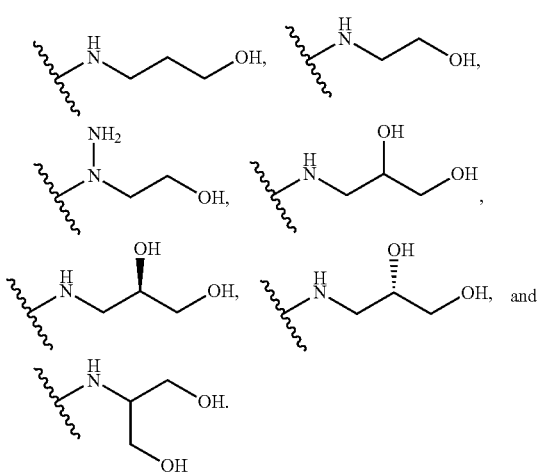

In another embodiment, Compounds of the Invention are compounds of Formula I, wherein G is $G^1$, and where $R^6$ in $G^1$ is (aminocarbonyl)alkyl and $R^5$ is as defined above. Useful (aminocarbonyl)alkyl groups for $R^6$ include straight chain or branched chain mono- or di(aminocarbonyl)alkyl groups. Useful mono(aminocarbonyl)alkyl groups include mono(aminocarbonyl)$C_{1-6}$ alkyl groups, and preferably mono(aminocarbonyl)$C_{1-4}$ alkyl groups, such as (aminocarbonyl)methyl, 1-(aminocarbonyl)ethyl, 2-(aminocarbonyl)ethyl, 1-(aminocarbonyl)propyl, 2-(aminocarbonyl)propyl, 3-(aminocarbonyl)propyl, 1-(aminocarbonyl)butyl, 2-(aminocarbonyl)butyl, 3-(aminocarbonyl)butyl, 4-(aminocarbonyl)butyl, 1-(aminocarbonyl)-2-methylpropyl, 2-aminocarbonyl-1-methylethyl, and 2-aminocarbonyl-1-methylpropyl. Useful di(aminocarbonyl)alkyl groups include di(aminocarbonyl)($C_{2-6}$)alkyl groups, and preferably di(aminocarbonyl)($C_{2-4}$) alkyl groups, such as 1,2-di(aminocarbonyl)ethyl, 2,3-di(aminocarbonyl)propyl, 2-(aminocarbonyl)-1-(aminocarbonyl)methylethyl, and 1,3-di(amino carbonyl)prop-2-yl. In one embodiment, $R^6$ is any (aminocarbonyl)alkyl group as defined above and $R^5$ is H. In another embodiment, $R^6$ is any (aminocarbonyl)alkyl group as defined above and $R^5$ is $NH_2$. In another embodiment, $R^6$ is any (aminocarbonyl)alkyl group as defined above and $R^5$ is $C_{1-4}$ alkyl. In another embodiment, Compounds of the Invention are compounds of Formula I, where $G^1$ is selected from the group consisting of

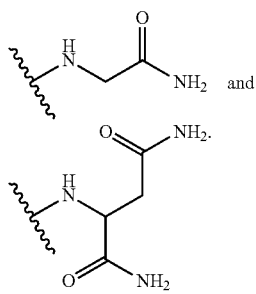

In another embodiment, Compounds of the Invention are compounds of Formula I, wherein G is $G^1$, and where $R^6$ in $G^1$ is (aminocarbonyl)(hydroxy)alkyl and $R^5$ is as defined above. Useful (aminocarbonyl)(hydroxy)alkyl groups for $R^6$ include straight chain or branched chain (aminocarbonyl)(hydroxy) alkyl groups. Useful (aminocarbonyl)(hydroxy)alkyl groups include (aminocarbonyl)(hydroxy)$C_{2-6}$ alkyl groups, and preferably (aminocarbonyl)(hydroxy)$C_{2-4}$ alkyl groups, such as 1-(aminocarbonyl)-2-hydroxyethyl, 2-(aminocarbonyl)-2-hydroxyethyl, 1-(aminocarbonyl)-2-hydroxypropyl, 1-(aminocarbonyl)-3-hydroxypropyl, 2-(aminocarbonyl)-3-hydroxypropyl, 2-hydroxy-3-(aminocarbonyl)propyl, 1-(aminocarbonyl)-2-hydroxybutyl, 1-(amino carbonyl)-3-hydroxybutyl, 1-(aminocarbonyl)-4-hydroxybutyl, 2-(aminocarbonyl)-3-hydroxybutyl, 2-(aminocarbonyl)-4-hydroxybutyl, 2-hydroxy-3-(aminocarbonyl)butyl, 2-hydroxy-4-(aminocarbonyl)butyl, 3-hydroxy-4-(aminocarbonyl)butyl, 1-(aminocarbonyl)-2-(hydroxymethyl)propyl, 2-aminocarbonyl-1-(hydroxymethyl)ethyl, and 2-aminocarbonyl-1-(hydroxymethyl)propyl. In one embodiment, $R^6$ is any (aminocarbonyl)(hydroxy)alkyl group as defined above and $R^5$ is H. In another embodiment, $R^6$ is any (aminocarbonyl)(hydroxy)alkyl group as defined above and $R^5$ is $NH_2$. In another embodiment, $R^6$ is any (aminocarbonyl)(hydroxy) alkyl group as defined above and $R^5$ is $C_{1-4}$ alkyl. In another embodiment, Compounds of the Invention are compounds of Formula I, where $G^1$ is

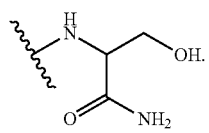

In another embodiment, Compounds of the Invention are compounds of Formula I, wherein G is $G^1$, and where $R^6$ in $G^1$ is aminoalkyl and $R^5$ is as defined above. Useful aminoalkyl groups for $R^6$ include straight chain and branched chain aminoalkyl groups. Useful aminoalkyl groups include amino($C_{1-6}$) alkyl groups, and preferably amino($C_{1-4}$alkyl groups, such as aminomethyl, 2-aminoethyl, 1-aminoethyl, 1-aminopropyl, 2-aminopropyl, 3-aminopropyl, 1-aminobutyl, 2-aminobutyl, 3-aminobutyl, 4-aminobutyl, 2-amino-1-methylethyl, and 2-amino-1-methylpropyl. In one embodiment, $R^6$ is any aminoalkyl as defined above and $R^5$ is H. In another embodiment, $R^6$ is any aminoalkyl as defined above and $R^5$ is $NH_2$. In another embodiment, $R^6$ is any aminoalkyl as defined above and $R^5$ is $C_{1-4}$ alkyl.

In another embodiment, Compounds of the Invention are compounds of Formula I, wherein G is $G^1$, and where $R^6$ in $G^1$ is alkylaminoalkyl and $R^5$ is as defined above. Useful alkylaminoalkyl groups for $R^6$ include straight chain and branched chain alkylaminoalkyl groups. Useful alkylaminoalkyl groups include $C_{1-4}$ alkylamino($C_{1-6}$)alkyl groups, and preferably $C_{1-2}$ alkylamino($C_{1-4}$)alkyl groups, such as methylaminomethyl, 2-methylaminoethyl, 1-methylaminopropyl, 2-methylaminopropyl, 3-methylaminopropyl, 1-methylaminobutyl, 2-methylaminobutyl, 3-methylaminobutyl, 4-methylaminobutyl, 2-methylamino-1-methylethyl, and 2-methylamino-1-methylpropyl. In one embodiment, $R^6$ is any alkylaminoalkyl as defined above and $R^5$ is H. In another embodiment, $R^6$ is any alkylaminoalkyl as defined above and $R^5$ is $NH_2$. In another embodiment, $R^6$ is any alkylaminoalkyl as defined above and $R^5$ is $C_{1-4}$ alkyl.

In another embodiment, Compounds of the Invention are compounds of Formula I, wherein G is $G^1$, and where $R^6$ in $G^1$ is dialkylaminoalkyl and $R^5$ is as defined above. Useful dialkylaminoalkyl groups for $R^6$ include straight chain and branched chain dialkylaminoalkyl groups. Useful dialkylaminoalkyl groups include di($C_{1-4}$ alkyl)amino($C_{1-6}$)alkyl groups, and preferably di($C_{1-2}$ alkyl)amino($C_{1-4}$alkyl groups, such as dimethylaminomethyl, 1-dimethylaminoethyl, 2-dimethylaminoethyl, 1-dimethylaminopropyl, 2-dimethylaminopropyl, 3-dimethylaminopropyl, 1-dimethylaminobutyl, 2-dimethylaminobutyl, 3-dimethylaminobutyl, 4-dimethylaminobutyl, 2-dimethylamino-1-methylethyl, and 2-dimethylamino-1-methylpropyl. In one embodiment, $R^6$ is any dialkylaminoalkyl as defined above and $R^5$ is H. In another embodiment, $R^6$ is dimethylamino($C_{2-4}$)alkyl and $R^5$ is H. In another embodiment, $R^6$ is any dialkylaminoalkyl as defined above and $R^5$ is $NH_2$. In another embodiment, $R^6$ is any dialkylaminoalkyl as defined above and $R^5$ is $C_{1-4}$ alkyl.

In another embodiment, Compounds of the Invention are compounds of Formula I, wherein G is $G^1$, and where $R^6$ in $G^1$ is cycloalkyl, unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. In one embodiment, $R^6$ is unsubstituted $C_{3-6}$ cycloalkyl. In another embodiment, $R^6$ is $C_{3-6}$ cycloalkyl substituted with one or more, preferably 1 or 2, substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. Useful substituents for the cycloalkyl group include $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, amino, amino($C_{1-6}$)alkyl, $C_{1-4}$ alkylamino($C_{1-6}$) alkyl, di($C_{1-4}$)alkylamino($C_{1-6}$)alkyl, aminocarbonyl, carboxy, $C_{1-6}$ alkoxycarbonyl, and cyano; and preferably $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$)alkyl, amino, amino($C_{1-4}$)alkyl, $C_{1-2}$ alkylamino($C_{1-4}$)alkyl, di($C_{1-2}$)alkylamino($C_{1-4}$)alkyl, aminocarbonyl, carboxy, $C_{1-4}$ alkoxycarbonyl, and cyano. Useful $C_{3-6}$ cycloalkyl groups include cyclopropyl, cyclobutyl, cyclopentyl, and cyclohexyl, which can be unsubstituted or substituted as defined above. In one embodiment, $R^6$ is any cycloalkyl as defined above and $R^5$ is H. In another embodiment, $R^6$ is any cycloalkyl as defined above and $R^5$ is $NH_2$. In another embodiment, $R^6$ is any cycloalkyl as defined above and $R^5$ is $C_{1-4}$ alkyl.

In another embodiment, Compounds of the Invention are compounds of Formula I, wherein G is $G^1$, and where $R^6$ in $G^1$ is (cycloalkyl)alkyl, wherein the cycloalkyl group is unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. In one embodiment, $R^6$ is unsubstituted ($C_{3-6}$ cycloalkyl)alkyl, and preferably unsubstituted ($C_{3-6}$ cycloalkyl)($C_{1-6}$)alkyl. In another embodiment, $R^6$ is ($C_{3-6}$ cycloalkyl)alkyl, and preferably ($C_{3-6}$ cycloalkyl)($C_{1-6}$) alkyl, wherein the $C_{3-6}$ cycloalkyl is substituted with one or more, preferably 1 or 2, substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. Useful substituents for the cycloalkyl group include $C_{1-6}$ alkyl, $C_{1-6}$ alkoxy, halogen, halo($C_{1-6}$)alkyl, halo($C_{1-6}$)alkoxy, hydroxy, hydroxy ($C_{1-6}$)alkyl, amino, amino($C_{1-6}$)alkyl, $C_{1-4}$ alkylamino($C_{1-6}$) alkyl, di($C_{1-4}$)alkylamino($C_{1-6}$)alkyl, aminocarbonyl, carboxy, $C_{1-6}$ alkoxycarbonyl, and cyano; and preferably $C_{1-4}$ alkyl, $C_{1-4}$ alkoxy, halogen, halo($C_{1-4}$)alkyl, halo($C_{1-4}$) alkoxy, hydroxy, hydroxy($C_{1-4}$)alkyl, amino, amino($C_{1-4}$) alkyl, $C_{1-2}$ alkylamino($C_{1-4}$alkyl, di($C_{1-2}$)alkylamino($C_{1-4}$) alkyl, aminocarbonyl, carboxy, $C_{1-4}$ alkoxycarbonyl, and cyano. Useful ($C_{3-6}$ cycloalkyl)($C_{1-6}$)alkyl groups include cyclopropylmethyl, cyclopropylethyl, cyclopropylpropyl, cyclobutylmethyl, cyclobutyl ethyl, cyclobutylpropyl, cyclopentylmethyl, cyclopentylethyl, cyclopentylpropyl, cyclohexylmethyl, cyclohexylethyl and cyclohexylpropyl, wherein the cycloalkyl group can be unsubstituted or substituted as defined above. In one embodiment, $R^6$ is any (cycloalkyl)alkyl as defined above and $R^5$ is H. In another embodiment, $R^6$ is any (cycloalkyl)alkyl as defined above and $R^5$ is $NH_2$. In another embodiment, $R^6$ is any (cycloalkyl) alkyl as defined above and $R^5$ is $C_{1-4}$ alkyl.

In another embodiment, Compounds of the Invention are compounds of Formula I, wherein G is $G^1$, and where $R^6$ in $G^1$ is aryl, unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. In one embodiment, $R^6$ is unsubstituted $C_{6-14}$ aryl, and preferably $C_{6-12}$ aryl. In another embodiment, $R^6$ is $C_{6-14}$ aryl, and preferably $C_{6-12}$ aryl, substituted with one or more, preferably 1 or 2, substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. Useful substituents for the aryl group include $C_{1-6}$ alkyl, $C_{1-6}$ alkoxy, halogen, halo($C_{1-6}$)alkyl, halo($C_{1-6}$) alkoxy, hydroxy, hydroxy($C_{1-6}$)alkyl, amino, amino($C_{1-6}$) alkyl, $C_{1-4}$ alkylamino($C_{1-6}$)alkyl, di($C_{1-4}$)alkylamino($C_{1-6}$) alkyl, aminocarbonyl, carboxy, $C_{1-6}$ alkoxycarbonyl, and cyano; and preferably $C_{1-4}$ alkyl, $C_{1-4}$ alkoxy, halogen, halo ($C_{1-4}$alkyl, halo($C_{1-4}$)alkoxy, hydroxy, hydroxy($C_{1-4}$alkyl, amino, amino($C_{1-4}$alkyl, $C_{1-2}$ alkylamino($C_{1-4}$)alkyl, di($C_{1-2}$) alkylamino($C_{1-4}$)alkyl, aminocarbonyl, carboxy, $C_{1-4}$ alkoxycarbonyl, and cyano. Useful $C_{6-12}$ aryl groups include phenyl, naphthyl and biphenyl, which can be unsubstituted or substituted as defined above. In one embodiment, $R^6$ is any aryl as defined above and $R^5$ is H. In another embodiment, $R^6$ is any aryl as defined above and $R^5$ is $NH_2$. In another embodiment, $R^6$ is any aryl as defined above and $R^5$ is $C_{1-4}$ alkyl.

In another embodiment, Compounds of the Invention are compounds of Formula I, wherein G is $G^1$, and where $R^6$ in $G^1$ is arylalkyl, wherein the aryl group is unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. In one embodiment, $R^6$ is unsubstituted $C_{6-14}$ aryl($C_{1-6}$)alkyl, and preferably $C_{6-12}$ aryl($C_{1-4}$)alkyl. In another embodiment, $R^6$ is $C_{6-14}$ aryl($C_{1-6}$)alkyl, and preferably $C_{6-12}$ aryl($C_{1-4}$)alkyl, substituted with one or more, preferably 1 or 2, substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. Useful substituents for the aryl group include $C_{1-6}$ alkyl, $C_{1-6}$ alkoxy, halogen, halo($C_{1-6}$) alkyl, halo($C_{1-6}$)alkoxy, hydroxy, hydroxy($C_{1-6}$)alkyl, amino, amino($C_{1-6}$)alkyl, $C_{1-4}$ alkylamino($C_{1-6}$)alkyl, di($C_{1-4}$)alkylamino($C_{1-6}$)alkyl, aminocarbonyl, carboxy, $C_{1-6}$ alkoxycarbonyl, and cyano; and preferably $C_{1-4}$ alkyl, $C_{1-4}$ alkoxy, halogen, halo($C_{1-4}$alkyl, halo($C_{1-4}$)alkoxy, hydroxy, hydroxy($C_{1-4}$alkyl, amino, amino($C_{1-4}$)alkyl, $C_{1-2}$ alkylamino($C_{1-4}$)alkyl, di($C_{1-2}$)alkylamino($C_{1-4}$alkyl, aminocarbonyl, carboxy, $C_{1-4}$ alkoxycarbonyl, and cyano. Useful $C_{6-12}$ aryl($C_{1-4}$)alkyl groups include phenylmethyl, 1-phenylethyl, 2-phenylethyl, 3-phenylpropyl, 4-phenylbutyl, naphthylmethyl, 2-naphthylethyl, biphenylmethyl, 2-biphenylethyl, wherein the aryl group can be unsubstituted or substituted as defined above. In one embodiment, $R^6$ is any arylalkyl as defined above and $R^5$ is H. In another embodiment, $R^6$ is any arylalkyl as defined above and $R^5$ is $NH_2$. In another embodiment, $R^6$ is any arylalkyl as defined above and $R^5$ is $C_{1-4}$ alkyl.

In another embodiment, Compounds of the Invention are compounds of Formula I, wherein G is $G^1$, and where $R^6$ in $G^1$ is heteroaryl, unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. In one embodiment, $R^6$ is unsubstituted heteroaryl, and preferably unsubstituted 5- or 6-membered heteroaryl. In another embodiment, $R^6$ is heteroaryl, and preferably 5- or 6-membered heteroaryl, substituted with one or more, preferably 1 or 2, substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. Useful substituents for the heteroaryl group include $C_{1-6}$ alkyl, $C_{1-6}$ alkoxy, halogen, halo($C_{1-6}$)alkyl, halo ($C_{1-6}$)alkoxy, hydroxy, hydroxy($C_{1-6}$)alkyl, amino, amino ($C_{1-6}$)alkyl, $C_{1-4}$ alkylamino($C_{1-6}$)alkyl, di($C_{1-4}$)alkylamino ($C_{1-6}$)alkyl, aminocarbonyl, carboxy, $C_{1-6}$ alkoxycarbonyl, and cyano; and preferably $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$ alkyl, amino, amino($C_{1-4}$alkyl, $C_{1-2}$ alkylamino($C_{1-4}$alkyl, di($C_{1-2}$)alkylamino($C_{1-4}$)alkyl, aminocarbonyl, carboxy, $C_{1-4}$ alkoxycarbonyl, and cyano. Useful 5- or 6-membered heteroaryl groups include 5- or 6-membered heteroaryl groups having at least one nitrogen atom, such as pyrrolyl (e.g., 1H-pyrrol-2-yl and 1H-pyrrol-3-yl), imidazolyl (e.g., 1H-imidazol-2-yl, 1H-imidazol-4-yl, 1H-imidazol-5-yl, 2H-imidazol-2-yl, and 2H-imidazol-4-yl), 1,2,3-triazolyl (e.g., 1H-1,2,3-triazol-2-yl, 1H-1,2,3-triazol-4-yl, and 1H-1, 2,3-triazol-5-yl), 1,2,4-triazolyl (e.g., 1H-1,2,4-triazol-3-yl and 1H-1,2,4-triazol-5-yl), thiazolyl (e.g., thiazol-2-yl, thiazol-4-yl, and thiazol-5-yl), oxazolyl (e.g., oxazol-2-yl, oxazol-4-yl, and oxazol-5-yl), isooxazolyl (e.g., isoxazol-3-yl, isoxazol-4-yl, and isoxazol-5-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), pyridazinyl (e.g., pyridazin-3-yl or pyridazin-4-yl), and pyrazinyl (e.g., pyrazin-2-yl and pyrazin-3-yl), which can be unsubstituted or substituted as defined above. In one embodiment, $R^6$ is any heteroaryl as defined above and $R^5$ is H. In another embodiment, $R^6$ is any heteroaryl as defined above and $R^5$ is $NH_2$. In another embodiment, $R^6$ is any heteroaryl as defined above and $R^5$ is $C_{1-4}$ alkyl.

In another embodiment, Compounds of the Invention are compounds of Formula I, wherein G is $G^1$, and where $R^6$ in $G^1$ is heteroarylalkyl, wherein the heteroaryl group is unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. In one embodiment, $R^6$ is unsubstituted heteroaryl($C_{1-6}$)alkyl, and preferably unsubstituted 5- or 6-membered heteroaryl($C_{1-4}$alkyl. In another embodiment, $R^6$ is heteroaryl($C_{1-6}$)alkyl, and preferably 5- or 6-membered heteroaryl($C_{1-4}$)alkyl, substituted with one or more, preferably 1 or 2, substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. Useful substituents for the heteroaryl group include $C_{1-6}$ alkyl, $C_{1-6}$ alkoxy, halogen, halo($C_{1-6}$)alkyl, halo($C_{1-6}$)alkoxy, hydroxy, hydroxy ($C_{1-6}$)alkyl, amino, amino($C_{1-6}$)alkyl, $C_{1-4}$ alkylamino($C_{1-6}$) alkyl, di($C_{1-4}$)alkylamino($C_{1-6}$)alkyl, aminocarbonyl, carboxy, $C_{1-6}$ alkoxycarbonyl, and cyano; and preferably $C_{1-4}$ alkyl, $C_{1-4}$ alkoxy, halogen, halo($C_{1-4}$)alkyl, halo($C_{1-4}$) alkoxy, hydroxy, hydroxy($C_{1-4}$alkyl, amino, amino($C_{1-4}$ alkyl, $C_{1-2}$ alkylamino($C_{1-4}$alkyl, di($C_{1-2}$)alkylamino($C_{1-4}$ alkyl, aminocarbonyl, carboxy, $C_{1-4}$ alkoxycarbonyl, and cyano. Useful 5- or 6-membered heteroaryl groups in the heteroarylalkyl group include 5- or 6-membered heteroaryl groups having at least one nitrogen atom, such as pyrrolyl (e.g., pyrrol-1-yl, 1H-pyrrol-2-yl and 1H-pyrrol-3-yl), imidazolyl (e.g., imidazol-1-yl, 1H-imidazol-2-yl, 1H-imidazol-4-yl, 1H-imidazol-5-yl, 2H-imidazol-2-yl and 2H-imidazol-4-yl), 1,2,3-triazolyl (e.g., 1,2,3-triazol-1-yl, 1H-1,2,3-triazol-2-yl, 1H-1,2,3-triazol-4-yl, and 1H-1,2,3-triazol-5-yl), 1,2,4-triazolyl (e.g., 1,2,4-triazol-1-yl, 1H-1,2,4-triazol-3-yl and 1H-1,2,4-triazol-5-yl), thiazolyl (e.g., thiazol-2-yl, thiazol-4-yl, and thiazol-5-yl), oxazolyl (e.g., oxazol-2-yl, oxazol-4-yl, and oxazol-5-yl), isooxazolyl (e.g., isoxazol-3-yl, isoxazol-4-yl, and isoxazol-5-yl), pyrazolyl (e.g., pyrazol-1-yl, 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), pyridazinyl (e.g., pyridazin-3-yl or pyridazin-4-yl), and pyrazinyl (e.g., pyrazin-2-yl and pyrazin-3-yl), which can be unsubstituted or substituted as defined above. Typical heteroarylalkyl groups for $R^6$ include, for example, imidazol-1-ylmethyl, 2-(imidazol-1-yl)ethyl, 3-(imidazol-1-yl)propyl, 4-(imidazol-1-yl)butyl, 1H-imidazol-2-ylmethyl, 2-(1H-imidazol-2-yl)ethyl, 3-(1H-imidazol-2-yl)propyl, 4-(1H-imidazol-2-yl)butyl, 2H-imidazol-4-ylmethyl, 2-(2H-imidazol-4-yl)ethyl, 3-(2H-imidazol-4-yl)propyl, 4-(2H-imidazol-4-yl) butyl, pyrrol-1-ylmethyl, 2-(pyrrol-1-yl)ethyl, 3-(pyrrol-1-yl)propyl, 4-(pyrrol-1-yl)butyl, 1,2,3-triazol-1-ylmethyl, 2-(1,2,3-triazol-1-yl)ethyl, 3-(1,2,3-triazol-1-yl)propyl, 4-(1, 2,3-triazol-1-yl)butyl, 1,2,4-triazol-1-ylmethyl, 2-(1,2,4-triazol-1-yl)ethyl, 3-(1,2,4-triazol-1-yl)propyl, 4-(1,2,4-triazol-1-yl)butyl, pyridin-2-ylmethyl, 2-(pyridin-2-yl)ethyl, 3-(pyridin-2-yl)propyl, and 4-(pyridin-2-yl)butyl. In one embodiment, $R^6$ is any heteroarylalkyl as defined above and $R^5$ is H. In another embodiment, $R^6$ is any heteroarylalkyl as defined above and $R^5$ is $NH_2$. In another embodiment, $R^6$ is any heteroarylalkyl as defined above and $R^5$ is $C_{1-4}$ alkyl.

In another embodiment, Compounds of the Invention are compounds of Formula I, wherein G is $G^1$, and where $R^6$ in $G^1$ is heterocyclo, unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. In one embodiment, the heterocyclo is a 3-7 membered monocyclic ring system. In another embodiment, the heterocyclo is a 7-10 membered bicyclic ring system. In one embodiment, $R^6$ is unsubstituted 3-7 membered heterocyclo, and preferably unsubstituted 5- or 6-membered heterocyclo. In one embodiment, R⁶ is unsubstituted 7-10 membered heterocyclo. In another embodiment, R⁶ is a 3-7 membered heterocyclo, and preferably 5- or 6-membered heterocyclo, substituted with one or more, preferably 1 or 2, substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. In another embodiment, R⁶ is a 7-10 membered heterocyclo substituted with one or more, preferably 1 or 2, substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. Useful substituents for the heterocyclo group include $C_{1-6}$ alkyl, $C_{1-6}$ alkoxy, halogen, halo($C_{1-6}$)alkyl, halo($C_{1-6}$) alkoxy, hydroxy, hydroxy($C_{1-6}$)alkyl, amino, amino($C_{1-6}$) alkyl, $C_{1-4}$ alkylamino($C_{1-6}$)alkyl, di($C_{1-4}$)alkylamino($C_{1-6}$) alkyl, aminocarbonyl, carboxy, $C_{1-6}$ alkoxycarbonyl, and cyano; and preferably $C_{1-4}$ alkyl, $C_{1-4}$ alkoxy, halogen, halo ($C_{1-4}$alkyl, halo($C_{1-4}$)alkoxy, hydroxy, hydroxy($C_{1-4}$)alkyl, amino, amino($C_{1-4}$)alkyl, $C_{1-2}$ alkylamino($C_{1-4}$)alkyl, di($C_{1-2}$)alkylamino($C_{1-4}$alkyl, aminocarbonyl, carboxy, $C_{1-4}$ alkoxycarbonyl, and cyano. Useful 5- or 6-membered heterocyclo groups include 5- or 6-membered heterocyclo groups having at least one nitrogen atom, such as pyrrolidinyl (e.g., pyrrolidin-1-yl, pyrrolidin-2-yl and pyrrolidin-3-yl), imidazolidinyl (e.g., imidazolidin-1-yl, imidazolidin-2-yl and imidazolidin-4-yl), 2-oxo-imidazolidinyl (e.g., 2-oxo-imidazolidin-1-yl and 2-oxo-imidazolidin-4-yl), oxazolidinyl (e.g., oxazolidin-2-yl, oxazolidin-3-yl, oxazolidin-4-yl, and oxazolidin-5-yl), isooxazolidinyl (e.g., isoxazolidin-2-yl, isoxazolidin-3-yl, isoxazolidin-4-yl, and isoxazolidin-5-yl), 3-oxo-isoxazolidinyl (e.g., 3-oxo-isoxazolidin-2-yl and 3-oxo-isoxazolidin-4-yl), pyrazolidinyl (e.g., pyrazolidin-1-yl, pyrazolidin-3-yl and pyrazolidin-4-yl), piperidinyl (e.g., piperidin-1-yl, piperidin-2-yl, piperidin-3-yl, and piperidin-4-yl), 2-oxo-piperidinyl (e.g., 2-oxo-piperidin-1-yl, 2-oxo-piperidin-3-yl, 2-oxo-piperidin-5-yl and 2-oxo-piperidin-6-yl) and hexahydropyrimidinyl (e.g., hexahydropyrimidin-1-yl, hexahydropyrimidin-2-yl, hexahydropyrimidin-4-yl, and hexahydropyrimidin-5-yl), piperazinyl (e.g., piperazin-1-yl, piperazin-3-yl, and piperazin-4-yl), and morpholinyl (e.g., morpholin-2-yl, morpholin-3-yl, and morpholin-4-yl), which can be unsubstituted or substituted as defined above. Useful 7-10 membered heterocyclo groups for R⁶ include 9-azabicyclo[3.3.1]nonan-3-yl, which can be unsubstituted or substituted as defined above. Further useful 7-10 membered heterocyclo groups for R⁶ include endo-8-tert-butoxycarbonyl-8-azabicyclo[3.2.1]octan-3-yl and 8-methyl-8-azabicyclo [3.2.1]octan-3-yl. In one embodiment, R⁶ is any heterocyclo as defined above and R⁵ is H. In another embodiment, R⁶ is any heterocyclo as defined above and R⁵ is NH₂. In another embodiment, R⁶ is any heterocyclo as defined above and R⁵ is $C_{1-4}$ alkyl. In another embodiment, R⁶ is 3-oxo-isoxazolidin-4-yl and R⁵ is as defined for Formula I. In another embodiment, R⁶ is endo-9-methyl-9-azabicyclo[3.3.1]nonan-3-yl and R⁵ is as defined for Formula I. In another embodiment, Compounds of the Invention are compounds of Formula I, wherein G¹ is selected from the group consisting of

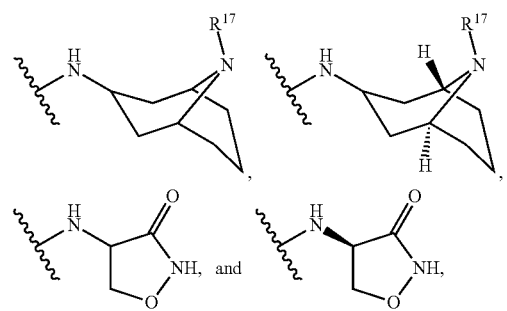

wherein R¹⁷ is hydrogen or $C_{1-4}$ alkyl, and typically methyl or ethyl.

In another embodiment, Compounds of the Invention are compounds of Formula I, wherein G is G¹, and where R⁶ in G¹ is heterocycloalkyl, wherein the heterocyclo is unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. In one embodiment, the heterocyclo group in the heterocycloalkyl is a 3-7 membered monocyclic ring system. In another embodiment, the heterocyclo group in the heterocycloalkyl is a 7-10 membered bicyclic ring system. In one embodiment, R⁶ is heterocycloalkyl, wherein the heterocyclo group is an unsubstituted 3-7 membered heterocyclo, and preferably unsubstituted 5- or 6-membered heterocyclo. In one embodiment, R⁶ is heterocycloalkyl, wherein the heterocyclo group is an unsubstituted 7-10 membered heterocyclo. In one embodiment, R⁶ is unsubstituted heterocyclo ($C_{1-6}$)alkyl, and preferably unsubstituted 5- or 6-membered heterocyclo($C_{1-4}$)alkyl. In another embodiment, R⁶ is heterocyclo($C_{1-6}$)alkyl, and preferably 5- or 6-membered heterocyclo($C_{1-4}$)alkyl, wherein the heterocyclo is substituted with one or more, preferably 1 or 2, substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. Useful substituents for the heterocyclo of the heterocycloalkyl group include $C_{1-6}$ alkyl, $C_{1-6}$ alkoxy, halogen, halo($C_{1-6}$)alkyl, halo ($C_{1-6}$)alkoxy, hydroxy, hydroxy($C_{1-6}$)alkyl, amino, amino ($C_{1-6}$)alkyl, $C_{1-4}$ alkylamino($C_{1-6}$)alkyl, di($C_{1-4}$)alkylamino ($C_{1-6}$)alkyl, aminocarbonyl, carboxy, $C_{1-6}$ alkoxycarbonyl, and cyano; and preferably $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$ alkyl, amino, amino($C_{1-4}$alkyl, $C_{1-2}$ alkylamino($C_{1-4}$)alkyl, di($C_{1-2}$)alkylamino($C_{1-4}$)alkyl, aminocarbonyl, carboxy, $C_{1-4}$ alkoxycarbonyl, and cyano. Useful 5- or 6-membered heterocyclo groups in the heterocycloalkyl include 5- or 6-membered heterocyclo groups having at least one nitrogen atom, such as pyrrolidinyl (e.g., pyrrolidin-1-yl, pyrrolidin-2-yl and pyrrolidin-3-yl), imidazolidinyl (e.g., imidazolin-1-yl, imidazolidin-2-yl and imidazolidin-4-yl), 2-oxo-imidazolidinyl (e.g., 2-oxo-imidazolidin-1-yl and 2-oxo-imidazolidin-4-yl), oxazolidinyl (e.g., oxazolidin-2-yl, oxazolidin-3-yl, oxazolidin-4-yl, and oxazolidin-5-yl), isooxazolidinyl (e.g., isoxazolidin-2-yl, isoxazolidin-3-yl, isoxazolidin-4-yl, and isoxazolidin-5-yl), 3-oxo-isoxazolidinyl (e.g., 3-oxo-isoxazolidin-4-yl and 3-oxo-isoxazolidin-2-yl), pyrazolidinyl (e.g., pyrazolidin-1-yl, pyrazolidin-3-yl and pyrazolidin-4-yl), piperidinyl (e.g., piperidin-1-yl, piperidin-2-yl, piperidin-3-yl, and piperidin-4-yl), 2-oxo-piperidinyl (e.g., 2-oxo-piperidin-1-yl, 2-oxo-piperidin-3-yl, 2-oxo-piperidin-5-yl and 2-oxo-piperidin-6-yl) and hexahydropyrimidinyl (e.g., hexahydropyrimidin-1-yl, hexahydropyrimidin-2-yl, hexahydropyrimidin-4-yl, and hexahydropyrimidin-5-yl), piperazinyl (e.g., piperazin-1-yl, piperazin-2-yl or piperazin-3-yl), and morpholinyl (e.g., morpholin-2-yl, morpholin-3-yl, and morpholin-4-yl), which can be unsubstituted or substituted as defined above. In another embodiment, $R^6$ is heterocyclo($C_{1-6}$)alkyl, wherein the heterocyclo is a bicyclic 7-10 membered ring. In this embodiment, useful 7-10 membered heterocyclo groups include 9-azabicyclo[3.3.1]nonan-3-yl, which can be unsubstituted or substituted as defined above. Further useful 7-10 membered heterocyclo groups include endo-8-tert-butoxycarbonyl-8-azabicyclo[3.2.1]octan-3-yl, 8-methyl-8-azabicyclo[3.2.1]octan-3-yl, and endo-9-methyl-9-azabicyclo[3.3.1]nonan-3-yl. In one embodiment, $R^6$ is any heterocycloalkyl as defined above and $R^5$ is H. In another embodiment, $R^6$ is any heterocycloalkyl as defined above and $R^5$ is $NH_2$. In another embodiment, $R^6$ is any heterocycloalkyl as defined above and $R^5$ is $C_{1-4}$ alkyl.

In another embodiment, Compounds of the Invention are compounds of Formula I, wherein G is $G^1$, and where $R^6$ in $G^1$ is heterocyclo($C_{1-4}$)alkyl, wherein the heterocyclo is selected from the group consisting of pyrrolidinyl, imidazolidinyl, piperidinyl, and piperazinyl, any of which is unsubstituted or substituted with one or more substituents, typically 1, 2 or 3 substituents, selected from the group consisting of alkyl, hydroxy, hydroxyalkyl, cyano, aminocarbonyl, carboxy and alkoxycarbonyl, and $R^5$ is as defined above for Formula I. In one embodiment, $R^5$ is H. In another embodiment, Compounds of the Invention are compounds of Formula I, wherein G is $G^1$, and where $R^6$ in $G^1$ is 2-oxo-imidazolidin-1-yl($C_{1-4}$ alkyl, as specifically 3-(2-oxo-imidazolidin-1-yl)propyl. In another embodiment, Compounds of the Invention are compounds of Formula I, wherein G is $G^1$, which is selected from the group consisting of

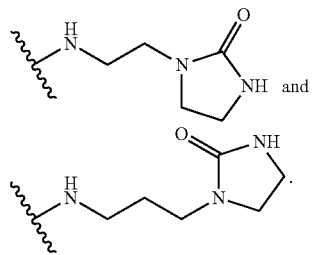

In another embodiment, Compounds of the Invention are compounds of Formula I, wherein G is $G^1$, and where $R^5$ and $R^6$ together with the nitrogen atom form a 5- or 6-membered heterocyclic ring having carbon atoms and 1 or 2 nitrogen atoms, wherein the heterocyclic ring is unsubstituted or substituted with one or more substituents, typically 1, 2 or 3 substituents, each independently selected from the group consisting of oxo, alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano. Useful substituents on the heterocyclic ring include oxo, $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, amino, amino($C_{1-6}$)alkyl, $C_{1-4}$ alkylamino($C_{1-6}$)alkyl, di($C_{1-4}$alkylamino($C_{1-6}$)alkyl, aminocarbonyl, carboxy, $C_{1-6}$ alkoxycarbonyl, and cyano; and preferably oxo, $C_{1-4}$ alkyl, $C_{1-4}$ alkoxy, halogen, halo($C_{1-4}$alkyl, halo($C_{1-4}$)alkoxy, hydroxy, hydroxy($C_{1-4}$alkyl, amino, amino($C_{1-4}$)alkyl, $C_{1-2}$ alkylamino($C_{1-4}$)alkyl, di($C_{1-2}$)alkylamino($C_{1-4}$)alkyl, aminocarbonyl, carboxy, $C_{1-4}$ alkoxycarbonyl, and cyano. In one embodiment, $R^5$ and $R^6$ together with the nitrogen atom form a 5-membered heterocyclic ring having carbon atoms and 1 or 2 nitrogen atoms, such as for example, pyrrolidin-1-yl or imidazolidin-1-yl, wherein the heterocyclic ring is unsubstituted or substituted as defined above. In another embodiment, $R^5$ and $R^6$ together with the nitrogen atom form a 6-membered heterocyclic ring having carbon atoms and 1 or 2 nitrogen atoms, such as for example piperidin-1-yl or piperazin-1-yl, wherein the heterocyclic ring is unsubstituted or substituted as defined above.

In another embodiment, Compounds of the Invention are compounds of Formula I, wherein G is $G^1$ having the structure:

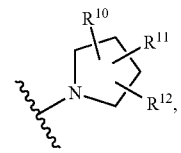

wherein $R^{10}$, $R^{11}$, and $R^{12}$ are each independently selected from the group consisting of hydrogen, oxo, $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$)alkyl, amino, amino($C_{1-4}$)alkyl, $C_{1-2}$ alkylamino($C_{1-4}$alkyl, di($C_{1-2}$)alkylamino($C_{1-4}$)alkyl, aminocarbonyl, carboxy, $C_{1-4}$ alkoxycarbonyl, and cyano; and typically each independently selected from the group consisting of hydrogen, oxo, methyl, ethyl, propyl, isopropyl, fluoro, chloro, bromo, trifluoromethyl, trifluoromethoxy, hydroxy, hydroxymethyl, 2-hydroxyethyl, 3-hydroxypropyl, amino, dimethylamino, diethylamino, methylaminomethyl, methylaminoethyl, dimethylaminomethyl, dimethylaminoethyl, aminocarbonyl, carboxy, cyano, methoxycarbonyl, and ethoxycarbonyl.

In another embodiment, Compounds of the Invention are compounds of Formula I, wherein G is $G^1$ and $G^1$ is selected from the group consisting of (i)
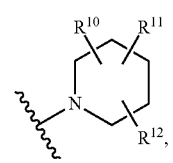

(ii)
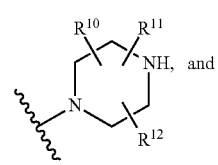

(iii)
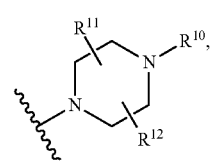

wherein $R^{10}$, $R^{11}$ and $R^{12}$ are each independently selected from the group consisting of hydrogen, oxo, $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$)alkyl, amino, amino($C_{1-4}$)alkyl, $C_{1-2}$ alkylamino($C_{1-4}$)alkyl, di($C_{1-2}$)alkylamino($C_{1-4}$)alkyl, aminocarbonyl, carboxy, $C_{1-4}$ alkoxycarbonyl, and cyano; and typically each independently selected from the group consisting of hydrogen, oxo, methyl, ethyl, propyl, isopropyl, fluoro, chloro, bromo, trifluoromethyl, trifluoromethoxy, hydroxy, hydroxymethyl, 2-hydroxyethyl, 3-hydroxypropyl, amino, dimethylamino, diethylamino, methylaminomethyl, methylaminoethyl, dimethylaminomethyl, dimethylaminoethyl, aminocarbonyl, carboxy, cyano, methoxycarbonyl, and ethoxycarbonyl, provided that when $G^1$ is (iii), then $R^{10}$ is other than hydrogen.

In another embodiment, Compounds of the Invention are compounds of Formula I, wherein G is $G^1$, where $R^5$ and $R^6$ together with the nitrogen atom to which they are attached form a heterocyclic ring selected from the group consisting of pyrrolidinyl, imidazolidinyl, piperidinyl, and piperazinyl, which is unsubstituted or substituted with 1 or 2 substituents each independently selected from the group consisting of oxo, alkyl, hydroxy, hydroxyalkyl, cyano, aminocarbonyl, carboxy and alkoxycarbonyl; preferably each independently selected from the group consisting of oxo, $C_{1-4}$ alkyl, hydroxy, hydroxy($C_{1-4}$)alkyl, cyano, aminocarbonyl, carboxy and $C_{1-4}$ alkoxycarbonyl; and more preferably each independently selected from the group consisting of oxo, methyl, ethyl, propyl, iso-propyl, hydroxy, hydroxymethyl, 2-hydroxyethyl, 3-hydroxypropyl, aminocarbonyl, methoxycarbonyl, and ethoxycarbonyl.

In another embodiment, Compounds of the Invention are compounds of Formula I, wherein G is $G^1$, and where $G^1$ is selected from the group consisting of

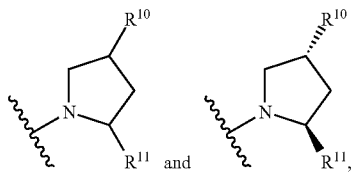

wherein $R^{10}$ and $R^{11}$ are each independently selected from the group consisting of oxo, alkyl, hydroxy, hydroxyalkyl, cyano, aminocarbonyl, carboxy and alkoxycarbonyl; preferably each independently selected from the group consisting of oxo, $C_{1-4}$ alkyl, hydroxy, hydroxy($C_{1-4}$)alkyl, cyano, aminocarbonyl, carboxy and $C_{1-4}$ alkoxycarbonyl; and more preferably each independently selected from the group consisting of oxo, methyl, ethyl, propyl, iso-propyl, hydroxy, hydroxymethyl, 2-hydroxyethyl, 3-hydroxypropyl, aminocarbonyl, methoxycarbonyl, and ethoxycarbonyl. In one embodiment, $R^{10}$ is hydrogen or hydroxy and $R^{11}$ is as defined above. In another embodiment, $R^{10}$ is hydrogen or hydroxy and $R^{11}$ is selected from the group consisting of aminocarbonyl and $C_{1-4}$ alkoxycarbonyl.

In another embodiment, Compounds of the Invention are compounds of Formula I, wherein G is $G^1$, and where $G^1$ is

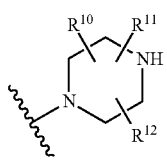

wherein $R^{10}$ and $R^{11}$ are both hydrogen and $R^{12}$ is selected from the group consisting of oxo, alkyl, hydroxy, hydroxyalkyl, cyano, aminocarbonyl, carboxy and alkoxycarbonyl; preferably each independently selected from the group consisting of oxo, $C_{1-4}$ alkyl, hydroxy, hydroxy($C_{1-4}$alkyl, cyano, aminocarbonyl, carboxy and $C_{1-4}$ alkoxycarbonyl; and more preferably each independently selected from the group consisting of oxo, methyl, ethyl, propyl, iso-propyl, hydroxy, hydroxymethyl, 2-hydroxyethyl, 3-hydroxypropyl, aminocarbonyl, methoxycarbonyl, and ethoxycarbonyl. In another embodiment, $R^{12}$ is oxo. In another embodiment, $G^1$ is 3-oxo-piperazinyl.

In another embodiment, Compounds of the Invention are compounds of Formula I, wherein G is $G^1$, and where $G^1$ is selected from the group consisting of

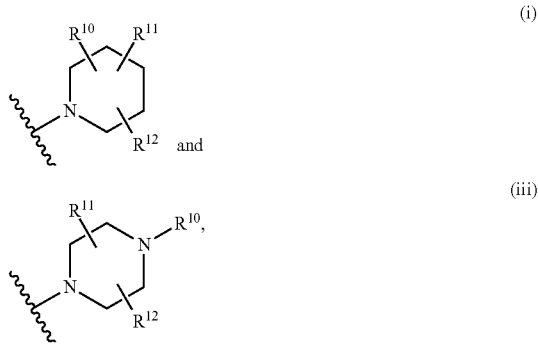

wherein $R^{11}$ and $R^{12}$ are both hydrogen and $R^{10}$ is selected from the group consisting of oxo, alkyl, hydroxy, hydroxyalkyl, cyano, aminocarbonyl, carboxy and alkoxycarbonyl; preferably each independently selected from the group consisting of oxo, $C_{1-4}$ alkyl, hydroxy, hydroxy($C_{1-4}$)alkyl, cyano, aminocarbonyl, carboxy and $C_{1-4}$ alkoxycarbonyl; and more preferably each independently selected from the group consisting of oxo, methyl, ethyl, propyl, iso-propyl, hydroxy, hydroxymethyl, 2-hydroxyethyl, 3-hydroxypropyl, aminocarbonyl, methoxycarbonyl, and ethoxycarbonyl. In one embodiment, $G^1$ is (i) and $R^{10}$ is at the 4-position of the piperidinyl ring.

In another embodiment, Compounds of the Invention are compounds of Formula I, where G is $G^2$:

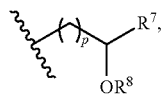

wherein p, $R^7$, and $R^8$ are as defined above for Formula I.

In another embodiment, Compounds of the Invention are compounds of Formula I, wherein G is $G^2$, and where $R^7$ in $G^2$ is —$(CH_2)_q$OH, wherein q is 0, 1, 2, 3, 4, or 5, and $R^8$ is as defined above. Typically, q is 0, 1, 2, or 3. More typically, q is 0, 1 or 2, and specifically q is 0 or 1. In one embodiment, $R^7$ is —$(CH_2)_q$OH as defined above and $R^8$ is hydrogen. In another embodiment, $R^7$ is —$(CH_2)_q$OH as defined above and $R^8$ is a bond.

In another embodiment, Compounds of the Invention are compounds of Formula I, wherein G is $G^2$, and where $R^7$ in $G^2$ is hydrogen, amino, alkylamino, dialkylamino or alkoxy. In one embodiment, $R^7$ in $G^2$ is hydrogen. In another embodiment, $R^7$ in $G^2$ is amino. In another embodiment, $R^7$ in $G^2$ is alkylamino, preferably $C_{1-6}$ alkylamino, more preferably $C_{1-4}$ alkylamino, such as methylamino, ethylamino, propylamino, and butylamino. In another embodiment, $R^7$ in $G^2$ is dialkylamino, preferably di($C_{1-6}$)alkylamino, and more preferably di($C_{1-4}$)alkylamino, such as dimethylamino, ethylmethylamino, diethylamino, methylpropylamino, ethylpropylamino, and dipropylamino. In another embodiment, $R^7$ in $G^2$ is alkoxy, preferably $C_{1-6}$ alkoxy, and more preferably $C_{1-4}$ alkoxy, such as methoxy, ethoxy, propoxy, isopropoxy, butoxy, and tert-butoxy.

In another embodiment, Compounds of the Invention are compounds of Formula I, wherein G is $G^2$, and where $R^8$ in $G^2$ is hydrogen.

In another embodiment, Compounds of the Invention are compounds of Formula I, wherein G is $G^2$, and where $R^8$ in $G^2$ is a bond (—$OR^8$ is =O).

In another embodiment, Compounds of the Invention are compounds of Formula I, wherein G is $G^2$, and where $G^2$ is selected from the group consisting of

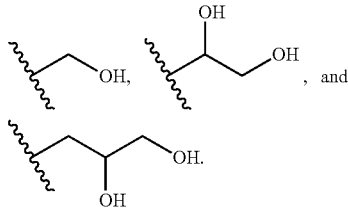

In another embodiment, Compounds of the Invention are compounds of Formula I, wherein G is $G^2$, and where $G^2$ is selected from the group consisting of

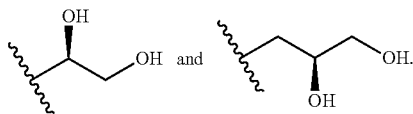 [SMILES: *[C@@H](O)CO ; *C[C@H](O)CO]

In another embodiment, Compounds of the Invention are compounds of Formula I, wherein G is $G^2$, and where $G^2$ is selected from the group consisting of

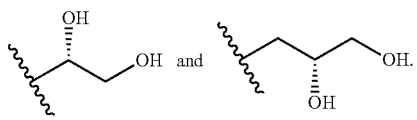 [SMILES: *[C@H](O)CO ; *C[C@@H](O)CO]

In another embodiment, Compounds of the Invention are compounds of Formula I, wherein G is $G^2$, and where $G^2$ is —C(=O)$NH_2$.

In another embodiment, Compounds of the Invention are compounds of Formula I, wherein G is $G^2$, and where $G^2$ is —C(=O)OH or —C(=O)O($C_{1-4}$)alkyl, such as for example, —C(=O)$OCH_3$, —C(=O)$OCH_2CH_3$, or —C(=O)$OCH_2CH_2CH_3$.

In another embodiment, Compounds of the Invention are compounds of Formula I, where G is $G^3$, that is a 5- or 6-membered heteroaryl containing at least one nitrogen atom, wherein the heteroaryl is unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, acyloxy, and cyano. Useful substituents for the heteroaryl group include $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, amino, amino($C_{1-6}$)alkyl, $C_{1-4}$ alkylamino($C_{1-6}$)alkyl, di($C_{1-4}$)alkylamino($C_{1-6}$)alkyl, aminocarbonyl, carboxy, $C_{1-6}$ acyloxy, and cyano; and preferably $C_{1-4}$ alkyl, $C_{1-4}$ alkoxy, halogen, halo($C_{1-4}$)alkyl, halo($C_{1-4}$) alkoxy, hydroxy, hydroxy($C_{1-4}$alkyl, amino, amino($C_{1-4}$) alkyl, $C_{1-2}$ alkylamino($C_{1-4}$)alkyl, di($C_{1-2}$)alkylamino($C_{1-4}$) alkyl, aminocarbonyl, carboxy, $C_{1-4}$ acyloxy, and cyano. Useful 5- and 6-membered heteroaryl groups include 5- and 6-membered heteroaryl groups having at least one nitrogen atom, such as pyrrolyl (e.g., 1H-pyrrol-2-yl and 1H-pyrrol-3-yl), imidazolyl (e.g., 1H-imidazol-2-yl, 1H-imidazol-4-yl, 1H-imidazol-5-yl, 2H-imidazol-2-yl, and 2H-imidazol-4-yl), 1,2,3-triazolyl (e.g., 1H-1,2,3-triazol-2-yl, 1H-1,2,3-triazol-4-yl, and 1H-1,2,3-triazol-5-yl), 1,2,4-triazolyl (e.g., 1H-1,2,4-triazol-3-yl and 1H-1,2,4-triazol-5-yl), thiazolyl (e.g., thiazol-2-yl, thiazol-4-yl, and thiazol-5-yl), oxazolyl (e.g., oxazol-2-yl, oxazol-4-yl, and oxazol-5-yl), isooxazolyl (e.g., isoxazol-3-yl, isoxazol-4-yl, and isoxazol-5-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), pyridazinyl (e.g., pyridazin-3-yl or pyridazin-4-yl), and pyrazinyl (e.g., pyrazin-2-yl and pyrazin-3-yl), which can be unsubstituted or substituted as defined above.

In another embodiment, Compounds of the Invention are compounds of Formula I, wherein G is $G^3$, and where $G^3$ is pyridinyl (pyridin-2-yl, pyridin-3-yl, or pyridin-4-yl), unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, acyloxy, and cyano; and preferably each independently selected from the group consisting of $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, amino, amino($C_{1-6}$)alkyl, $C_{1-4}$ alkylamino($C_{1-6}$)alkyl, di($C_{1-4}$)alkylamino($C_{1-6}$)alkyl, aminocarbonyl, carboxy, $C_{1-6}$ acyloxy, and cyano; and more preferably each independently selected from the group consisting of $C_{1-4}$ alkyl, $C_{1-4}$ alkoxy, halogen, halo($C_{1-4}$alkyl, halo($C_{1-4}$) alkoxy, hydroxy, hydroxy($C_{1-4}$alkyl, amino, amino($C_{1-4}$) alkyl, $C_{1-2}$ alkylamino($C_{1-4}$)alkyl, di($C_{1-2}$)alkylamino($C_{1-4}$) alkyl, aminocarbonyl, carboxy, $C_{1-4}$ acyloxy, and cyano. In another embodiment, Compounds of the Invention are compounds of Formula I, wherein G is $G^3$ and $G^3$ is pyridin-2-yl, pyridin-3-yl or pyridin-4-yl substituted with cyano or aminocarbonyl.

In another embodiment, Compounds of the Invention are compounds of Formula I, where G is $G^4$, and $G^4$ is —$OR^9$, wherein $R^9$ is alkyl, alkenyl, alkynyl, hydroxyalkyl, aminoalkyl, alkylaminoalkyl, dialkylaminoalkyl, aminocarbonylalkyl, carboxyalkyl, alkoxycarbonylalkyl, arylalkyl, heteroarylalkyl, aryl or heteroaryl, wherein said aryl or heteroaryl group is unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, acyloxy, and cyano. In one embodiment, $R^9$ is alkyl, preferably $C_{1-6}$ alkyl, and more preferably $C_{1-4}$ alkyl, such as methyl, ethyl, propyl, isopropyl, butyl, and tert-butyl. In another embodiment, $R^9$ is aryl, preferably $C_{6-14}$ aryl, and more preferably $C_{6-12}$ aryl, such as phenyl, naphthyl and biphenyl, unsubstituted or substituted with one or more, preferably 1 or 2, substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, acyloxy, and cyano. In another embodiment, $R^9$ is heteroaryl, preferably 5- or 6-membered heteroaryl containing at least one nitrogen atom, unsubstituted or substituted with one or more substituents, typically 1, 2 or 3 substituents, each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, acyloxy, and cyano. Useful 5- or 6-membered heteroaryl groups having at least one nitrogen atom include pyrrolyl (e.g., 1H-pyrrol-2-yl and 1H-pyrrol-3-yl), imidazolyl (e.g., 1H-imidazol-2-yl, 1H-imidazol-4-yl, 1H-imidazol-5-yl, 2H-imidazol-2-yl, and 2H-imidazol-4-yl), 1,2,3-triazolyl (e.g., 1H-1,2,3-triazol-2-yl, 1H-1,2,3-triazol-4-yl, and 1H-1,2,3-triazol-5-yl), 1,2,4-triazolyl (e.g., 1H-1,2,4-triazol-3-yl and 1H-1,2,4-triazol-5-yl), thiazolyl (e.g., thiazol-2-yl, thiazol-4-yl, and thiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), pyridazinyl (e.g., pyridazin-3-yl or pyridazin-4-yl), and pyrazinyl (e.g., pyrazin-2-yl and pyrazin-3-yl), which can be unsubstituted or substituted as defined above. Useful substituents for the aryl and heteroaryl groups include $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, amino, amino($C_{1-6}$)alkyl, $C_{1-4}$ alkylamino($C_{1-6}$)alkyl, di($C_{1-4}$ alkylamino($C_{1-6}$)alkyl, aminocarbonyl, carboxy, $C_{1-6}$ acyloxy, and cyano; and preferably $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$)alkyl, amino, amino($C_{1-4}$)alkyl, $C_{1-2}$ alkylamino($C_{1-4}$)alkyl, di($C_{1-2}$)alkylamino($C_{1-4}$)alkyl, aminocarbonyl, carboxy, $C_{1-4}$ acyloxy, and cyano.

In another embodiment, Compounds of the Invention are compounds of Formula I, wherein G is $G^4$, and where $G^4$ is unsubstituted pyridin-2-yloxy, pyridin-3-yloxy or pyridin-4-yloxy.

In another embodiment, Compounds of the Invention are compounds of Formula I, where $A^1$ is an optionally substituted heteroaryl. In one embodiment, $A^1$ is a 5-6 membered heteroaryl ring having at least one nitrogen atom. Typical heteroaryl groups for $A^1$ include 6-membered heteroaryl groups having at least one nitrogen atom, such as pyridyl (pyridin-2-yl, pyridin-3-yl, or pyridin-4-yl), pyrimidinyl (pyrimidin-2-yl, pyrimidin-4-yl, pyrimidin-5-yl, or pyrimidin-6-yl), pyridazinyl (pyridazin-3-yl, pyridazin-4-yl, pyridazin-5-yl, or pyridazin-6-yl), and pyrazinyl (pyrazin-2-yl or pyrazin-3-yl). In another embodiment, Compounds of the Invention are compounds of Formula I, where $A^1$ is unsubstituted or substituted pyridyl, such as pyridin-2-yl, pyridin-3-yl, or pyridin-4-yl. In another embodiment, $A^1$ is pyridin-2-yl, pyridin-3-yl or pyridin-4-yl optionally substituted with 1 or 2 substituents each independently selected from the group consisting of alkyl (for example, $C_{1-4}$ alkyl, such as methyl or ethyl), haloalkyl (for example, halo($C_{1-4}$)alkyl, such as trifluoromethyl) and halogen.

In another embodiment, Compounds of the Invention are compounds of Formula I, where $A^1$ is an optionally substituted aryl. In one embodiment, $A^1$ is unsubstituted phenyl. In another embodiment, $A^1$ is phenyl substituted with 1, 2, or 3 substituents each independently selected from the group consisting of alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl; preferably each substituent is independently selected from the group consisting of $C_{1-6}$ alkyl, $C_{2-6}$ alkenyl, $C_{2-6}$ alkynyl, halogen, halo($C_{1-6}$)alkyl, hydroxy($C_{1-6}$)alkyl, hydroxy, nitro, amino, cyano, amide, carboxy($C_{1-6}$)alkyl, $C_{1-4}$ alkoxy($C_{1-6}$) alkyl, ureido, $C_{1-6}$ acylamino, thiol, $C_{1-6}$ acyloxy, azido, mercapto($C_{1-6}$)alkyl, $C_{1-6}$ alkoxy, carboxy, and aminocarbonyl; and more preferably each substituent is independently selected from the group consisting of $C_{1-4}$ alkyl, $C_{2-4}$ alkenyl, $C_{2-4}$ alkynyl, halogen, halo($C_{1-4}$)alkyl, hydroxy($C_{1-4}$alkyl, hydroxy, nitro, amino, cyano, amide, carboxy($C_{1-4}$)alkyl, $C_{1-2}$ alkoxy($C_{1-4}$)alkyl, ureido, $C_{1-4}$ acylamino, thiol, $C_{1-4}$ acyloxy, azido, mercapto($C_{1-4}$alkyl, $C_{1-4}$ alkoxy, carboxy, and aminocarbonyl. Typically, the 1, 2, or 3 substituents are each independently selected from the group consisting of $C_{1-4}$ alkyl, halogen, halo($C_{1-4}$)alkyl, hydroxy($C_{1-4}$alkyl, hydroxy, nitro, amino, cyano, and $C_{1-4}$ alkoxy, and more typically are each independently selected from the group consisting of fluoro, bromo, trifluoromethyl, and cyano. In one embodiment, $A^1$ is phenyl substituted at the 4-position. In this embodiment, the substituent is typically halogen, cyano, or haloalkyl, such as trihaloalkyl, and specifically trifluoromethyl. In one embodiment, $A^1$ is phenyl substituted with two substituents, which can be the same or different, at the 3- and 4-positions. In this embodiment, the two substituents are independently selected from the group consisting of halogen, cyano and haloalkyl (such as trihaloalkyl, and specifically trifluoromethyl). In one embodiment, $A^1$ is phenyl substituted with cyano and trifluoromethyl at the 3- and 4-positions of the phenyl group, respectively.

In another embodiment, Compounds of the Invention are compounds of Formula I, where X is —O—, —S—, or —SO$_2$—. Typical compounds of the present invention include those where X is —O— or —S—. In another embodiment, Compounds of the Invention are those where X is —O—.

In another embodiment, Compounds of the Invention are compounds of Formula I, wherein A is A' having the structure:

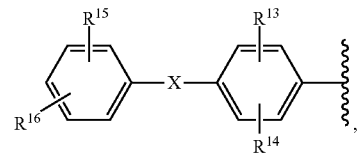

wherein
X is —O—, —S—, —SO—, —SO$_2$—, —CH$_2$—, or —NH—; and $R^{13}$, $R^{14}$, $R^{15}$, and $R^{16}$ are each independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl; preferably each of $R^{13}$, $R^{14}$, $R^{15}$, and $R^{16}$ is independently selected from the group consisting of $C_{1-6}$ alkyl, $C_{2-6}$ alkenyl, $C_{2-6}$ alkynyl, halogen, halo($C_{1-6}$)alkyl, hydroxy($C_{1-6}$)alkyl, hydroxy, nitro, amino, cyano, amide, carboxy($C_{1-6}$)alkyl, $C_{1-4}$ alkoxy($C_{1-6}$)alkyl, ureido, $C_{1-6}$ acylamino, thiol, $C_{1-6}$ acyloxy, azido, mercapto($C_{1-6}$)alkyl, $C_{1-6}$ alkoxy, carboxy, and aminocarbonyl; and more preferably each of $R^{13}$, $R^{14}$, $R^{15}$, and $R^{16}$ is independently selected from the group consisting of $C_{1-4}$ alkyl, $C_{2-4}$ alkenyl, $C_{2-4}$ alkynyl, halogen, halo($C_{1-4}$)alkyl, hydroxy($C_{1-4}$)alkyl, hydroxy, nitro, amino, cyano, amide, carboxy($C_{1-4}$alkyl, $C_{1-2}$ alkoxy($C_{1-4}$) alkyl, ureido, $C_{1-4}$ acylamino, thiol, $C_{1-4}$ acyloxy, azido, mercapto($C_{1-4}$alkyl, $C_{1-4}$ alkoxy, carboxy, and aminocarbonyl. Typically, $R^{13}$, $R^{14}$, $R^{15}$ and $R^{16}$ are each independently selected from the group consisting of hydrogen, $C_{1-4}$ alkyl, halogen, halo($C_{1-4}$)alkyl, hydroxy($C_{1-4}$alkyl, hydroxy, nitro, amino, cyano, and $C_{1-4}$ alkoxy. More typically, $R^{13}$, $R^{14}$, $R^{15}$ and $R^{16}$ are each independently selected from the group consisting of hydrogen, fluoro, bromo, trifluoromethyl, and cyano. In this aspect of the invention, compounds useful in the present invention are those where X is —O— or —S—. In one embodiment, $R^{13}$ and $R^{14}$ are both hydrogen and $R^{15}$ and $R^{16}$ are as defined above.

In another embodiment, Compounds of the invention are compounds of Formula I, wherein A is A″ having the structure:

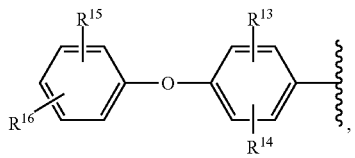

wherein
$R^{13}$, $R^{14}$, $R^{15}$, and $R^{16}$ are each independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl; preferably each of $R^{13}$, $R^{14}$, $R^{15}$, and $R^{16}$ is independently selected from the group consisting of $C_{1-6}$ alkyl, $C_{2-6}$ alkenyl, $C_{2-6}$ alkynyl, halogen, halo($C_{1-6}$)alkyl, hydroxy($C_{1-6}$)alkyl, hydroxy, nitro, amino, cyano, amide, carboxy($C_{1-6}$)alkyl, $C_{1-4}$ alkoxy($C_{1-6}$)alkyl, ureido, $C_{1-6}$ acylamino, thiol, $C_{1-6}$ acyloxy, azido, mercapto($C_{1-6}$)alkyl, $C_{1-6}$ alkoxy, carboxy, and aminocarbonyl; and more preferably each of $R^{13}$, $R^{14}$, $R^{15}$, and $R^{16}$ is independently selected from the group consisting of $C_{1-4}$ alkyl, $C_{2-4}$ alkenyl, $C_{2-4}$ alkynyl, halogen, halo($C_{1-4}$)alkyl, hydroxy($C_{1-4}$alkyl, hydroxy, nitro, amino, cyano, amide, carboxy($C_{1-4}$alkyl, $C_{1-2}$ alkoxy($C_{1-4}$ alkyl, ureido, $C_{1-4}$ acylamino, thiol, $C_{1-4}$ acyloxy, azido, mercapto($C_{1-4}$alkyl, $C_{1-4}$ alkoxy, carboxy, and aminocarbonyl. Typically, $R^{13}$, $R^{14}$, $R^{15}$ and $R^{16}$ are as defined above for A′. In one embodiment, $R^{13}$ and $R^{14}$ are both hydrogen and $R^{15}$ and $R^{16}$ are as defined above.

In another embodiment, Compounds of the Invention are compounds of Formula I, where A is A″ and $R^1$-$R^4$ are hydrogen, which Compounds of the Invention have the Formula II:

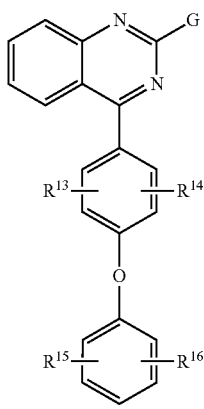

and the pharmaceutically acceptable salts, prodrugs, and solvates thereof, wherein G is as defined in connection with Formula I, and $R^{13}$, $R^{14}$, $R^{15}$, and $R^{16}$ are each independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl. Preferable definitions for $R^{13}$, $R^{14}$, $R^{15}$ and $R^{16}$ are those described above in connection with Formula I.

In another embodiment, Compounds of the Invention are compounds of Formula I, where A is A″, $R^1$-$R^4$ are each hydrogen, and G is $G^1$, which Compounds of the Invention have the Formula III:

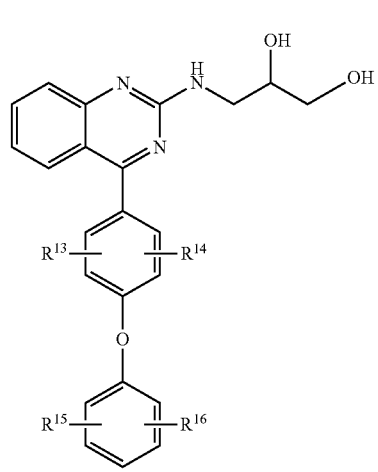

and the pharmaceutically acceptable salts, prodrugs, and solvates thereof, wherein $R^{13}$, $R^{14}$, $R^{15}$ and $R^{16}$ are as defined above for Formula I or II. Preferable definitions for $R^{13}$, $R^{14}$, $R^{15}$ and $R^{16}$ are those described above in connection with Formula I or II.

In another embodiment, Compounds of the Invention are compounds of Formula I, where A is A″, $R^1$-$R^4$ are hydrogen, and G is $G^1$, which Compounds of the Invention have the Formula IV:

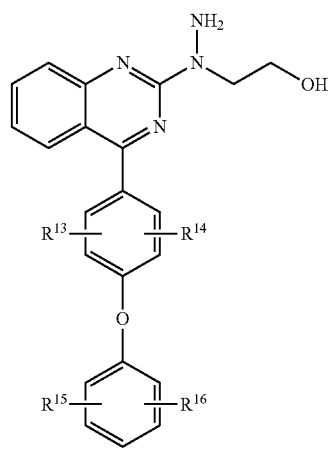

and the pharmaceutically acceptable salts, prodrugs, and solvates thereof, wherein $R^{13}$, $R^{14}$, $R^{15}$, and $R^{16}$ are as defined in connection with Formula II.

In another embodiment, Compounds of the Invention are compounds of Formula I, where A is A'', $R^1$-$R^4$ are hydrogen, and G is $G^2$, which Compounds of the Invention have the Formula V:

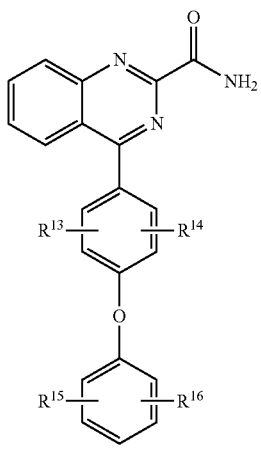

and the pharmaceutically acceptable salts, prodrugs, and solvates thereof, wherein $R^{13}$, $R^{14}$, $R^{15}$, and $R^{16}$ are as defined in connection with Formula I or II.

In another embodiment, Compounds of the Invention include compounds of any of Formulae II-V, where $R^{13}$ and $R^{14}$ are both hydrogen and $R^{15}$ and $R^{16}$ are each independently selected from the group consisting of hydrogen, alkyl, alkenyl, alkynyl, halogen, haloalkyl, hydroxyalkyl (including monohydroxyalkyl and dihydroxyalkyl), hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl. Typically, $R^{15}$ and $R^{16}$ are each independently selected from the group consisting of hydrogen, $C_{1-4}$ alkyl, halogen, halo($C_{1-4}$)alkyl, hydroxy($C_{1-4}$)alkyl, hydroxy, nitro, amino, cyano, $C_{1-4}$ alkoxy, and carboxy, and more typically $R^{15}$ and $R^{16}$ are each independently selected from the group consisting of hydrogen, fluoro, bromo, trifluoromethyl, and cyano. In one embodiment, $R^{13}$, $R^{14}$, $R^5$, and $R^{16}$ each are hydrogen. In another embodiment, $R^{13}$, $R^{14}$ and $R^{15}$ are hydrogen and $R^{16}$ is alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, or aminocarbonyl; preferably $R^{16}$ is $C_{1-6}$ alkyl, $C_{2-6}$ alkenyl, $C_{2-6}$ alkynyl, halogen, halo($C_{1-6}$)alkyl, hydroxy ($C_{1-6}$)alkyl, hydroxy, nitro, amino, cyano, amide, carboxy ($C_{1-6}$)alkyl, $C_{1-4}$ alkoxy($C_{1-6}$)alkyl, ureido, $C_{1-6}$ acylamino, thiol, $C_{1-6}$ acyloxy, azido, mercapto($C_{1-6}$)alkyl, $C_{1-6}$ alkoxy, carboxy, or aminocarbonyl; and more preferably $R^{16}$ is $C_{1-4}$ alkyl, $C_{2-4}$ alkenyl, $C_{2-4}$ alkynyl, halogen, halo($C_{1-4}$)alkyl, hydroxy($C_{1-4}$alkyl, hydroxy, nitro, amino, cyano, amide, carboxy($C_{1-4}$)alkyl, $C_{1-2}$ alkoxy($C_{1-4}$)alkyl, ureido, $C_{1-4}$ acylamino, thiol, $C_{1-2}$ acyloxy, azido, mercapto($C_{1-4}$alkyl, $C_{1-4}$ alkoxy, carboxy, or aminocarbonyl. Typically, $R^{16}$ is selected from the group consisting of hydrogen, $C_{1-4}$ alkyl, halogen, halo($C_{1-4}$)alkyl, hydroxy($C_{1-4}$alkyl, hydroxy, nitro, amino, cyano, and $C_{1-4}$ alkoxy. More typically, $R^{16}$ is selected from the group consisting of hydrogen, fluoro, bromo, trifluoromethyl, and cyano. In one embodiment, $R^{16}$ is at the 4-position of the phenyl ring (i.e., at the para-position). In this embodiment, the substituent is typically halogen, specifically fluoro, cyano, or haloalkyl, such as trihaloalkyl, and specifically trifluoromethyl. In one embodiment, $R^{13}$ and $R^{14}$ are both hydrogen and $R^{15}$ and $R^{16}$, which can be the same or different, are at the 3- and 4-positions of the phenyl ring (i.e., at the meta- and para-positions). In this embodiment, $R^{15}$ and $R^{16}$ are typically independently selected from the group consisting of halogen, cyano and haloalkyl (such as trihaloalkyl, and specifically trifluoromethyl).

In another embodiment, Compounds of the Invention are compounds of Formula I, where $R^1$, $R^2$, $R^3$, and $R^4$ are each independently selected from the group consisting of hydrogen, $C_{1-6}$ alkyl, $C_{2-6}$ alkenyl, $C_{2-6}$ alkynyl, halogen, hydroxy, hydroxy($C_{1-6}$)alkyl, halo($C_{1-6}$)alkyl, cyano, amino, $C_{1-6}$ alkylamino, di($C_{1-6}$)alkylamino, $C_{1-6}$ alkoxy, aminocarbonyl, $C_{1-6}$ alkylaminocarbonyl, di($C_{1-6}$)alkylaminocarbonyl, $C_{1-6}$ alkylcarbonylamino, $C_{1-6}$ alkylcarbonyloxy, carboxy, aminosulfonyl, $C_{1-6}$ alkylsulfonylamino, ($C_{1-6}$ alkylsulfonylamino)($C_{1-6}$)alkyl, ureido, (aminocarbonyl)($C_{1-6}$)alkylamino, and (carboxy($C_{1-6}$)alkyl)amino; more preferably each is independently selected from the group consisting of hydrogen, $C_{1-4}$ alkyl, $C_{2-4}$ alkenyl, $C_{2-4}$ alkynyl, halogen, hydroxy, hydroxy($C_{1-4}$)alkyl, halo($C_{1-4}$)alkyl, cyano, amino, $C_{1-4}$ alkylamino, di($C_{1-4}$)alkylamino, $C_{1-4}$ alkoxy, aminocarbonyl, $C_{1-4}$ alkylamino carbonyl, di($C_{1-4}$)alkylaminocarbonyl, $C_{1-4}$ alkylcarbonylamino, $C_{1-4}$ alkylcarbonyloxy, carboxy, aminosulfonyl, $C_{1-4}$ alkylsulfonylamino, ($C_{1-4}$ alkylsulfonylamino)($C_{1-4}$)alkyl, ureido, (aminocarbonyl)($C_{1-4}$)alkylamino, and (carboxy($C_{1-4}$)alkyl)amino; and more preferably each is independently selected from the group consisting of hydrogen, $C_{1-4}$ alkyl, $C_{2-4}$ alkenyl, $C_{2-4}$ alkynyl, halogen, hydroxy, hydroxy($C_{1-4}$)alkyl, halo($C_{1-2}$)alkyl, cyano, amino, $C_{1-2}$ alkylamino, di($C_{1-2}$)alkylamino, $C_{1-2}$ alkoxy, aminocarbonyl, $C_{1-2}$ alkylaminocarbonyl, di($C_{1-2}$) alkylaminocarbonyl, $C_{1-2}$ alkylcarbonylamino, $C_{1-2}$ alkylcarbonyloxy, carboxy, aminosulfonyl, $C_{1-2}$ ($C_{1-2}$ alkylsulfonylamino, alkyl sulfonylamino)($C_{1-2}$)alkyl, ureido, (amino carbonyl)($C_{1-2}$)alkylamino, and (carboxy($C_{1-2}$)alkyl)amino.

In another embodiment, Compounds of the Invention are compounds of Formula I, where $R^1$, $R^2$, $R^3$, and $R^4$ are each independently selected from the group consisting of hydrogen, methyl, ethyl, propyl, isopropyl, butyl, —CH(OH) $CH_2OH$, —$CH_2CH(OH)CH_2OH$, carboxy, aminocarbonyl, amino, aminosulfonyl, methylsulfonylamino, ureido, —$NHCH_2COOH$, —$NHCH_2CONH_2$, and —$CH_2NHSO_2Me$. In another embodiment, Compounds of the Invention are compounds of Formula I, where $R^1$, $R^2$, $R^3$, and $R^4$ are each hydrogen.

Optional substituents attached to aryl, phenyl, heteroaryl, cycloalkyl, and heterocyclo rings each take the place of a hydrogen atom that would otherwise be present in any position on the aryl, phenyl, heteroaryl, cycloalkyl and heterocyclo rings, respectively.

In another embodiment, Compounds of the Invention include:

$N^1$-(4-(4-(4-fluorophenoxy)phenyl)quinazolin-2-yl)-$N^2$,$N^2$-dimethylethane-1,2-diamine;

2-((4-(4-(4-fluorophenoxy)phenyl)quinazolin-2-yl)amino) ethanol;

(S)-2-{4-[4-(4-fluorophenoxy)phenyl]quinazolin-2-ylamino}-3-hydroxy-propionamide;

4-(4-(4-(4-fluorophenoxy)phenyl)quinazolin-2-yl)piperazin-2-one;

4-(4-(4-fluorophenoxy)phenyl)quinazolin-2-amine;

(S)-methyl 1-(4-(4-(4-fluorophenoxy)phenyl)-quinazolin-2-yl)-pyrrolidine-2-carboxylate;

4-(4-(4-fluorophenoxy)phenyl)-2-(1-methylhydrazinyl) quinazoline;

2-(4-ethylpiperazin-1-yl)-4-(4-(4-fluorophenoxy)phenyl)
    quinazoline;
1-(4-(4-(4-fluorophenoxy)phenyl)quinazolin-2-yl)piperi-
    din-4-ol;
2-(4-(4-(4-fluorophenoxy)phenyl)quinazolin-2-yl)piper-
    azin-1-yl)ethanol;
4-(4-(4-fluorophenoxy)phenyl)-2-(4-methylpiperazin-1-yl)
    quinazoline;
(S)-1-(4-(4-(4-fluorophenoxy)phenyl)quinazolin-2-yl)pyr-
    rolidine-2-carboxamide;
(2S,4R)-methyl 1-(4-(4-(4-fluorophenoxy)phenyl)quinazo-
    lin-2-yl)-4-hydroxy-pyrrolidine-2-carboxylate;
N-(3-(1H-imidazol-1-yl)propyl)-4-(4-(4-fluorophenoxy)
    phenyl)quinazolin-2-amine;
$N^1$-(4-(4-(4-fluorophenoxy)phenyl)quinazolin-2-yl)-$N^3,N^3$-
    dimethylpropane-1,3-diamine;
4-(4-(4-fluorophenoxy)phenyl)-N-methylquinazolin-2-
    amine;
(R)-3-(4-(4-(4-fluorophenoxy)phenyl)quinazolin-2-yl)
    amino)propane-1,2-diol;
(S)-3-(4-(4-(4-fluorophenoxy)phenyl)quinazolin-2-yl)
    amino)propane-1,2-diol;
(S)-2-((4-(4-(4-fluorophenoxy)phenyl)quinazolin-2-yl)
    amino)succinamide;
4-(4-(4-fluorophenoxy)phenyl)-N-((1R,3S,5S)-9-methyl-9-
    azabicyclo[3.3.1]nonan-3-yl)quinazolin-2-amine;
2-((4-(4-(4-fluorophenoxy)phenyl)quinazolin-2-yl)amino)
    propane-1,3-diol;
1-(2-((4-(4-(4-fluorophenoxy)phenyl)quinazolin-2-yl)
    amino)ethyl)imidazolidin-2-one;
2-(1-(4-(4-(4-fluorophenoxy)phenyl)quinazolin-2-yl)hy-
    drazinyl)ethanol;
2-((4-(4-(4-fluorophenoxy)phenyl)quinazolin-2-yl)amino)
    acetamide;
and the pharmaceutically acceptable salts, prodrugs and solvates thereof.

In another embodiment, Compounds of the Invention include:
4-(4-phenoxyphenyl)quinazoline-2-carboxamide;
ethyl 4-(4-phenoxyphenyl)quinazoline-2-carboxylate;
4-(4-phenoxyphenyl)quinazoline-2-carboxylic acid;
(S)-1-(4-(4-(4-fluorophenoxy)phenyl)quinazolin-2-yl)
    ethane-1,2-diol; and the pharmaceutically acceptable salts, prodrugs and solvates thereof.

In another embodiment, Compounds of the Invention include:
2-ethoxy-4-(4-(4-fluorophenoxy)phenyl)-quinazoline;
4-(4-(4-fluorophenoxy)phenyl)-2-(pyridin-2-yloxy)
    quinazoline;
and the pharmaceutically acceptable salts, prodrugs and solvates thereof.

Useful halo or halogen groups include fluorine, chlorine, bromine and iodine.

Useful alkyl groups are selected from straight-chain and branched-chain $C_{1-10}$ alkyl groups. Typical $C_{1-10}$ alkyl groups include methyl, ethyl, propyl, isopropyl, butyl, sec-butyl, tert-butyl, iso-butyl, 3-pentyl, hexyl, heptyl, octyl, nonyl and decyl, among others. In one embodiment, useful alkyl groups are selected from straight chain $C_{1-6}$ alkyl groups and branched chain $C_{3-6}$ alkyl groups. Typical $C_{1-6}$ alkyl groups include methyl, ethyl, propyl, isopropyl, butyl, sec-butyl, tert-butyl, iso-butyl, pentyl, 3-pentyl, hexyl, among others. In one embodiment, useful alkyl groups are selected from straight chain $C_{2-6}$ alkyl groups and branched chain $C_{3-6}$ alkyl groups. Typical $C_{2-6}$ alkyl groups include ethyl, propyl, isopropyl, butyl, sec-butyl, tert-butyl, iso-butyl, pentyl, 3-pentyl, hexyl, among others. In one embodiment, useful alkyl groups are selected from straight chain $C_{1-4}$ alkyl groups and branched chain $C_{3-4}$ alkyl groups. Typical $C_{1-4}$ alkyl groups include methyl, ethyl, propyl, isopropyl, butyl, sec-butyl, tert-butyl, iso-butyl.

Useful cycloalkyl groups are selected from saturated and partially unsaturated (containing one or two double bonds) cyclic hydrocarbon groups containing one to three rings having from three to twelve carbon atoms (i.e., $C_3$-$C_{12}$ cycloalkyl) or the number of carbons designated. In one embodiment, the cycloalkyl has one or two rings. In another embodiment, the cycloalkyl is a $C_3$-$C_8$ cycloalkyl. Exemplary cycloalkyl groups include cyclopropyl, cyclobutyl, cyclopentyl, cyclohexyl, cycloheptyl, cyclooctyl, norbornyl, decalin, adamantyl and the like. In one embodiment, the cycloalkyl group contains one double bond. Preferably, the cycloalkyl groups containing one double bond have from four to twelve carbon atoms (i.e., $C_4$-$C_{12}$ cycloalkenyl). Exemplary cycloalkyl groups containing one double bond include cyclobutenyl, cyclopentenyl, cyclohexenyl, cycloheptenyl, cyclooctenyl, cyclononenyl, cyclodecenyl, among others. In another embodiment, the cycloalkyl group contains two double bonds. Preferably, the cycloalkyl groups containing two double bonds have from five to twelve carbon atoms (i.e., $C_5$-$C_{12}$ cycloalkadienyl). Exemplary cycloalkyl groups having two double bonds include cyclopentadienyl, cyclohexadienyl, cycloheptadienyl, cyclooctadienyl, cyclononadienyl, cyclodecadienyl, among others.

Useful alkenyl groups are selected from straight-chain and branched-chain $C_{2-6}$ alkenyl groups, preferably $C_{2-4}$ alkenyl. Typical $C_{2-6}$ alkenyl groups include ethenyl, propenyl, isopropenyl, butenyl, sec-butenyl, pentenyl, and hexenyl. Typical $C_{2-4}$ alkenyl groups include ethenyl, propenyl, isopropenyl, butenyl, and sec-butenyl.

Useful alkynyl groups are selected from straight-chain and branched-chain $C_{2-6}$ alkynyl groups, preferably $C_{2-4}$ alkynyl. Typical $C_{2-6}$ alkynyl groups include ethynyl, propynyl, butynyl, 2-butynyl, pentynyl, and hexynyl groups. Typical $C_{2-4}$ alkynyl groups include ethynyl, propynyl, butynyl, and 2-butynyl groups.

Useful haloalkyl groups include any of the above-mentioned $C_{1-10}$ alkyl groups substituted by one or more fluorine, chlorine, bromine or iodine atoms (e.g., fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups).

Useful hydroxyalkyl groups include any of the above-mentioned $C_{1-10}$ alkyl groups substituted by one or more hydroxy groups, such as monohydroxyalkyl and dihydroxyalkyl groups (e.g., hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 2,3-dihydroxypropyl, 3-hydroxybutyl, 4-hydroxybutyl, 2-hydroxy-1-methylpropyl, and 1,3-dihydroxyprop-2-yl).

Useful alkoxy groups include oxygen substituted by one of the $C_{1-10}$ alkyl groups mentioned above (e.g., methoxy, ethoxy, propoxy, iso-propoxy, butoxy, tert-butoxy, iso-butoxy, sec-butoxy, pentyloxy, hexyloxy, heptyloxy, octyloxy, nonyloxy and decyloxy).

Useful alkoxyalkyl groups include any of the above-mentioned $C_{1-10}$ alkyl groups substituted with any of the above-mentioned alkoxy groups (e.g., methoxymethyl, methoxyethyl, methoxypropyl, methoxybutyl, ethoxymethyl, ethoxyethyl, ethoxypropyl, ethoxybutyl, propoxymethyl, isopropoxymethyl, propoxyethyl, propoxypropyl, butoxymethyl, tert-butoxymethyl, isobutoxymethyl, sec-butoxymethyl, and pentyloxymethyl).

Useful haloalkoxy groups include oxygen substituted by one of the $C_{1-10}$ haloalkyl groups mentioned above (e.g., fluoromethoxy, difluoromethoxy, trifluoromethoxy, and 2,2,2-trifluoroethoxy).

Useful (cycloalkyl)alkyl groups include any of the above-mentioned $C_{1-10}$ alkyl groups substituted with any of the above-mentioned cycloalkyl groups (e.g., cyclopropylmethyl, cyclopropylethyl, cyclopropylpropyl, cyclobutylmethyl, cyclopentylmethyl, cyclohexylmethyl, and the like).

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl, and fluorenyl groups, more preferably phenyl, naphthyl, and biphenyl groups.

Useful aryloxy groups include oxygen substituted by one of the aryl groups mentioned above (e.g., phenoxy).

Useful arylalkyl groups include any of the above-mentioned $C_{1-10}$ alkyl groups substituted by any of the above-mentioned aryl groups (e.g., benzyl, phenethyl, and the like).

Useful aralkyloxy groups include oxygen substituted by one of the above-mentioned arylalkyl groups (e.g., benzyloxy).

The term "heteroaryl" or "heteroaromatic" as employed herein refers to groups having 5 to 14 ring atoms, with 6, 10 or 14 π electrons shared in a cyclic array, and containing carbon atoms and 1, 2, or 3 oxygen, nitrogen or sulfur heteroatoms, or 4 nitrogen atoms. Examples of heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. Typical heteroaryl groups include thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl).

Useful heteroarylalkyl groups include any of the above-mentioned $C_{1-10}$ alkyl groups substituted by any of the above-mentioned heteroaryl groups (e.g., imidazol-1-ylmethyl, imidazol-1-ylethyl, imidazol-1-ylpropyl, pyridin-2-ylmethyl, pyridin-2-ylethyl, pyridin-3-ylmethyl, pyridin-3-ylethyl, pyridin-4-ylmethyl, pyridin-4-ylethyl, and the like).

The terms "heterocyclic" and "heterocyclo" are used herein to mean saturated or wholly or partially unsaturated 3-7 membered monocyclic, or 7-10 membered bicyclic ring system, which consist of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon atom or on a nitrogen atom if the resulting compound is stable. In one embodiment, the 3- to 7-membered monocyclic heterocyclic ring is either a saturated, or unsaturated non-aromatic ring. A 3-membered heterocyclo can contain up to 1 heteroatom, a 4-membered heterocyclo can contain up to 2 heteroatoms, a 5-membered heterocyclo can contain up to 4 heteroatoms, a 6-membered heterocyclo can contain up to 4 heteroatoms, and a 7-membered heterocyclo can contain up to 5 heteroatoms. Each heteroatom is independently selected from nitrogen, which can be quaternized; oxygen; and sulfur, including sulfoxide and sulfone. The 3- to 7-membered heterocyclo can be attached via a nitrogen or carbon atom. A 7- to 10-membered bicyclic heterocyclo contains from 1 to 4 heteroatoms independently selected from nitrogen, which can be quaternized; oxygen; and sulfur, including sulfoxide and sulfone. The 7- to 10-membered bicyclic heterocyclo can be attached via a nitrogen or carbon atom. Examples include, but are not limited to, pyrrolidinyl, piperidinyl, 2-oxo-piperidinyl, piperazinyl, morpholinyl, imidazolinyl, pyrazolidinyl, tetrahydrofuranyl, oxazolidinyl, 2-oxooxazolidinyl, isoxazolidinyl, 3-oxo-isoxazolidinyl, tetrahydrothienyl, imidazolidinyl, 2-oxoimidazolidinyl, hexahydropyrimidinyl, endo-9-methyl-9-azabicyclo[3.3.1]nonan-3-yl, 8-methyl-8-azabicyclo[3.2.1]octan-3-yl, endo-8-tert-butoxycarbonyl-8-azabicyclo[3.2.1]octan-3-yl, benzodiazepines, and the like.

Useful heterocycloalkyl groups include any of the above-mentioned $C_{1-10}$ alkyl groups substituted by any of the above-mentioned heterocyclic groups (e.g., (pyrrolidin-2-yl)methyl, (pyrrolidin-1-yl)methyl, (piperidin-1-yl)methyl, (morpholin-1-yl)methyl, (2-oxooxazolidin-4-yl)methyl, (2-oxooxazolidin-4-yl)ethyl, (2-oxo-imidazolidin-1-yl)methyl, (2-oxo-imidazolidin-1-yl)ethyl, (2-oxo-imidazolidin-1-yl)propyl, and the like).

As used herein, the term "amino" or "amino group" refers to —$NH_2$.

Useful aminoalkyl groups include any of the above-mentioned $C_{1-10}$ alkyl groups substituted with an amino group.

Useful diaminoalkyl groups include any of the above-mentioned $C_{1-10}$ alkyl groups substituted with two amino groups.

Useful alkylamino and dialkylamino groups are —$NHR^{18}$ and —$NR^{18}R^{19}$, respectively, wherein $R^{20}$ and $R^{21}$ are each independently selected from a $C_{1-10}$ alkyl group.

Useful hydroxyalkylamino groups are —$NHR^{19}$, wherein $R^{19}$ is any of the above-mentioned hydroxyalkyl groups.

Useful alkylaminoalkyl and dialkylaminoalkyl groups are any of the above-mentioned $C_{1-10}$ alkyl groups substituted by any of the above-mentioned alkylamino and dialkylamino groups, respectively.

The term "carbonyl" means —C(=O)—.

The term "oxo" means =O.

Useful alkoxycarbonyl groups include a carbonyl group substituted by any of the above-mentioned $C_{1-10}$ alkoxy groups (e.g., methoxycarbonyl, ethoxycarbonyl, and propoxycarbonyl).

As used herein, the term "aminocarbonyl" refers to —C(=O)$NH_2$.

As used herein, the term "aminosulfonyl" refers to —$SO_2NH_2$.

Useful alkylcarbonyl groups include a carbonyl group, i.e., —C(=O)—, substituted by any of the above-mentioned $C_{1-10}$ alkyl groups.

Useful alkylcarbonyloxy or acyloxy groups include oxygen substituted by one of the above-mentioned alkylcarbonyl groups.

Useful alkylcarbonylamino or acylamino groups include any of the above-mentioned alkylcarbonyl groups attached to an amino nitrogen, such as methylcarbonylamino.

As used herein, the term "carboxamido" refers to a radical of formula —C(=O)NR$^{20}$R$^{21}$, wherein R$^{20}$ and R$^{21}$ are each independently hydrogen, optionally substituted C$_{1-10}$ alkyl, or optionally substituted aryl. Exemplary carboxamido groups include —CONH$_2$, —CON(H)CH$_3$, —CON(CH$_3$)$_2$, and —CON(H)Ph and the like Useful (aminocarbonyl)alkyl groups are any of the above-mentioned C$_{1-10}$ alkyl groups substituted by one or more, typically 1 or 2, aminocarbonyl groups, such as aminocarbonylmethyl or 1,2-di(aminocarbonyl)ethyl.

Useful (aminocarbonyl)alkylamino groups are any of the above-mentioned (aminocarbonyl)alkyl groups attached to an amino nitrogen, such as (aminocarbonyl)methylamino.

Useful alkylaminocarbonyl and dialkylaminocarbonyl groups are any of the above-mentioned carboxamido groups, where R$^{20}$ is H and R$^{21}$ is C$_{1-10}$ alkyl or where R$^{20}$ and R$^{21}$ are each independently selected from a C$_{1-10}$ alkyl group, respectively.

As used herein, the term "sulfonamido" refers to a radical of formula —SO$_2$NR$^{22}$R$^{23}$, wherein R$^{22}$ and R$^{23}$ are each independently hydrogen, optionally substituted C$_{1-10}$ alkyl, or optionally substituted aryl. Exemplary sulfonamido groups include —SO$_2$NH$_2$, —SO$_2$N(H)CH$_3$, —SO$_2$N(H)Ph and the like.

As used herein, the term "alkylsulfonylamino" refers to —SO$_2$N(H)R$^{24}$, wherein R$^{24}$ is any of the above-mentioned C$_{1-10}$ alkyl groups.

As used herein, the term "(alkylsulfonylamino)alkyl" refers to any of the above-mentioned C$_{1-10}$ alkyl groups substituted with any of the above-mentioned alkylsulfonylamino groups.

Useful mercaptoalkyl groups include any of the above-mentioned C$_{1-10}$ alkyl groups substituted by a —SH group.

As used herein, the term "carboxy" refers to —COOH.

Useful carboxyalkyl groups include any of the above-mentioned C$_{1-10}$ alkyl groups substituted by —COOH.

Useful (carboxyalkyl)amino groups are —NHR$^{25}$, wherein R$^{25}$ is any of the above-mentioned carboxyalkyl groups.

As used herein, the term "ureido" refers to —NH—C(=O)—NH$_2$.

As used herein, the term "azido" refers to —N$_3$.

The term "about," as used herein in connection with a measured quantity, refers to the normal variations in that measured quantity, as expected by the skilled artisan making the measurement and exercising a level of care commensurate with the objective of measurement and the precision of the measuring equipment.

As used herein, the term "optionally substituted" refers to a group that may be unsubstituted or substituted.

Optional substituents on optionally substituted groups, when not otherwise indicated, include one or more groups, typically 1, 2, or 3 groups, independently selected from the group consisting of halo, halo(C$_{1-6}$)alkyl, aryl, heterocycle, cycloalkyl, C$_{1-6}$ alkyl, C$_{2-6}$ alkenyl, C$_{2-6}$ alkynyl, aryl(C$_{1-6}$)alkyl, aryl(C$_{2-6}$)alkenyl, aryl(C$_{2-6}$)alkynyl, cycloalkyl(C$_{1-6}$)alkyl, heterocyclo(C$_{1-6}$)alkyl, hydroxy(C$_{1-6}$)alkyl, amino(C$_{1-6}$)alkyl, carboxy(C$_{1-6}$)alkyl, alkoxy(C$_{1-6}$)alkyl, nitro, amino, ureido, cyano, alkylcarbonylamino, hydroxy, thiol, alkylcarbonyloxy, aryloxy, ar(C$_{1-6}$)alkyloxy, carboxamido, sulfonamido, azido, C$_{1-6}$ alkoxy, halo(C$_{1-6}$)alkoxy, carboxy, aminocarbonyl, and mercapto(C$_{1-6}$)alkyl groups mentioned above. Preferred optional substituents include halo, halo(C$_{1-6}$)alkyl, hydroxy(C$_{1-6}$)alkyl, amino(C$_{1-6}$)alkyl, hydroxy, nitro, C$_{1-6}$ alkyl, C$_{1-6}$ alkoxy, halo(C$_{1-6}$)alkoxy, and amino.

The present invention disclosed herein is also meant to encompass prodrugs of any of the disclosed compounds. As used herein, prodrugs are considered to be any covalently bonded carriers that release the active parent drug in vivo. In general, such prodrugs will be functional derivatives of compounds of Formulae I-V which will be readily convertible in vivo, e.g., by being metabolized, into the required compound of Formulae I-V. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984). Non-limiting examples of prodrugs include esters or amides of compounds of any of Formulae I-V having hydroxyalkyl or aminoalkyl as a substituent, and these may be prepared by reacting such parent compounds with anhydrides such as succinic anhydride.

The present invention disclosed herein is also intended to encompass any of the disclosed compounds being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, and preferably $^3$H, $^{11}$C, and $^{14}$C. Isotopically-labeled compounds of the present invention can be prepared by methods known in the art.

The present invention is also directed specifically to $^3$H, $^{11}$C, or $^{14}$C radiolabeled compounds of any of Formulae as well as their pharmaceutically acceptable salts, prodrugs and solvates, and the use of any such compounds as radioligands for their ability to bind to the sodium channel. For example, one use of the labeled compounds of the present invention is the characterization of specific receptor binding. Another use of a labeled compound of the present invention is an alternative to animal testing for the evaluation of structure-activity relationships. For example, the receptor assay may be performed at a fixed concentration of a labeled compound of the invention and at increasing concentrations of a test compound in a competition assay. For example, a tritiated compound of any of Formulae I-V can be prepared by introducing tritium into the particular compound, for example, by catalytic dehalogenation with tritium. This method may include reacting a suitably halogen-substituted precursor of the compound with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}$C-labeled compounds can be prepared by employing starting materials having a $^{14}$C carbon.

Some of the compounds disclosed herein may contain one or more asymmetric centers and may thus give rise to enantiomers, diastereomers, and other stereoisomeric forms. The present invention is meant to encompass the use of all such possible forms, as well as their racemic and resolved forms and mixtures thereof. The individual enantiomers may be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treating" or "treatment" is meant to encompass administering to a subject a compound of the present invention for the purposes of amelioration or cure, including preemptive and palliative treatment. The term "$R^8$ is a bond" for —$OR^8$ refers to the formation of an =O group with the carbon atom to which the —$OR^8$ group is attached.

When numeric ranges are provided for parameters, e.g. the parameter being 0-5, then it is meant that all of the numbers inbetween are also encompassed, such as q is 0-5 means that q is selected from 0, 1, 2, 3, 4, or 5.

The invention disclosed herein also encompasses the use of salts of the disclosed compounds, including all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

The invention disclosed herein is also meant to encompass solvates of any of the disclosed compounds. Solvates typically do not significantly alter the physiological activity or toxicity of the compounds, and as such may function as pharmacological equivalents. The term "solvate" as used herein is a combination, physical association and/or solvation of a compound of the present invention with a solvent molecule such as, e.g. a disolvate, monosolvate or hemisolvate, where the ratio of solvent molecule to compound of the present invention is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of any of Formulae I-V may be present as solvated forms with a pharmaceutically acceptable solvent, such as water, methanol, ethanol, and the like, and it is intended that the invention includes both solvated and unsolvated forms of compounds of any of Formulae I-V. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.*: 603-604 (2001). A typical, non-limiting, process of preparing a solvate would involve dissolving a compound of any of Formulae I-V in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Since compounds of Formulae I-V are modulators, in particular blockers of sodium ($Na^+$) channels, a number of diseases and conditions mediated by sodium ion influx can be treated by employing these compounds. The present invention is thus directed generally to a method for treating a disorder responsive to the blockade of sodium channels in an animal suffering from, or at risk of suffering from, said disorder, said method comprising administering to the animal an effective amount of a compound represented by any of defined Formulae I-V, or a pharmaceutically acceptable salt, prodrug or solvate thereof.

The present invention is further directed to a method of modulating, in particular blocking, sodium channels in an animal in need thereof, said method comprising administering to the animal a modulating-effective amount of at least one compound represented by any of defined Formulae I-V, or a pharmaceutically acceptable salt, prodrug or solvate thereof.

More specifically, the present invention provides a method of treating stroke, neuronal damage resulting from head trauma, epilepsy, seizures, general epilepsy with febrile seizures, severe myoclonic epilepsy in infancy, neuronal loss following global and focal ischemia, pain (e.g., acute pain, chronic pain, which includes but is not limited to neuropathic pain, postoperative pain and inflammatory pain, or surgical pain), migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia. In one embodiment, the invention provides a method of treating pain. In another embodiment, the type of pain is chronic pain. In another embodiment, the type of pain is neuropathic pain. In another embodiment, the type of pain is postoperative pain. In another embodiment, the type of pain is inflammatory pain. In another embodiment, the type of pain is surgical pain. In another embodiment, the type of pain is acute pain. In another embodiment, the treatment of pain (e.g., chronic pain, such as neuropathic pain or inflammatory pain, acute pain or surgical pain) is preemptive. In another embodiment, the treatment of pain is palliative. In each instance, such method of treatment requires administering to an animal in need of such treatment an amount of a compound of the present invention that is therapeutically effective in achieving said treatment. In one embodiment, the amount of such compound is the amount that is effective as to block sodium channels in vivo.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 2000; 18: 387-391).

The inflammatory process is a complex series of biochemical and cellular events activated in response to tissue injury or the presence of foreign substances (Levine, *Inflammatory Pain, In: Textbook of Pain*, Wall and Melzack eds., 3$^{rd}$ ed., 1994). Inflammation often occurs, at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, that associated with osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but not limited to pain caused by nerve injury such as, for example, the pain from which diabetics suffer.

The present invention is also directed to the use of a compound represented by any of defined Formulae I-V, or a pharmaceutically acceptable salt, prodrug or solvate thereof, in the manufacture of a medicament for treating a disorder responsive to the blockade of sodium channels (e.g., any of the disorders listed above) in an animal suffering from said disorder.

Furthermore, the present invention is directed to a compound represented by any of Formulae I-V, or a pharmaceutically acceptable salt, prodrug or solvate thereof, for use in modulating, in particular blocking, sodium channels in an animal in need thereof.

The present invention is also directed to the use of a compound represented by any of defined Formulae I-V, or a pharmaceutically acceptable salt, prodrug or solvate thereof, in the manufacture of a medicament, in particular a medicament for modulating, in particular blocking, sodium channels, in an animal in need thereof.

Synthesis of Compounds

The compounds of the present invention can be prepared using methods known to those skilled in the art in view of this disclosure. For example, compounds of Formula I can be prepared as shown in Schemes 1-6 below. Additional methods of synthesis are described and illustrated in the working examples set forth below.

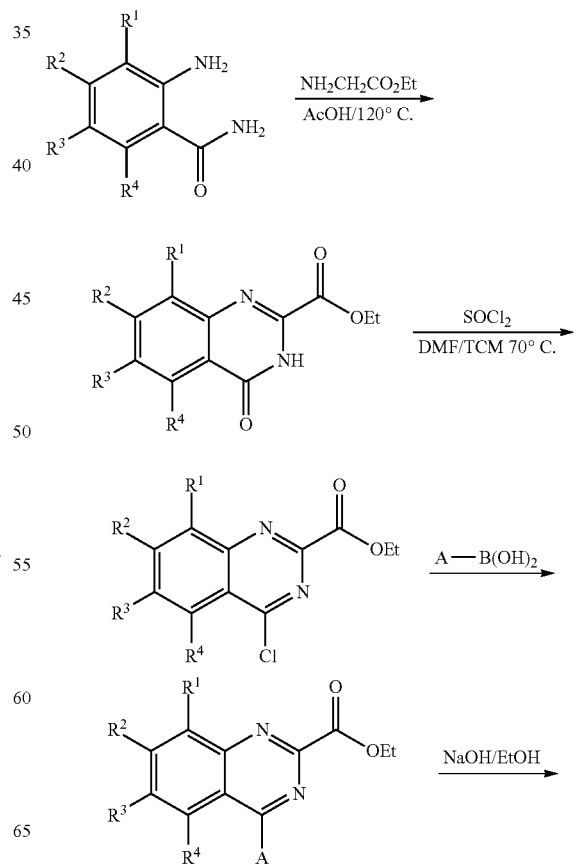

Scheme 1

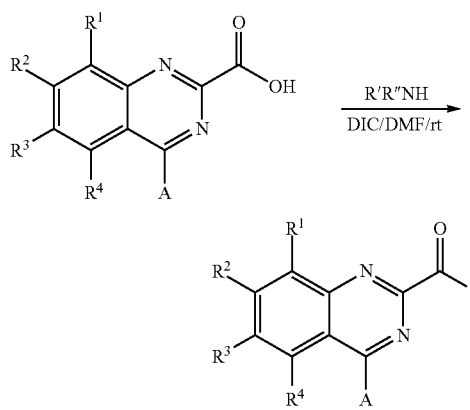

wherein $R^1$, $R^2$, $R^3$, $R^4$, and A are as defined above for Formula I, and R' and R" are each independently selected from the group consisting of hydrogen and $C_{1-6}$ alkyl.

Scheme 2

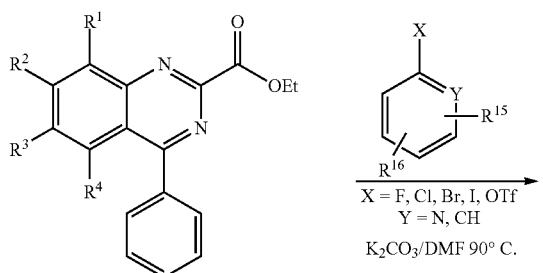

wherein $R^1$, $R^2$, $R^3$, $R^4$, $R^5$, $R^6$, and A are as defined above for Formula I. Ref. 1: (a) Eiichi YAMAMOTO et al., U.S. Pat. Appl. Publ. No. 2009/0062539; (b) Kazuhiro Yokoyama et al., *Bioorg. Med. Chem.* 17:64-73 (2009).

Scheme 3

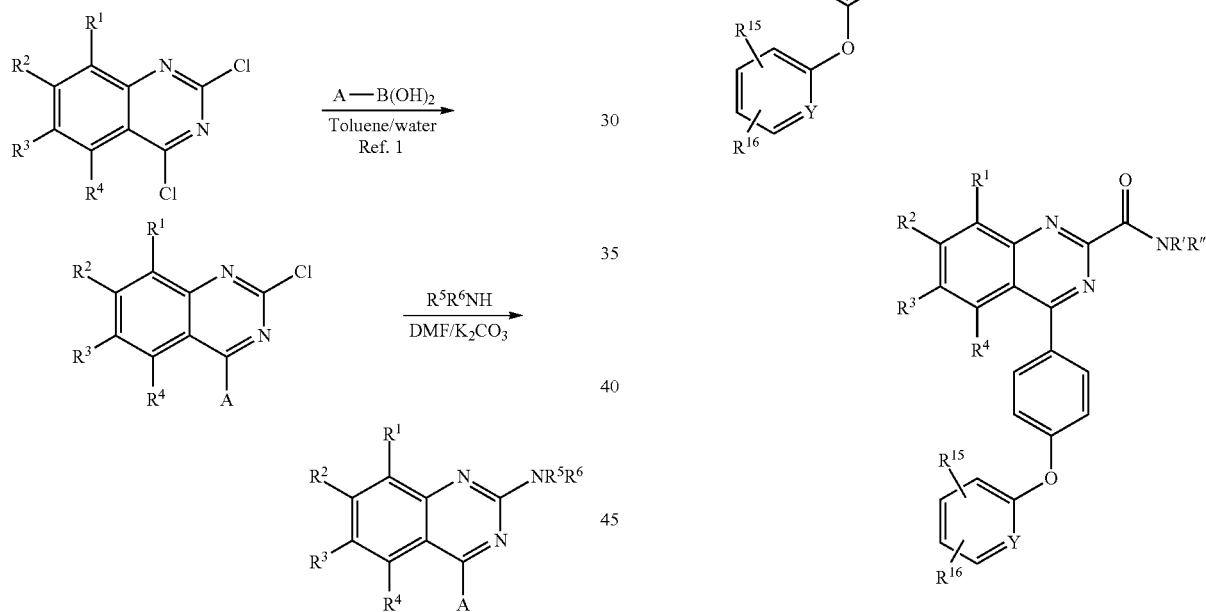

wherein $R^1$, $R^2$, $R^3$, $R^4$, $R^{15}$, and $R^{16}$ are as defined above for Formula I, and R' and R" are each independently selected from the group consisting of hydrogen and $C_{1-4}$ alkyl.

Scheme 4

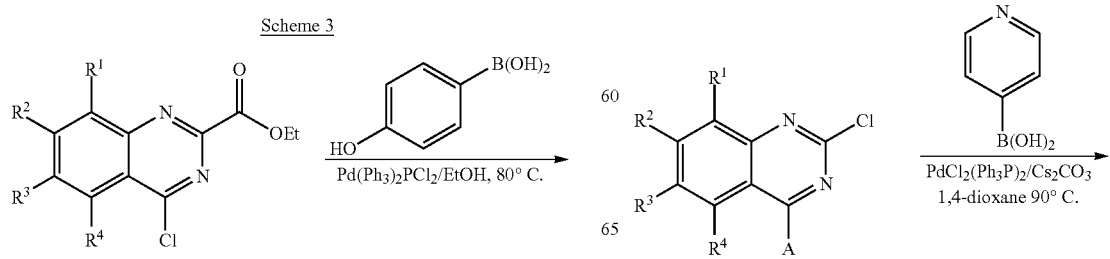

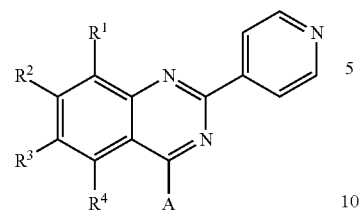

wherein R¹, R², R³, R⁴, and A are as defined above for Formula I.

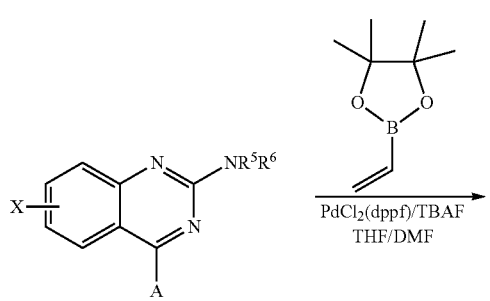

Scheme 5

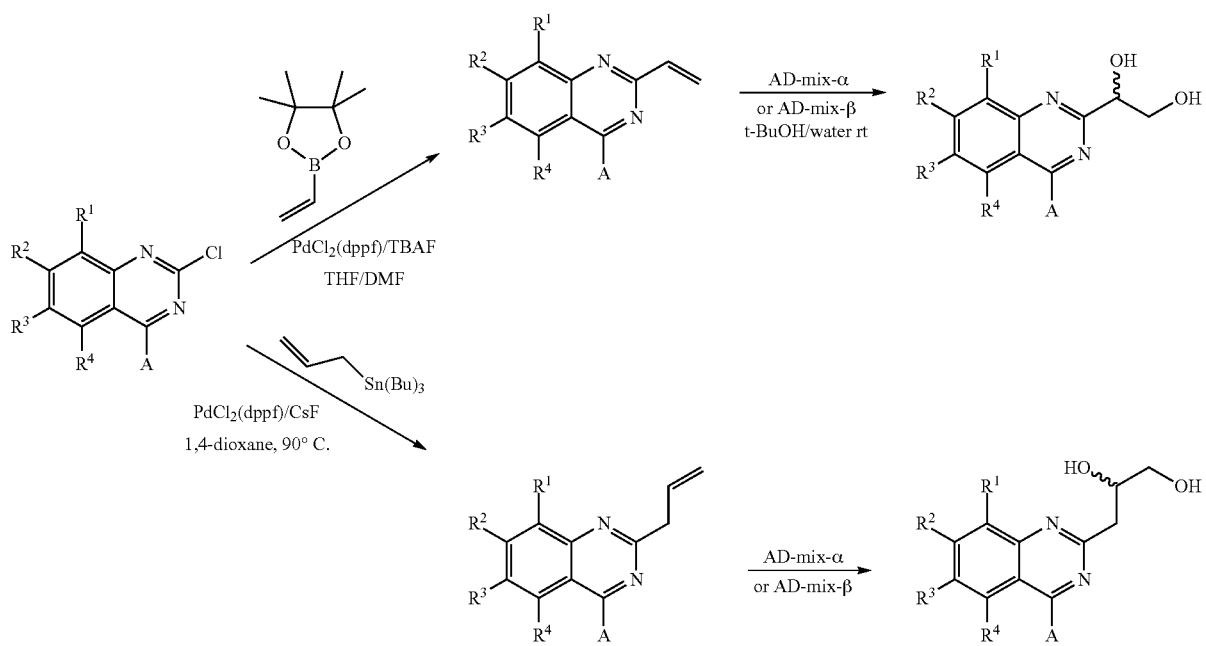

wherein R¹, R², R³, R⁴, and A are as defined above for Formula I.

Scheme 6

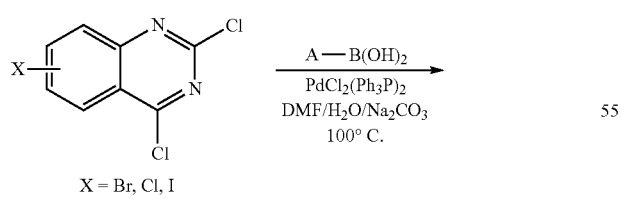

X = Br, Cl, I

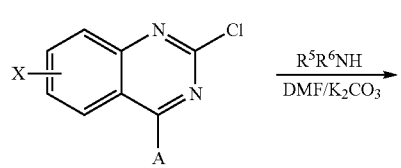

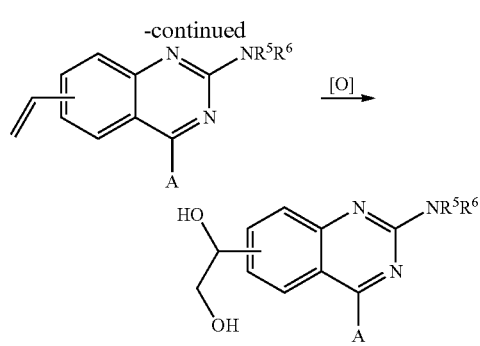

wherein $R^5$, $R^6$, and A are as defined above for Formula I.

Testing of Compounds

Compounds of the present invention were assessed by sodium mobilization and/or electrophysiological assays for sodium channel blocker activity. One aspect of the present invention is based on the use of the compounds herein described as sodium channel blockers. Based upon this property, compounds of the present invention are considered useful in treating a condition or disorder responsive to the blockade of sodium ion channels, e.g., stroke, neuronal damage resulting from head trauma, epilepsy, seizures, general epilepsy with febrile seizures, severe myoclonic epilepsy in infancy, neuronal loss following global and focal ischemia, a neurodegenerative disorder (e.g., Alzheimer's disease, amyotrophic lateral sclerosis (ALS), or Parkinson's disease), migraine, familial primary erythromelalgia, paroxysmal extreme pain disorder, cerebellar atrophy, ataxia, dystonia, tremor, mental retardation, autism, manic depression, tinnitus, myotonia, a movement disorder, or cardiac arrhythmia, or providing local anesthesia. Compounds of the Invention are also expected to be effective in treating pain, such as acute pain, chronic pain, which includes but is not limited to neuropathic pain, postoperative pain and inflammatory pain, or surgical pain.

More specifically, the present invention is directed to compounds of Formulae I-V that are blockers of sodium channels. According to the present invention, those compounds having useful sodium channel blocking properties exhibit an $IC_{50}$ for $Na_v1.1$, $Na_v1.2$, $Na_v1.3$, $Na_v1.4$, $Na_v1.5$, $Na_v1.6$, $Na_v1.7$, $Na_v1.8$ and/or $Na_v1.9$ of about 100 µM or less, e.g., about 50 µM or less, about 10 µM or less, about 5 µM or less, or about 1 µM or less, in the sodium mobilization and/or electrophysiological assays described herein. In certain embodiments, Compounds of the Invention exhibit an $IC_{50}$ for $Na_v1.7$ of 100 µM or less, e.g., about 50 µM or less, about 10 µM or less, about 5 µM or less, or about 1 µM or less, about 0.5 µM or less, or about 0.1 µM or less. Compounds of the Invention can be tested for their $Na^+$ channel blocking activity using methods known in the art and by the following fluorescence imaging and electrophysiological in vitro assays and/or in vivo assays.

In Vitro Assay Protocols

FLIPR® Assays:

Recombinant $Na_v1.7$ Cell Line:

In vitro assays were performed in a recombinant cell line expressing cDNA encoding the alpha subunit ($Na_v1.7$, SCN9a, PN1, NE) of human $Na_v1.7$ (Accession No. NM_002977). The cell line was provided by investigators at Yale University (Cummins et al, *J. Neurosci.* 18(23): 9607-9619 (1998)). For dominant selection of the $Na_v1.7$-expressing clones, the expression plasmid co-expressed the neomycin resistance gene. The cell line was, constructed in the human embryonic kidney cell line, HEK293, under the influence of the CMV major late promoter, and stable clones were selected using limiting dilution cloning and antibiotic selection using the neomycin analogue, G418. Recombinant beta and gamma subunits were not introduced into this cell line. Additional cell lines expressing recombinant $Na_v1.7$ cloned from other species can also be used, alone or in combination with various beta subunits, gamma subunits or chaperones.

Non-recombinant Cell Lines Expressing Native $Na_v1.7$:

Alternatively, in vitro assays can be performed in a cell line expressing native, non-recombinant $Na_v1.7$, such as the ND7 mouse neuroblastoma X rat dorsal root ganglion (DRG) hybrid cell line ND7/23, available from the European Cell Culture Collection (Cat. No. 92090903, Salisbury, Wiltshire, United Kingdom). The assays can also be performed in other cell lines expressing native, non-recombinant $Na_v1.7$, from various species, or in cultures of fresh or preserved sensory neurons, such as dorsal root ganglion (DRG) cells, isolated from various species. Primary screens or counter-screens of other voltage-gated sodium channels can also be performed, and the cell lines can be constructed using methods known in the art, purchased from collaborators or commercial establishments, and they can express either recombinant or native channels. The primary counter-screen is for one of the central neuronal sodium channels, $Na_v1.2$ (rBIIa), expressed in HEK293 host cells (Ilyin et al., *Br. J. Pharmacol.* 144:801-812 (2005)). Pharmacological profiling for these counter-screens is carried out under conditions similar to the primary or alternative $Na_v1.7$ assays described below.

Cell Maintenance:

Unless otherwise noted, cell culture reagents were purchased from Mediatech of Herndon, Va. The recombinant $Na_v1.7$/HEK293 cells were routinely cultured in growth medium consisting of Dulbecco's minimum essential medium containing 10% fetal bovine serum (FBS, Hyclone, Thermo Fisher Scientific, Logan, Utah), 100 U/mL penicillin, 100 µg/mL streptomycin, 2-4 mM L-glutamine, and 500 mg/mL G418. For natural, non-recombinant cell lines, the selective antibiotic was omitted, and additional media formulations can be applied as needed.

Assay Buffer:

The assay buffer was formulated by removing 120 mL from a 1 L bottle of fresh, sterile $dH_2O$ (Mediatech, Herndon, Va.) and adding 100 mL of 10×HBSS that does not contain $Ca^{++}$ or $Mg^{++}$ (Gibco, Invitrogen, Grand Island, N.Y.) followed by 20 mL of 1.0 M Hepes, pH 7.3 (Fisher Scientific, BP299-100). The final buffer consisted of 20 mM Hepes, pH 7.3, 1.261 mM $CaCl_2$, 0.493 mM $MgCl_2$, 0.407 mM $Mg(SO)_4$, 5.33 mM KCl, 0.441 mM $KH_2PO_4$, 137 mM NaCl, 0.336 mM $Na_2HPO4$ and 0.556 mM D-glucose (Hanks et al., *Proc. Soc. Exp. Biol. Med.* 71:196 (1949)), and the simple formulation was typically the basic buffer throughout the assay (i.e., all wash and addition steps).

CoroNa™ Green AM $Na^+$ Dye for Primary Fluorescence Assay:

The fluorescence indicator used in the primary fluorescence assay was the cell permeant version of CoroNa™ Green (Invitrogen, Molecular Probes, Eugene, Oreg.), a dye that emits light in the fluorescence range (Harootunian et al., *J. Biol. Chem.* 264(32):19458-19467 (1989)). The intensity of this emission, but not the wavelength range, is increased when the dye is exposed to $Na^+$ ions, which it can bind with partial selectivity. Cells expressing $Na_v1.7$ or other sodium channels were loaded with the CoroNa™ Green dye immediately in advance of the fluorescence assay, and then, after agonist stimulation, the mobilization of $Na^+$ ions was detected as the $Na^+$ ions flowed from the extracellular fluid into the cytoplasm through the activated sodium channel pores. The dye was stored in the dark as a lyophilized powder, and then an aliquot was dissolved immediately before the cell loading procedure, according to the instructions of the manufacturer to a stock concentration of 10 mM in DMSO. It was then diluted in the assay buffer to a 4× concentrated working solution, so that the final concentration of dye in the cell loading buffer was 5 µM.

Membrane Potential Dye for Alternative Fluorescence Assays:

A fluorescence indicator that can be used in alternative fluorescence assays is the blue version membrane potential dye (MDS, Molecular Devices, Sunnyvale, Calif.), a dye that detects changes in molecules following a change in membrane potential. An increase in fluorescence is expected if agonist stimulation provokes a change in membrane potential. Cells expressing $Na_v1.7$ or other sodium channels are incubated with the membrane potential dye 30-60 minutes before the fluorescence assay. In the case of the KCl pre-stimulation version of the assay, the dye and all other components are washed out immediately before the assay, and the dye is then replaced. In the version lacking KCl pre-stimulation, the dye remains on the cells and is not washed out or replaced. The dye is stored in the dark as a lyophilized powder, and then an aliquot dissolved in assay buffer to form a 20×-concentrated stock solution that can be used for several weeks.

Agonists:

In the fluorescence assays, two agonists were used in combination, namely 1) veratridine; and 2) the venom from the yellow scorpion, *Leiurus quinquestriatus hebraeus*. Veratridine is an alkaloid small molecule that facilitates the capture of channel openings by inhibiting inactivation, and the scorpion venom is a natural preparation that includes peptide toxins selective for different subsets of voltage-gated sodium channels. These scorpion toxins inhibit the fast inactivation of their cognate target channels. Stock solutions of the agonists were prepared to 40 mM in DMSO (veratridine) and 1 mg/mL in $dH_2O$ (scorpion venom), and then diluted to make a 4× or 2× stock (depending on the particular assay) in assay buffer, the final concentration being 100 μM (veratridine) and 10 μg/mL (scorpion venom). Both of the agonists were purchased from Sigma Aldrich, St. Louis, Mo.

Test Compounds:

Test compounds were dissolved in DMSO to yield 10 mM stock solutions. The stock solutions were further diluted using DMSO in 1:3 serial dilution steps with 10 points (10,000 μM, 3,333 μM, 1,111 μM, 370 μM, 123 μM, 41 μM, 14 μM, 4.6 μM, 1.5 μM and 0.5 μM). The stock solutions were further diluted in assay buffer (1:125) as 4× stock serial dilutions with a DMSO concentration of 0.8% (final [DMSO], in the assay, from the compounds component=0.2%), so that the compounds' final concentrations in the assay were 20 μM, 6.7 μM, 2.2 μM, 0.74 μM, 0.25 μM and 0.08 μM, 0.03 μM, 0.01 μM, 0.003 μM and 0.001 μM. If a particular test article appeared to be especially potent, then the concentration curve was adjusted, e.g., to 10-fold lower concentrations, in order to perform the dose-response in a more relevant concentration range. Compound dilutions were added during the dye-loading and pre-stimulation step, and then again during the fluorescence assay, early in the kinetic read. Compound dilutions were added in duplicate rows across the middle 80 wells of the 96-well plate, whereas the fully stimulated and the fully inhibited controls (positive and negative) were located in the top 4 side wells and the bottom 4 side wells, respectively, on the left and right sides of the assay plate.

Data Analysis:

The data were analyzed according to methods known to those skilled in the art or using the GraphPad® Prism 4.0 Program (available from GraphPad Software, San Diego, Calif.) to determine the $IC_{50}$ value for the test article. At least one standard reference compound was evaluated during each experiment.

FLIPR® or FLIPR$^{TETRA}$® Sodium Dye Assay with KCl and Test Article Pre-Incubation:

Cells were prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate was then incubated in growth media, with or without selective antibiotic, overnight at 37° C. at 5% $CO_2$, 95% humidity, in preparation for the assay. For counter-screens of other voltage-gated sodium channels, the procedure was very similar, though optimal densities of cells, media and subsequent assay components can be fine-tuned for the particular cell line or isoform.

The next day, at the start of the assay, the media was flicked from the cells and the wells were washed once with 50 μL/well assay buffer (1× Hank's balanced salt solution without sodium bicarbonate or phenol red, 20 mM Hepes, pH 7.3) and then pre-incubated with the test articles, CoroNa™ Green AM sodium dye (for cell loading) and KCl for re-polarization and synchronization of the channels in the entire population of cells. For this dye-loading and pre-stimulation step, the components were added as follows, immediately after the wash step: 1) first, the compound dilutions and controls were added as 4× concentrates in assay buffer at 50 μL/well; 2) CoroNa™ Green AM dye was diluted from the stock solution to 20 μM in assay buffer (4× concentrate) and added to the plate at 50 μL/well; and 3) finally, a solution of 180 mM KCl (2×) was prepared by diluting a 2M stock solution into assay buffer and the solution was added to the cells at 100 μL/well. The cells were incubated at 25° C. in the dark for 30 mM. before their fluorescence was measured.

The plates containing dye-loaded cells were then flicked to remove the pre-incubation components and washed once with 100 μL/well assay buffer. A 100 μL/well aliquot of assay buffer was added back to the plate, and the real-time assay was commenced. The fluorescence of cells was measured using a fluorescence plate reader (FLIPR$^{TETRA}$® or FLIPR384®, MDS, Molecular Devices, Sunnyvale, Calif.) Samples were excited by either a laser or a PMT light source (Excitation wavelength=470-495 nM) and the emissions are filtered (Emission wavelength=515-575 nM). The additions of compound and the channel activators in this cell-based, medium-to-high throughput assay were performed on the fluorescence plate reader and the results (expressed as relative fluorescence units) were captured by means of camera shots every 1-3 sec., then displayed in real-time and stored. Generally, there was a 15 sec. base line, with camera shots taken every 1.5 sec., then the test compounds were added, then another 120 sec. baseline was conducted, with camera shots taken every 3 sec.; and finally, the agonist solution (containing veratridine and scorpion venom) was added. The amplitude of fluorescence increase, resulting from the binding of $Na^+$ ions to the CoroNa™ Green dye, was captured for ~180 sec. thereafter. Results were expressed in relative fluorescence units (RFU) and can be determined by using the maximum signal during the latter part of the stimulation; or the maximum minus the minimum during the whole agonist stimulation period; or by taking the area under the curve for the whole stimulation period.

The assay can be performed as a screening assay as well with the test articles present in standard amounts (e.g., 10 μM) in only one or two wells of a multi-well plate during the primary screen. Hits in this screen were typically profiled more exhaustively (multiple times), subjected to dose-response or competition assays and tested in counter screens against other voltage-gate sodium channels or other biologically relevant target molecules.

FLIPR® or FLIPR$^{TETRA}$® Membrane Potential Assay with KCl and Test Article Pre-Incubation:

Cells are prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% $CO_2$, 95% humidity, in preparation for the assay (see, e.g., Benjamin et. al., *J. Biomol. Screen* 10(4):365-373 (2005)). For screens and counter-screens of other voltage-gated sodium channels, the assay protocol is similar, though optimal densities of cells, media and subsequent assay components can be fine-tuned for the particular cell line or sodium channel isoform being tested.

The next day, at the start of the assay, the media is flicked from the cells and the wells are washed once with 50 μL/well assay buffer (1× Hank's balanced salt solution without sodium bicarbonate or phenol red, 20 mM Hepes, pH 7.3) and then pre-incubated with the test articles, the membrane potential dye (for cell loading), and the KCl for re-polarization and synchronization of the channels in the entire population of cells. For this dye-loading and pre-stimulation step, the components are added as follows, immediately after the wash step: 1) first, the compound dilutions and controls are added as 4× concentrates in assay buffer at 50 μL/well; 2) membrane potential dye is diluted from the stock solution in assay buffer (4× concentrate) and added to the plate at 50 μL/well; and 3) finally, a solution of 180 mM KCl (2×) is prepared by diluting a 2M stock solution into assay buffer and the solution added to the cells at 100 μL/well. The cells are incubated at 37° C. in the dark for 30-60 min. before their fluorescence is measured.

The plates containing dye-loaded cells are then flicked to remove the pre-incubation components and washed once with 50 μL/well assay buffer. A 50 μL/well aliquot of membrane potential dye is added back to the plate, and the real-time assay is commenced. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first) and then the channel activators (later) in this are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well with the test articles present in standard amounts (e.g., 10 μM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

FLIPR® or FLIPR$^{TETRA}$® Sodium Dye Assay without KCl and Test Article Pre-Incubation:

Cells are prepared by plating the recombinant HEK293 cells or other host cells expressing either recombinant or non-recombinant, native, Na$_v$1.7 alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% CO$_2$, 95% humidity, in preparation for the assay. For counter-screens of other voltage-gated sodium channels, the procedure is very similar, though optimal densities of cells, media and subsequent assay components can be fine-tuned for the particular cell line or isoform.

The next day, at the start of the assay, the media is flicked from the cells and the wells washed once with 50 μL/well assay buffer (1× Hank's balanced salt solution without sodium bicarbonate or phenol red, 20 mM Hepes, pH 7.3). Membrane potential dye is then added to each well of the 96-well plate (50 from a freshly diluted sample of the stock (now at 4× concentration) in the assay buffer. The cells are incubated at 37° C. in the dark for 30-60 mM. before their fluorescence is measured.

In this standard membrane potential assay, the 96-well plate containing dye-loaded cells is then loaded directly onto the plate reader without aspirating the dye solution and without any further washing of the cells. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first, 50 μL/well from a 4× stock plate) and then the channel activators (later, 100 μL/well from a 2× stock solution) in this kinetic assay are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well, with the test articles present in standard amounts (e.g. 10 μM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

Electrophysiology Assay

Cells:

The hNa$_v$1.7 expressing HEK-293 cells were plated on 35 mm culture dishes pre-coated with poly-D-lysine in standard DMEM culture media (Mediatech, Inc., Herndon, Va.) and incubated in a 5% CO$_2$ incubator at 37° C. Cultured cells were used approximately 12-48 hours after plating.

Electrophysiology:

On the day of experimentation, the 35 mm dish was placed on the stage of an inverted microscope equipped with a perfusion system that continuously perfuses the culture dish with fresh recording media. A gravity driven superfusion system was used to apply test solutions directly to the cell under evaluation. This system consists of an array of glass pipette glass connected to a motorized horizontal translator. The outlet of the shooter was positioned approximately 100 μm from the cell of interest.

Whole cell currents were recorded using the whole-cell patch clamp configuration using an Axopatch 200B amplifier (Axon Instruments, Foster City Calif.), 1322A A/D converter (Axon Instruments) and pClamp software (v. 8; Axon Instruments) and stored on a personal computer. Gigaseals were formed and the whole-cell configuration was established in voltage clamp mode, and membrane currents generated by hNa$_v$1.7 were recorded in gap-free mode. Borosilicate glass pipettes have resistance values between 1.5 and 2.0 MΩ when filled with pipette solution and series resistance (<5 MΩ) was compensated 75-80%. Signals were sampled at 50 kHz and low pass filtered at 3 kHz.

Voltage Protocols:

After establishing the whole-cell configuration in voltage clamp mode, voltage protocols were run to establish the 1) test potential, 2) holding potential, and 3) the conditioning potential for each cell.

After establishing the whole-cell configuration in voltage clamp mode, a standard I-V protocol was run to determine the potential at which the maximal current ($I_{max}$) is elicited. This potential was the test potential ($V_t$). To determine a conditioning potential at which 100% of channels were in the inactivated state, a standard steady-state inactivation (SSIN) protocol was run using a series of fifteen 100 ms-long depolarizing prepulses, incrementing in 10 mV steps, immediately followed by a 5 ms testing pulse, $V_t$, to $V_{max}$. This protocol also permitted determination of the holding potential at which all channels are in the resting state.

For compounds causing significant retardation of recovery from inactivation, an estimate of the affinity for the inactivated state of the channel ($K_i$) was generated using the following protocol. From the negative, no residual inactivation, holding potential, the cell was depolarized to the conditioning voltage for 2-5 seconds, returned to the negative holding potential for 10-20 ms to relieve fast inactivation and then depolarized to the test potential for ~15 ms. This voltage protocol was repeated every 10-15 seconds, first to establish a baseline in the absence of the test compound, then in the presence of the test compound.

After a stable baseline was established, the test compound was applied and block of the current elicited by the test pulse assessed. In some cases, multiple cumulative concentrations were applied to identify a concentration that blocked between 40-60% of this current. Washout of the compound was attempted by superfusing with control solution once steady-state block was observed. An estimate of the $K_i$ was calculated as follows:

$$K_i=[\text{drug}]*\{FR/(1-FR)\}, \qquad \text{Eq. 1}$$

where [drug] is the concentration of a drug, and $$FR=I(\text{after drug})/I(\text{control}), \qquad \text{Eq. 2}$$

where I is the peak current amplitude. If multiple concentrations were used, $K_i$ was determined from the fit of a logistic equation to FRs plotted against corresponding drug concentrations.

In the alternative, the voltage clamp protocol to examine hNa$_v$1.7 currents was as follows. First, the standard current-voltage relationship was tested by pulsing the cell from the holding voltage ($V_h$) of −120 mV by a series of 5 msec long square-shaped test pulses incrementing in +10 mV steps over the membrane voltage range of −90 mV to +60 mV at the pace of stimulation of 0.5 Hz. This procedure determines the voltage that elicits the maximal current ($V_{max}$). Second, $V_h$ was re-set to −120 mV and a steady-state inactivation (SSIN) curve was taken by the standard double-pulse protocol: 100 ms depolarizing pre-pulse was incremented in steps of +10 mV (voltage range from −90 mV to 0 mV) immediately followed by the 5 ms long test pulse to −10 mV at the pace of stimulation of 0.2 Hz. This procedure determines the voltage of full inactivation ($V_{full}$). Third, the cell was repeatedly stimulated with the following protocol, first in the absence of the test compound then in its presence. The protocol consisted of depolarizing the cell from the holding potential of −120 mV to the $V_{full}$ value for 4.5 seconds then repolarizing the cell to the holding potential for 10 ms before applying the test pulse to the $V_{max}$ for 5 ms. The amount of inhibition produced by the test compound was determined by comparing the current amplitude elicited by the test pulse in the absence and presence of the compound.

In a further alternative, the voltage clamp protocol to examine hNa$_v$1.7 currents was as follows. After establishing the whole-cell configuration in voltage clamp mode, two voltage protocols were run to establish: 1) the holding potential; and 2) the test potential for each cell.

Resting Block:

To determine a membrane potential at which the majority of channels are in the resting state, a standard steady-state inactivation (SSIN) protocol was run using 100 ms prepulses×10 mV depolarizing steps. The holding potential for testing resting block (Vh1) was 20 mV more hyperpolarized than the first potential where inactivation was observed with the inactivation protocol.

From this holding potential a standard I-V protocol was run to determine the potential at which the maximal current (Imax) is elicited. This potential was the test potential (Vt).

The compound testing protocol was a series of 10 ms depolarizations from the Vh1 (determined from the SSIN) to the Vt (determined from the I-V protocol) repeated every 10-15 seconds. After a stable baseline was established, a high concentration of a test compound (highest concentration solubility permits or that which provides ~50% block) was applied and block of the current assessed. Washout of the compound was attempted by superfusing with control solution once steady-state block was observed. The fractional response was calculated as follows:

$$K_r=[\text{drug}]*\{FR/(1-FR)\}, \qquad \text{Eq. 3}$$

where [drug] is the concentration of a drug, and $$FR=I(\text{after drug})/I(\text{control}), \qquad \text{Eq. 2}$$

where I is the peak current amplitude and was used for estimating resting block dissociation constant, $K_r$.

Block of Inactivated Channels:

To assess the block of inactivated channels the holding potential was depolarized such that 20-50% of the current amplitude was reduced when pulsed to the same Vt as above. The magnitude of this depolarization depends upon the initial current amplitude and the rate of current loss due to slow inactivation. This was the second holding potential (Vh2). The current reduction was recorded to determine the fraction of available channels at this potential (h).

$$h=I@Vh2/I\text{max}. \qquad \text{Eq. 4}$$

At this membrane voltage a proportion of channels was in the inactivated state, and thus inhibition by a blocker includes interaction with both resting and inactivated channels.

To determine the potency of the test compound on inactivated channels, a series of currents were elicited by 10 ms voltage steps from Vh2 to Vt every 10-15 seconds. After establishing a stable baseline, the low concentration of the compound was applied. In some cases, multiple cumulative concentrations will have to be applied to identify a concentration that blocks between 40-60% of the current. Washout is attempted to re-establish baseline. Fractional responses were measured with respect to a projected baseline to determine $K_{app}$.

$$K_{app}=[\text{drug}]*\{FR/(1-FR)\}, \quad \text{Eq. 5}$$

where [drug] is the concentration of a drug.

This $K_{app}$ value, along with the calculated $K_r$ and h values, were used to calculate the affinity of the compound for the inactivated channels ($K_i$) using the following equation:

$$K_i=(1-h)/((1/K_{app})-(h/K_r)). \quad \text{Eq. 6}$$

Solutions and Chemicals:

For electrophysiological recordings the external solution was either standard, DMEM supplemented with 10 mM HEPES (pH adjusted to 7.34 with NaOH and the osmolarity adjusted to 320) or Tyrodes salt solution (Sigma, USA) supplemented with 10 mM HEPES (pH adjusted to 7.4 with NaOH; osmolarity=320). The internal pipette solution contained (in mM): NaCl (10), CsF (140), CaCl$_2$ (1), MgCl$_2$ (5), EGTA (11), HEPES (10: pH 7.4, 305 mOsm). Compounds were prepared first as series of stock solutions in DMSO and then dissolved in external solution; DMSO content in final dilutions did not exceed 0.3%. At this concentration, DMSO did not affect sodium currents. Vehicle solution used to establish base line was also contacting 0.3% DMSO.

Data Analysis:

Data was analyzed off-line using Clampfit software (pClamp, v. 8; Axon Instruments) and graphed using Graph-Pad Prizm (v. 4.0) software.

In Vivo Assay for Pain

The compounds of the present invention can be tested for their antinociceptive activity in the formalin model as described in Hunskaar et al., *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period, mice are weighed and given either the compound of interest administered i.p. or p.o., or the appropriate volume of vehicle (for example, 10% Tween-80 or 0.9% saline, and other pharmaceutically acceptable vehicles) as control. Fifteen minutes after the i.p. dosing, and 30 minutes after the p.o. dosing mice are injected with formalin (20 pt of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

In Vivo Assays for Inflammatory or Neuropathic Pain

Test Animals:

Each experiment uses rats weighing between 200-260 g at the start of the experiment. The rats are group-housed and have free access to food and water at all times, except prior to oral administration of a test compound when food is removed for 16 hours before dosing. A control group acts as a comparison to rats treated with a compound of Formulae I-V. The control group is administered the carrier as used for the test compound. The volume of carrier administered to the control group is the same as the volume of carrier and test compound administered to the test group.

Inflammatory Pain:

To assess the actions of the compounds of Formulae I-V on the treatment of inflammatory pain the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (Bartho et al., *Naunyn-Schmiedeberg's Archives of Pharmacol.* 342:666-670 (1990)). The left hind paw of each animal is administered a 50 µL intraplantar injection of 50% FCA. 24 hour post injection, the animal is assessed for response to noxious mechanical stimuli by determining the paw withdrawal threshold (PWT), or to noxious thermal stimuli by determining the paw withdrawal latency (PWL), as described below. Rats are then administered a single injection of either a test compound or 30 mg/Kg of a positive control compound (indomethacin). Responses to noxious mechanical or thermal stimuli are then determined 1, 3, 5 and 24 hours post administration (admin). Percentage reversal of hyperalgesia for each animal is defined as:

$$\text{reversal} = \frac{[(\text{post administration } PWT \text{ or } PWL) - (\text{pre-administration } PWT \text{ or } PWL)]}{[(\text{baseline } PWT \text{ or } PWL) - (\text{pre-administration } PWT \text{ or } PWL)]} \times 100 \%$$

Neuropathic Pain:

To assess the actions of the test compounds for the treatment of neuropathic pain the Seltzer model or the Chung model can be used.

In the Seltzer model, the partial sciatic nerve ligation model of neuropathic pain is used to produce neuropathic hyperalgesia in rats (Seltzer et al., *Pain* 43:205-218 (1990)). Partial ligation of the left sciatic nerve is performed under isoflurane/O$_2$ inhalation anaesthesia. Following induction of anaesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anaesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

reversal =

$$\frac{[(\text{post administration } PWT) - (\text{pre-administration } PWT)] \%}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is (are) isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is (are) not manipulated. Following surgery animals are weighed, administered a subcutaneous (s.c.) injection of saline or ringers lactate, the wound area is dusted with antibiotic powder and they are kept on a warm pad until they recover from the anaesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a compound of Formulae I-V for the left rear paw of the animal. The animals can also be assessed for response to noxious thermal stimuli or for tactile allodynia, as described below. The Chung model for neuropathic pain is described in Kim et al., *Pain* 50(3):355-363 (1992).

Tactile Allodynia:

Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia:

Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

In Vivo Assay for Anticonvulsant Activity

The compounds of the present invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

Pharmaceutical Compositions

Although a Compound of the Invention can be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present invention include all compositions where a Compound of the Invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, a compound can be administered to a mammal, e.g., a human, orally at a dose of from about 0.0025 to about 1500 mg per kg body weight of the mammal, or an equivalent amount of a pharmaceutically acceptable salt, prodrug, or solvate thereof, per day to treat, prevent or ameliorate the particular disorder. A useful oral dose of a Compound of the Invention administered to a mammal is from about 0.0025 to about 50 mg per kg body weight of the mammal, or an equivalent amount of the pharmaceutically acceptable salt, prodrug, or solvate thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily, e.g., as one or more tablets or capsules, each containing from about 0.01 to about 50 mg of the compound, or an equivalent amount of a pharmaceutically acceptable salt, prodrug or solvate thereof.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a pharmaceutical composition of the present invention can be administered orally and is formulated into tablets, dragees, capsules or an oral liquid preparation. In one embodiment, the oral formulation comprises extruded multiparticulates comprising the compound of the invention.

Alternatively, a pharmaceutical composition of the present invention can be administered rectally, and is formulated in suppositories.

Alternatively, a pharmaceutical composition of the present invention can be administered by injection.

Alternatively, a pharmaceutical composition of the present invention can be administered transdermally.

Alternatively, a pharmaceutical composition of the present invention can be administered by inhalation or by intranasal or transmucosal administration.

Alternatively, a pharmaceutical composition of the present invention can be administered by the intravaginal route.

A pharmaceutical composition of the present invention can contain from about 0.01 to 99 percent by weight, and preferably from about 0.25 to 75 percent by weight, of active compound(s).

A method of the present invention, such as a method for treating a disorder responsive to the blockade of sodium channels in an animal in need thereof, can further comprise administering a second therapeutic agent to the animal in combination with a compound of the present invention. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

A Compound of the Invention (i.e., the first therapeutic agent) and the second therapeutic agent can act additively or, in one embodiment, synergistically. Alternatively, the second therapeutic agent can be used to treat a disorder or condition that is different from the disorder or condition for which the first therapeutic agent is being administered, and which disorder or condition may or may not be a condition or disorder as defined herein. In one embodiment, a Compound of the Invention is administered concurrently with a second therapeutic agent; for example, a single composition comprising both an effective amount of a compound of any of Formulae I-V, and an effective amount of the second therapeutic agent can be administered. Accordingly, the present invention further provides a pharmaceutical composition comprising a combination of a compound of the present invention, the second therapeutic agent, and a pharmaceutically acceptable carrier. Alternatively, a first pharmaceutical composition comprising an effective amount of a compound of any of Formulae I-V and a second pharmaceutical composition comprising an effective amount of the second therapeutic agent can be concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the compound of the present invention exerts its therapeutic effect for treating a disorder or condition.

The second therapeutic agent can be an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include nonsteroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxipinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating ALS include, but are not limited to, baclofen, neurotrophic factors, riluzole, tizanidine, benzodiazepines such as clonazepan and dantrolene.

Examples of useful therapeutic agents for treating cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating a migraine include, but are not limited to, sumatriptan; methysergide; ergotamine; caffeine; and beta-blockers such as propranolol, verapamil, and divalproex.

Examples of useful therapeutic agents for treating vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating dyskinesia include, but are not limited to, reserpine and tetrabenazine.

Examples of useful therapeutic agents for treating depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A pharmaceutical composition of the present invention is preferably manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethylstarch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound may be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

Ethyl 4-(4-phenoxyphenyl)quinazoline-2-carboxylate (3)

4-(4-phenoxyphenyl)quinazoline-2-carboxylic acid (4)

4-(4-phenoxyphenyl)quinazoline-2-carboxamide (5)

(a) A mixture of compound 1 (1 g, 1.0 eq., Syntech Dev.), compound 2 (1 g), $K_2CO_3$ (2 g) and bis(triphenylphosphine) palladium(II) chloride (Aldrich, 0.1 eq.), in 100 mL of EtOH/water (99/1) was heated at 50° C. for 24 hours. After cooling to room temperature, the reaction was quenched with water (100 mL), and extracted with $CHCl_3$ (2×400 mL). The organic layers were combined and concentrated, and the residue was dissolved in EtOH (100 mL) at room temperature, and then $H_2SO_4$ (2 mL) was added. The resulting mixture was heated at 60° C. for 14 hours. The solvent was removed and the residue was purified by column (Silica gel, $CHCl_3$) to obtain compound 3 as a white solid (1.2 g, yield 80%):

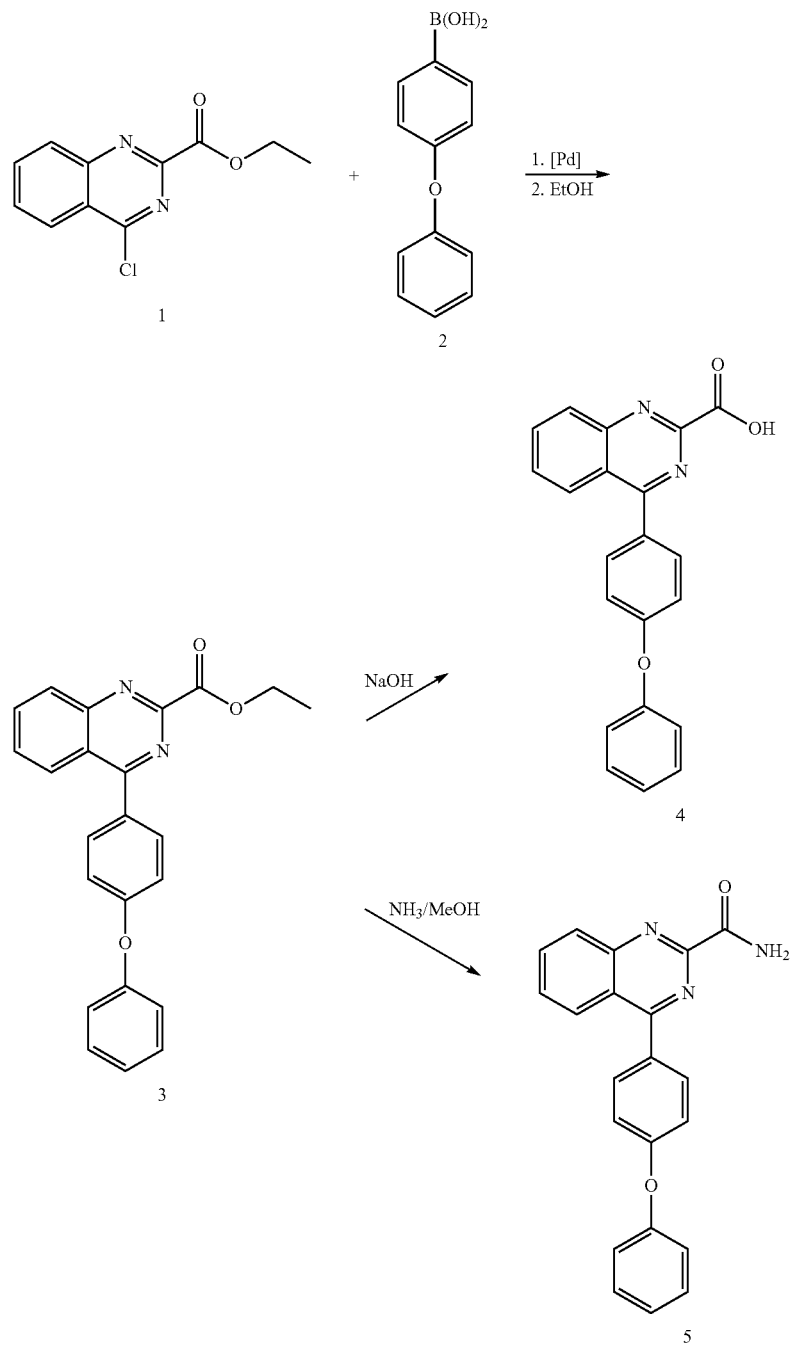

¹H-NMR (400 MHz, CDCl₃): δ 8.33 (d, 1H, 8.3 Hz), 8.25 (d, 1H, 8.3 Hz), 8.01 (dt, 1H, 1.3 & 8.1 Hz), 7.86 (d, 2H, 8.7 Hz), 7.74 (dt, 1H, 1.3 & 8.1 Hz), 7.39-7.44 (m, 2H), 7.17-7.21 (m, 3H), 7.11-7.14 (m, 2H), 4.61 (q, 2H, 7.0 Hz), 1.51 (t, 3H, 7.0 Hz); LC/MS: ink=371.4 [M+H]+ (Calc: 370.4).

(b) A mixture compound 3 (0.2 g) and NH₃ (7N in MeOH, 10 mL) was heated to 50° C. for 14 hours. After cooling to room temperature, the reaction was titrated with water, and the solid was collected, washed with water and dried to obtain compound 5 as a white solid (0.11 g, yield 60%): ¹H-NMR (400 MHz, CDCl₃): δ 8.34 (d, 1H, 8.3 Hz), 8.25 (d, 114, 8.3 Hz), 8.15 (br, 1H, NH), 8.01 (dt, 1H, 1.3 & 8.1 Hz), 7.86 (d, 211, 8.9 Hz), 7.73 (dt, 1H, 1.3 & 8.1 Hz), 7.39-7.44 (m, 2H), 7.13-7.23 (m, 5H), 5.99 (br, 1H, NH); LC/MS: m/z=342.5 [M+H]+ (Calc: 341.4).

(c) A mixture of compound 3 (0.2 g) in EtOH (5 mL) was treated with NaOH (1.5 mL, 2N aqueous) at 40° C. for 10 hours. The solvent was removed, and the residue was dissolved in TCM (20 mL) and neutralized with HCl (0.2N 10 mL) at 0° C. The organic layer was washed with brine, and concentrated to afford compound 4 as a white solid (80 mg, yield 44%): ¹H-NMR (400 MHz, CD₃OD): δ 8.25-8.31 (m, 2H), 8.06 0-8.11 (m, 1H), 7.98-8.02 (m, 2H), 7.79-7.83 (m, 1H), 7.5-7.55 (m, 2H), 7.21-7.31 (m, 5H); LC/MS: m/z=343.5 [M+H]+ (Calc: 342.4).

Example 2

(S)-1-(4-(4-(4-fluorophenoxy)phenyl)quinazolin-2-yl)ethane-1,2-diol (10)

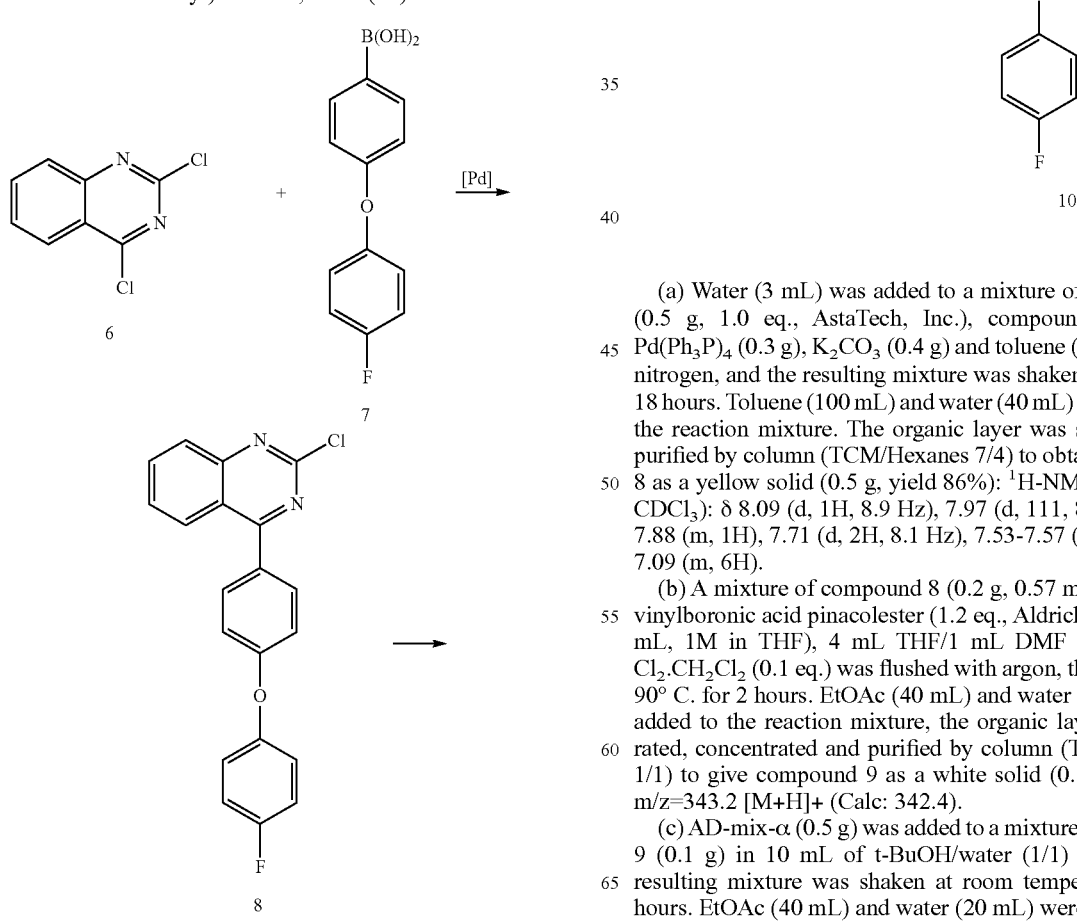

(a) Water (3 mL) was added to a mixture of compound 6 (0.5 g, 1.0 eq., AstaTech, Inc.), compound 7 (0.7 g), Pd(Ph₃P)₄ (0.3 g), K₂CO₃ (0.4 g) and toluene (10 mL) under nitrogen, and the resulting mixture was shaken at 95° C. for 18 hours. Toluene (100 mL) and water (40 mL) were added to the reaction mixture. The organic layer was separated and purified by column (TCM/Hexanes 7/4) to obtain compound 8 as a yellow solid (0.5 g, yield 86%): ¹H-NMR (400 MHz, CDCl₃): δ 8.09 (d, 1H, 8.9 Hz), 7.97 (d, 111, 8.6 Hz), 7.84-7.88 (m, 1H), 7.71 (d, 2H, 8.1 Hz), 7.53-7.57 (m, 1H), 7.01-7.09 (m, 6H).

(b) A mixture of compound 8 (0.2 g, 0.57 mmol, 1.0 eq.), vinylboronic acid pinacolester (1.2 eq., Aldrich), TBAF (1.0 mL, 1M in THF), 4 mL THF/1 mL DMF and Pd(dppf)Cl₂.CH₂Cl₂ (0.1 eq.) was flushed with argon, then, shaken at 90° C. for 2 hours. EtOAc (40 mL) and water (20 mL) were added to the reaction mixture, the organic layer was separated, concentrated and purified by column (TCM/Hexanes 1/1) to give compound 9 as a white solid (0.1 g): LC/MS: m/z=343.2 [M+H]+ (Calc: 342.4).

(c) AD-mix-α (0.5 g) was added to a mixture of compound 9 (0.1 g) in 10 mL of t-BuOH/water (1/1) at 0° C. The resulting mixture was shaken at room temperature for 24 hours. EtOAc (40 mL) and water (20 mL) were added to the reaction mixture, the organic layer was separated, concentrated and purified by column (silica gel, TCM/MeOH 10/0.5) to afford the title compound 10 as a white solid (80 mg, yield 70%): $^1$H-NMR (400 MHz, CDCl$_3$): δ 8.21 (d, 1H, 8.3 Hz), 8.13 (d, 1H, 8.3 Hz), 7.95-7.99 (m, 1H), 7.82 (d, 2H, 8.9 Hz), 7.64-7.68 (m, 1H), 7.12-7.18 (m, 6H), 5.08-5.11 (m, 1H), 4.8 (br, 2H, —OH), 4.12-4.18 (m, 2H); LC/MS: m/z=377.0 [M+H]+ (Calc: 376.4).

Example 3

Synthesis of Compounds 13a-13z

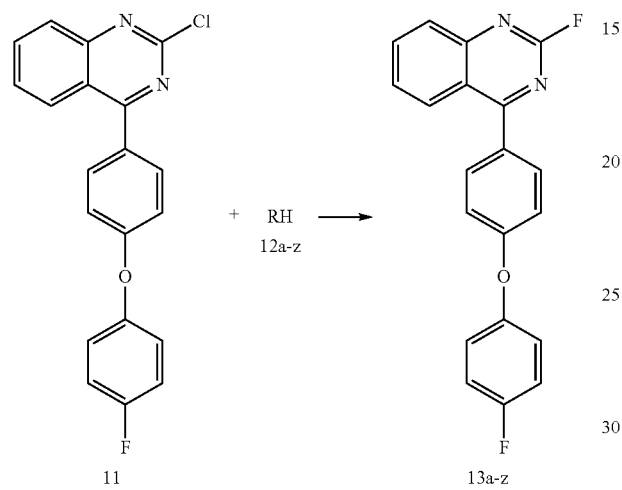

12a: H-SER-NH$_2$ HCL (ALDRICH); 12b: PIPERAZIN-2-ONE (Tyger Scientific Inc.); 12c: ETHANOLAMINE (ALDRICH); 12d: N,N-DIMETHYLETHYLENEDI-AMINE (ALDRICH); 12e: NH$_3$ (7N~ in MeOH, ALDRICH); 12f: L-PROLINE METHYL ESTER HYDROCHLORIDE (ALDRICH); 12 g: METHYLHYDRAZINE (ALDRICH); 12 h: N-ETHYLPIPERAZINE (ALDRICH); 12i: 4-HYDROXYPIPERIDINE (ALDRICH); 12j: N-(2-HYDROXYETHYL)PIPERAZINE (ALDRICH); 12k: 1-METHYLPIPERAZINE (ALDRICH); 12l: H-PRO-NH$_2$ L-PROLINAMIDE (ACROS); 12m: H-HYP-OME HCL (ALDRICH); 12n: METHYLAMINE (ALDRICH); 12o: N-(3-AMINOPROPYL)IMIDAZOLE (ALDRICH); 12p: N,N-DIMETHYL-1,3-PROPANEDIAMINE (ACROS); 12q: (R)-3-AMINO-1,2-PROPANEDIOL (TCI-US); 12r: (S)-3-AMINO-1,2-PROPANEDIOL (TCI-US); 12s: H-ASN—NH2 HCL (SIGMA); 12t: ENDO-9-METHYL-9-AZABICYCLO[3.3.1]-NONAN-3-AMINE (Trylead Chemical Technology Co., Ltd.); 12u: 2-AMINO-1,3-PROPANEDIOL (FLUKA); 12v: 1-(2-AMINOETHYL)-2-IMIDAZOLIDONE (OAKWOOD); 12w: 2-HYDROXYETHYLHYDRAZINE (ALDRICH); 12x: GLYCINAMIDE HYDROCHLORIDE (ALDRICH); 12y: ETHANOL (ALDRICH); 12z: 2-HYDROXYPYRIDINE (ALDRICH).

General procedure for the preparation of compounds 13a-z: A mixture of compound 11 (0.2 g, 1.0 eq.), RH (12a-z, 1.05 eq.), wherein R is NR$^5$R$^6$ or OR$^9$, K$_2$CO$_3$ (2 eq.) and TEA (2 eq.) in 3 mL of DMF was shaken at 100° C. for 24 hours. Water (5 mL) and EtOAc (30 mL) were added to the reaction mixture. The organic layer was separated, concentrated and purified by column (TCM/MeOH 10/0.2 to 10/5) to obtain compounds 13a-z in 20 to 90% yield.

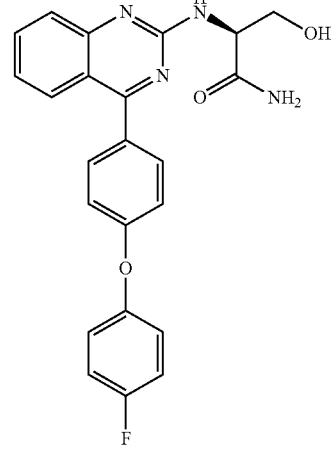

13a

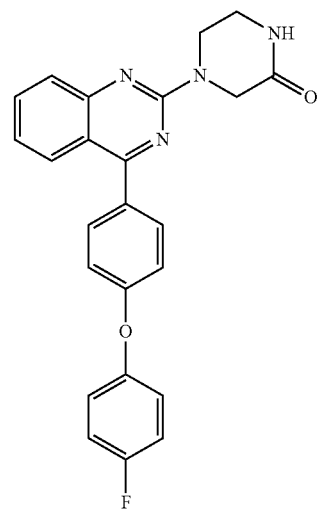

13b

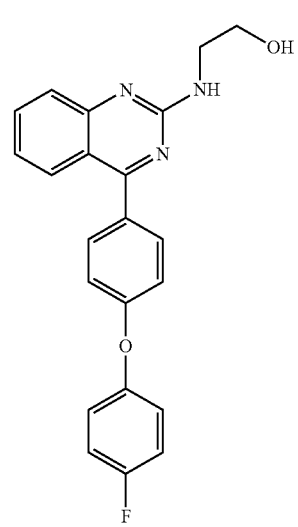

13c

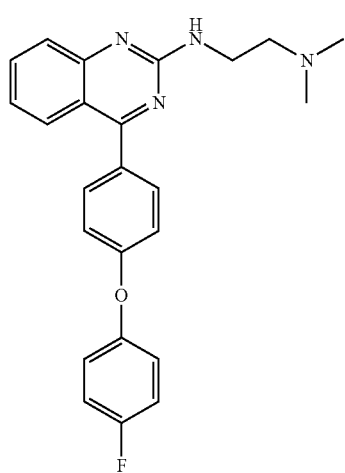
13d
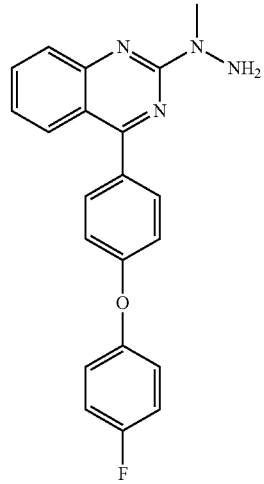
13g
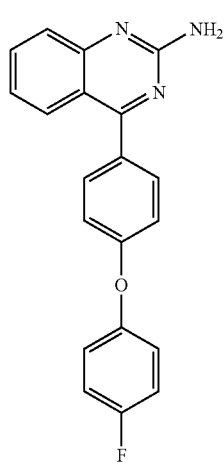
13e
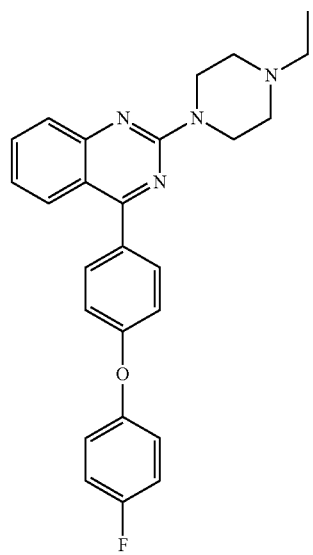
13h
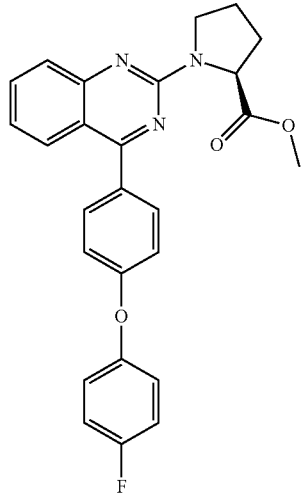
13f
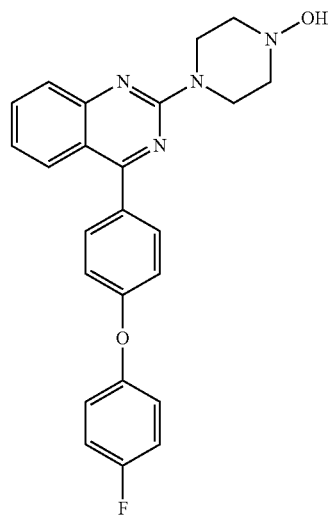
13i

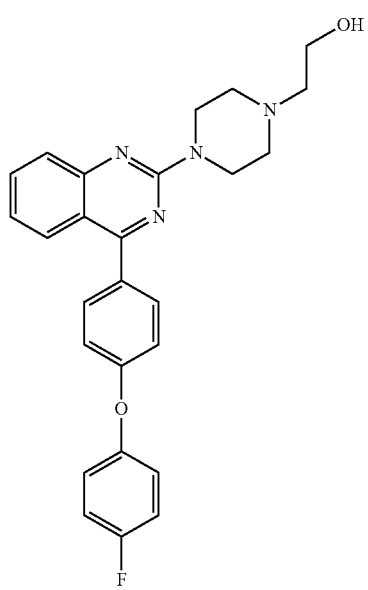
13j
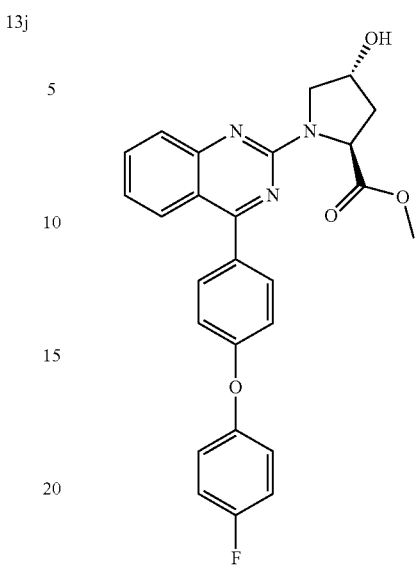
13k
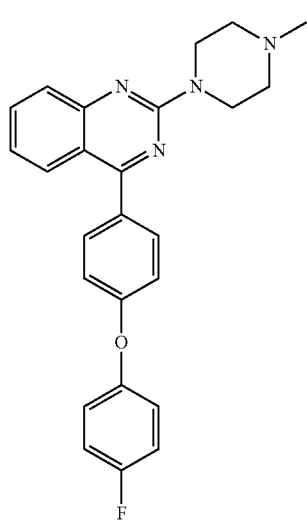
13m
13n
13l
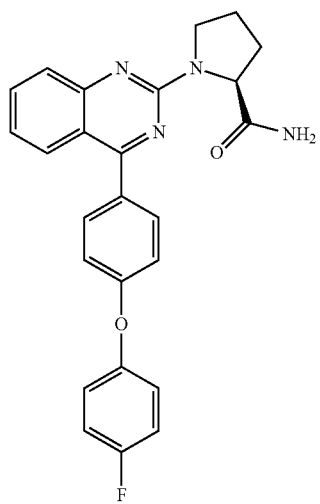
13o

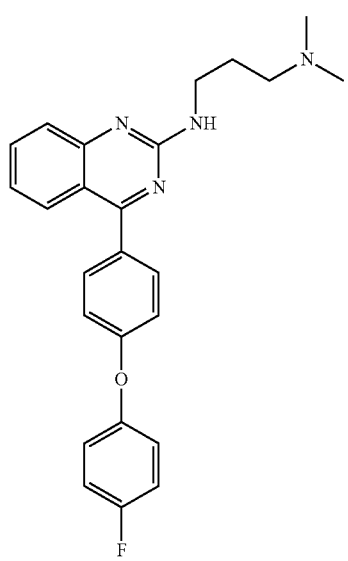
13p
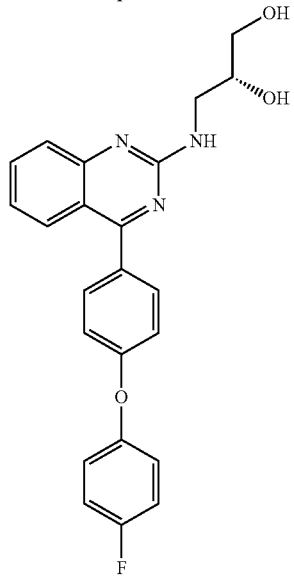
13q
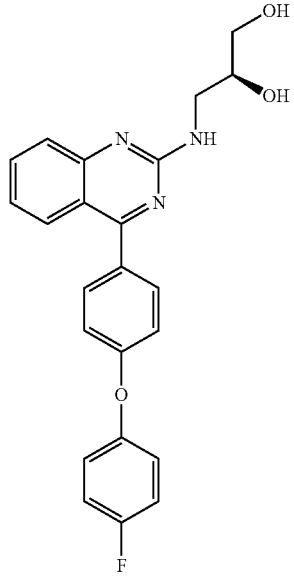
13r
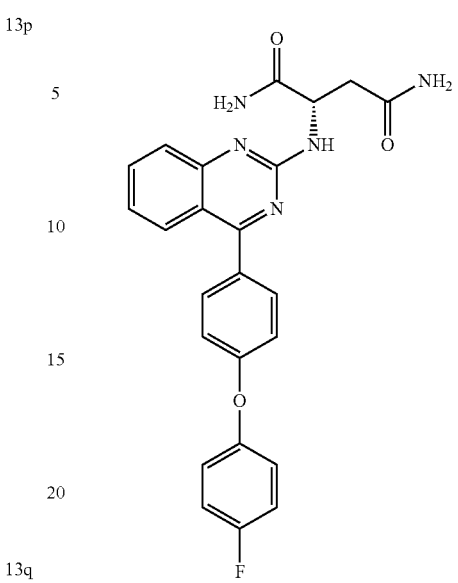
13s
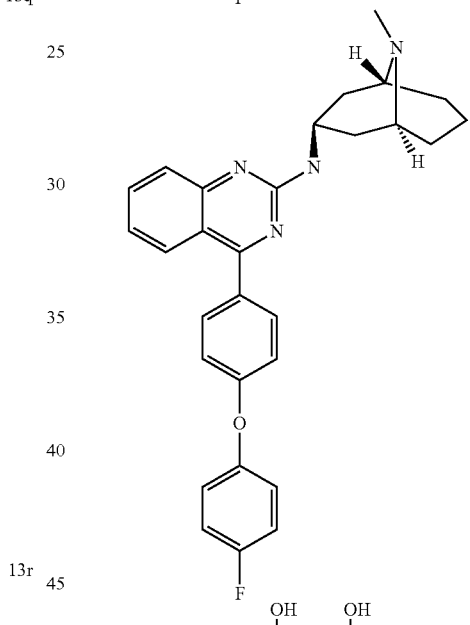
13t
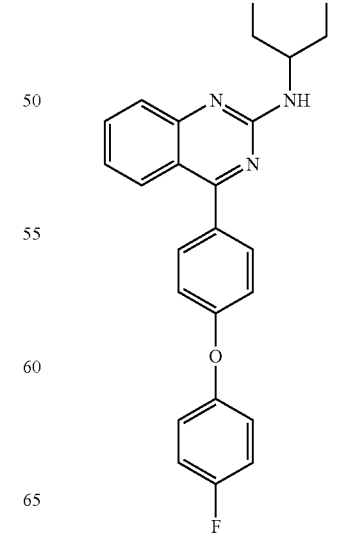
13u 73
-continued

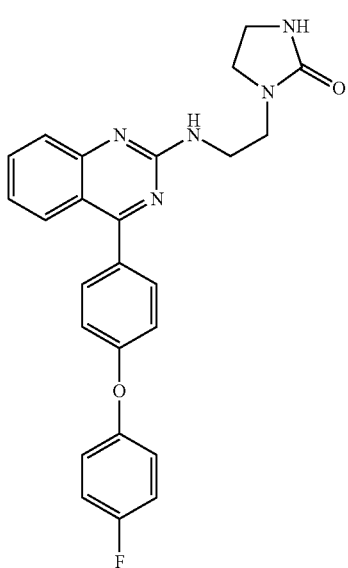
13v

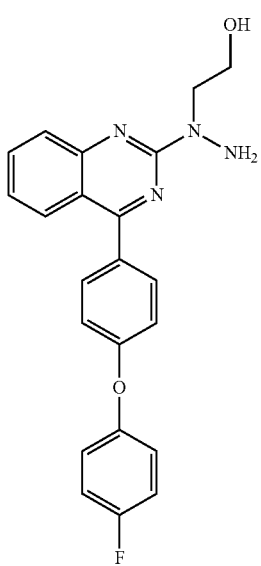
13w

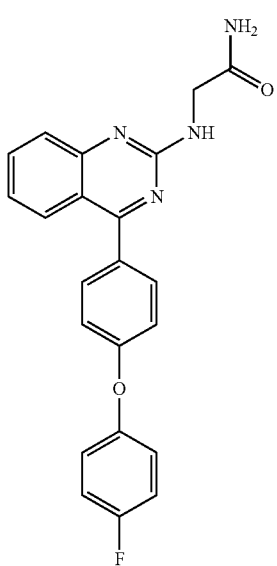
13x

74
-continued

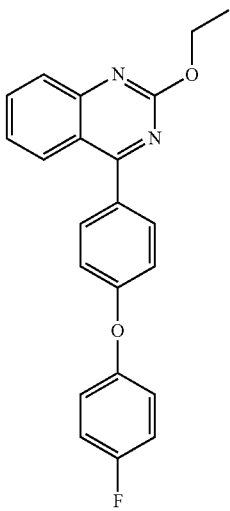
13y

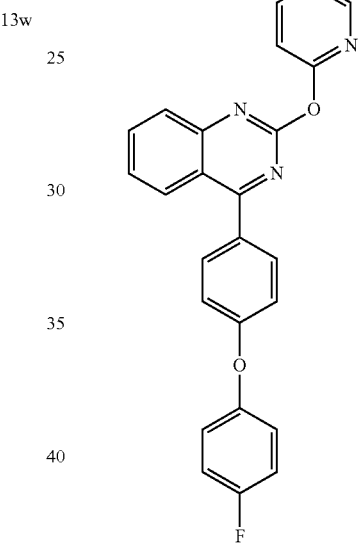
13z (S)-2-{4-[4-(4-Fluoro-phenoxy)-phenyl]-quinazolin-2-ylamino}-3-hydroxy-propionamide(13a, yellow solid): $^1$H-NMR (400 MHz, CD$_3$OD): δ 7.81 (d, 1H, 7.8 Hz), 7.61-7.66 (m, 3H), 7.54 (d, 1H, 8.5 Hz), 7.15-7.19 (m, 1H), 7.01-7.06 (m, 6H), 4.65 (t, 1H, 4.8 Hz), 3.93 (dd, 1H, 5.0 & 10.9 Hz), 3.85 (dd, 1H, 4.8 & 11.0 Hz); LC/MS: m/z=419.2 [M+H]+ (Calc: 418.4).

4-(4-(4-(4-Fluorophenoxy)phenyl)quinazolin-2-yl)piperazin-2-one (13b, yellow solid): $^1$H-NMR (400 MHz, CD$_3$OD): δ 7.87 (d, 1H, 8.1 Hz), 7.65-7.71 (m, 4H), 7.19-7.23 (m, 1H), 7.02-7.05 (m, 6H), 4.51 (s, 2H), 4.15 (t, 2H, 5.2 Hz), 3.44 (t, 2H, 5.1 Hz); LC/MS: m/z=415.1 [M+H]+ (Calc: 414.4).

2-((4-(4-(4-Fluorophenoxy)phenyl)quinazolin-2-yl)amino)ethanol (13c, yellow solid): $^1$H-NMR (400 MHz, CD$_3$OD): δ 7.81-8.1 (m, 5H), 7.58-7.64 (m, 1H), 7.18-7.24 (m, 6H), 3.76-3.94 (m, 4H); LC/MS: m/z=376.1 [M+H]+ (Calc: 375.4).

$N^1$-(4-(4-(4-Fluorophenoxy)phenyl)quinazolin-2-yl)-$N^2$,$N^2$-dimethylethane-1,2-diamine (13d, yellow solid): $^1$H-NMR (400 MHz, CD$_3$OD): δ 8.23 (d, 1H, 8.1 Hz), 8.12 (dd, 1H, 7.8 & 8.2 Hz), 7.98 (d, 2H, 8.3 Hz), 7.81-7.84 (m, 1H), 7.64-7.68 (m, 1H), 7.18-7.25 (m, 6H), 4.21 (t, 2H, 6.1 Hz), 3.54-3.58 (m, 2H); LC/MS: m/z=403.1 [M+H]+ (Calc: 402.5).

4-(4-(4-Fluorophenoxy)phenyl)quinazolin-2-amine (13e, yellow solid): ¹H-NMR (400 MHz, CD₃OD): δ 7.81-7.81 (m, 1H), 7.61-7.69 (m, 3H), 7.49-7.52 (m, 1H), 7.19-7.23 (m, 1H), 7.01-7.05 (m, 6H); LC/MS: m/z=332.0 [M+H]+ (Calc: 331.3).

(S)-Methyl 1-(4-(4-(4-fluorophenoxy)phenyl)quinazolin-2-yl)pyrrolidine-2-carboxylate (13f, white solid): ¹H-NMR (400 MHz, CDCl₃): δ 7.52-7.84 (m, 5H), 6.98-7.12 (m, 7H), 4.67-4.71 (m, 1H), 3.82-3.94 (m, 2H), 3.61 (s, 3H), 2.28-2.34 (m, 1H), 2.04-2.12 (m, 3H); LC/MS: m/z=444.1 [M+H]+ (Calc: 443.5).

4-(4-(4-Fluorophenoxy)phenyl)-2-(1-methylhydrazinyl)quinazoline (13 g, yellow solid): ¹H-NMR (400 MHz, DMSO-d₆): δ 7.78-7.83 (m, 3H), 7.71-7.74 (m, 1H), 7.58 (d, 1H, 8.3 Hz), 7.21-7.33 (m, 4H), 7.16 (d, 2H, 8.3 Hz), 5.07 (s, 2H, —NH2), 3.38 (s, 3H); LC/MS: m/z=361.1 [M+H]+ (Calc: 360.4).

2-(4-Ethylpiperazin-1-yl)-4-(4-(4-fluorophenoxy)phenyl)quinazoline (13 h, yellow solid): ¹H-NMR (400 MHz, CDCl₃): δ 7.88 (d, 1H, 8.1 Hz), 7.76 (d, 2H, 8.8 Hz), 7.66-7.68 (m, 2H), 7.17-7.21 (m, 1H), 7.11-7.15 (m, 6H), 4.09-4.15 (m, 4H), 2.55-2.71 (m, 6H), 1.22 (t, 3H, 7.2 Hz); LC/MS: m/z=429.1 [M+H]+ (Calc: 428.5).

1-(4-(4-(4-Fluorophenoxy)phenyl)quinazolin-2-yl)piperidin-4-ol (13i, yellow solid): ¹H-NMR (400 MHz, CDCl₃): δ 7.78 (d, 1H, 8.1 Hz), 7.67 (d, 2H, 8.8 Hz), 7.55-7.59 (m, 2H), 7.01-7.11 (m, 6H), 4.56-4.62 (m, 2H), 3.89-3.93 (m, 1H), 3.28-3.41 (m, 2H), 1.92-1.98 (m, 2H), 1.52-1.58 (m, 2H); LC/MS: m/z=416.2 [M+H]+ (Calc: 415.5).

2-(4-(4-(4-(4-Fluorophenoxy)phenyl)quinazolin-2-yl)piperazin-1-yl)ethanol (13j, yellow solid): ¹H-NMR (400 MHz, CDCl₃): δ 7.81 (d, 1H, 8.1 Hz), 7.67 (d, 21-1, 8.8 Hz), 7.58-7.61 (m, 2H), 7.10-7.14 (m, 1H), 7.01-7.05 (m, 6H), 4.06-4.12 (m, 4H), 3.69-3.73 (m, 2H), 2.66-2.76 (m, 6H); LC/MS: m/z=445.1 [M+H]+ (Calc: 444.5).

4-(4-(4-Fluorophenoxy)phenyl)-2-(4-methylpiperazin-1-yl)quinazoline (13k, yellow solid): ¹H-NMR (400 MHz, CDCl₃): δ 7.89 (d, 1H, 8.3 Hz), 7.76 (d, 2H, 8.8 Hz), 7.66-7.68 (m, 2H), 7.17-7.21 (m, 1H), 7.10-7.13 (m, 6H), 4.11-4.16 (m, 4H), 2.63-2.68 (m, 4H), 2.46 (s, 31-1); LC/MS: m/z=415.1 [M+H]+ (Calc: 414.5).

(S)-1-(4-(4-(4-Fluorophenoxy)phenyl)quinazolin-2-yl)pyrrolidine-2-carboxamide (13l, yellow solid): ¹H-NMR (400 MHz, CD₃OD): δ 7.93 (d, 1H, 8.3 Hz), 7.76 (d, 211, 8.8 Hz), 7.69-7.71 (m, 2H), 7.21-7.25 (m, 1H), 7.07-7.13 (m, 6H), 4.72-4.74 (m, 1H), 3.91-3.96 (m, 1H), 3.81-3.86 (m, 1H), 2.31-2.39 (m, 1H), 2.01-2.21 (m, 3H); LC/MS: m/z=429.1 [M+H]+ (Calc: 428.5).

(2S,4R)-Methyl 1-(4-(4-(4-fluorophenoxy)phenyl)quinazolin-2-yl)-4-hydroxypyrrolidine-2-carboxylate (13m, yellow solid): ¹H-NMR (400 MHz, CD₃OD): δ 7.84-7.89 (m, 1H), 7.62-7.69 (m, 4H), 7.16-7.21 (m, 1H), 7.0-7.06 (m, 6H), 4.79 (dd, 1H, 7.6 & 8.0 Hz), 4.54-4.58 (m, 1H), 3.86-3.94 (m, 2H), 3.58-3.64 (m, 3H), 2.32-2.38 (m, 1H), 2.11-2.19 (m, 1H); LC/MS: m/z=460.1 [M+H]+ (Calc: 459.5).

4-(4-(4-Fluorophenoxy)phenyl)-N-methylquinazolin-2-amine (13n, yellow solid): ¹H-NMR (400 MHz, DMSO-d₆): δ 7.6-7.7 (m, 4H), 7.49 (d, 1H, 8.5 Hz), 7.21-7.29 (m, 3H), 7.12-7.16 (m, 3H), 7.08 (d, 2H, 8.7 Hz), 2.85 (d, 3H, 4.8 Hz); LC/MS: m/z=346.1 [M+H]+ (Calc: 345.4).

N-(3-(1H-imidazol-1-yl)propyl)-4-(4-(4-fluorophenoxy)phenyl)quinazolin-2-amine (13o, yellow solid): ¹H-NMR (400 MHz, CD₃OD): δ 7.77 (d, 1H, 8.3 Hz), 7.69 (s, 1H), 7.6-7.64 (m, 3H), 7.56 (d, 1H, 8.1 Hz), 7.11-7.16 (m, 1H), 7.0-7.12 (m, 7H), 6.97 (s, 1H), 4.09 (t, 2H, 7.011z), 3.51 (t, 2H, 6.8 Hz), 2.1-2.16 (m, 2H); LC/MS: m/z=440.2 [M+H]+ (Calc: 439.5).

N¹-(4-(4-(4-Fluorophenoxy)phenyl)quinazolin-2-yl)-N³,N³-dimethylpropane-1,3-diamine (13p, yellow solid): ¹H-NMR (400 MHz, CDCl₃): δ 7.85 (d, 1H, 8.1 Hz), 7.66-7.73 (m, 4H), 7.18-7.22 (m, 1H), 6.98-7.14 (m, 6H), 5.75 (br, 1H), 3.68-3.74 (m, 2H), 2.74-2.8 (m, 2H), 2.51 (s, 6H), 2.04-2.09 (m, 2H); LC/MS: m/z=417.1 [M+H]+ (Calc: 416.5).

(R)-3-((4-(4-(4-Fluorophenoxy)phenyl)quinazolin-2-yl)amino)propane-1,2-diol (13q, yellow oil): ¹H-NMR (400 MHz, CDCl₃): δ 7.89 (d, 1H, 8.1 Hz), 7.66-7.74 (m, 4H), 7.24-7.27 (m, 1H), 7.09-7.14 (m, 6H), 5.75 (br, 1H), 3.89-3.94 (m, 1H), 3.63-3.77 (m, 4H); LC/MS: m/z=406.1 [M+H]+ (Calc: 405.4).

(S)-3-((4-(4-(4-Fluorophenoxy)phenyl)quinazolin-2-yl)amino)propane-1,2-diol (13r, yellow solid): ¹H-NMR (400 MHz, CDCl₃) δ: 7.89 (d, 1H, 8.1 Hz), 7.68-7.75 (m, 4H), 7.28-7.3 (m, 1H), 7.09-7.14 (m, 6H), 5.75 (br, 1H), 3.89-3.94 (m, 1H), 3.63-3.77 (m, 4H), 2.11 (br, 2H, —OH); LC/MS: m/z=406.1 [M+H]+ (Calc: 405.4).

(S)-2-(4-(4-(4-(4-Fluorophenoxy)phenyl)quinazolin-2-yl)amino)succinamide (13s, white solid): ¹H-NMR (400 MHz, CD₃OD): δ 7.94-7.98 (m, 1H), 7.74-7.79 (m, 3H), 7.66 (d, 1H, 8.5 Hz), 7.32-7.36 (m, 1H), 7.09-7.14 (m, 6H), 5.14-5.17 (m, 1H), 2.81-2.92 (m, 2H); LC/MS: m/z=446.2 [M+H]+ (Calc: 445.4).

4-(4-(4-Fluorophenoxy)phenyl)-N-01R,3S,5S)-9-methyl-9-azabicyclo[3.3.1]nonan-3-yl)quinazolin-2-amine (13t, yellow solid): ¹H-NMR (400 MHz, CDCl₃): δ 7.85 (d, 1H, 8.1 Hz), 7.67-7.74 (m, 4H), 7.17-7.21 (m, 1H), 7.09-7.14 (m, 6H), 5.16-5.18 (m, 1H), 4.65-4.67 (m, 1H), 3.28-3.25 (m, 2H), 2.67-2.82 (5H), 2.11-2.19 (m, 3H), 1.5-1.67 (m, 3H), 1.25-1.3 (m, 1H); LC/MS: m/z=469.1 [M+H]+ (Calc: 468.6).

2-((4-(4-(4-Fluorophenoxy)phenyl)quinazolin-2-yl)amino)propane-1,3-diol (13u, yellow solid): ¹H-NMR (400 MHz, DMSO-d₆): δ 7.61-7.66 (m, 4H), 7.4 (d, 1H, 8.3 Hz), 7.21-7.26 (m, 2H), 7.07-7.16 (m, 5H), 6.73-6.78 (m, 1H, NH), 4.57-4.62 (m, 2H, —OH), 4.02-4.07 (m, 1H), 3.49-3.53 (m, 4H); LC/MS: m/z=406.1 [M+H]+ (Calc: 405.4).

1-(2-((4-(4-(4-Fluorophenoxy)phenyl)quinazolin-2-yl)amino)ethyl)-imidazolidin-2-one (13v, yellow solid): ¹H-NMR (400 MHz, CD₃OD): δ 7.87 (d, 1H, 8.6 Hz), 7.61-7.72 (m, 4H), 7.09-7.14 (m, 6H), 3.73 (dd, 2H, 5.9 & 6.3 Hz), 3.6 (dd, 2H, 6.3 & 7.6 Hz), 3.48 (dd, 2H, 5.9 & 6.3 Hz), 3.35 (dd, 2H, 6.3 & 7.6 Hz); LC/MS: m/z=444.1 [M+H]+ (Calc: 443.5).

2-(1-(4-(4-(4-Fluorophenoxy)phenyl)quinazolin-2-yl)hydrazinyl)ethanol (13w, yellow solid): ¹H-NMR (400 MHz, DMSO-d₆): δ 7.71-7.76 (m, 3H), 7.64-7.68 (m, 1H), 7.53 (d, 1H, 8.3 Hz), 7.21-7.26 (m, 2H), 7.14-7.18 (m, 3H), 7.09 (d, 2H, 8.8 Hz), 4.98 (br, 2H, —NH₂), 4.58 (br, 1H, —OH), 3.85 (t, 2H, 7.3 Hz), 3.6-3.64 (m, 2H); LC/MS: m/z=391.1 [M+H]+ (Calc: 390.4).

2-((4-(4-(4-Fluorophenoxy)phenyl)quinazolin-2-yl)amino)acetamide (13x, white solid): ¹H-NMR (400 MHz, DMSO-d₆): δ 7.81 (d, 1H, 8.1 Hz), 7.7-7.76 (m, 3H), 7.55 (d, 1H, 8.6 Hz), 7.35-7.38 (m, 2H, —CONH₂), 7.15-7.31 (m, 7H), 7.03 (br, 1H, NH), 3.96 (d, 2H, 6.1 Hz); LC/MS: m/z=389.2 [M+H]+ (Calc: 388.4).

2-Ethoxy-4-(4-(4-fluorophenoxy)phenyl)quinazoline (13y, white solid): ¹H-NMR (400 MHz, CDCl₃): δ 7.97 (ddd, 1H, 0.6, 1.3 & 8.6 Hz), 7.78-7.81 (m, 1H), 7.69-7.74 (m, 2H), 7.32 (dt, 1H, 1.3 & 8.3 Hz), 6.99-7.04 (m, 6H), 4.53 (q, 2H, 7.2 Hz), 1.43 (t, 3H, 7.1 Hz); LC/MS: m/z=361.1 [M+11]+ (Calc: 360.4).

4-(4-(4-Fluorophenoxy)phenyl)-2-(pyridin-2-yloxy)quinazoline (13z, white solid): $^1$H-NMR (400 MHz, DMSO-$d_6$): δ 8.3 (d, 1H, 8.3 Hz), 8.14-8.17 (m, 2H), 7.85-7.96 (m, 4H), 7.57-7.62 (m, 1H), 7.2-7.34 (m, 6H), 6.54 (d, 1H, 8.9 Hz), 6.37 (dd, 1H, 1.3 & 6.9 Hz); LC/MS: m/z=410.0 [M+H]+ (Calc: 409.4).

Example 4

Representative compounds of the invention have been tested in the FLIPR$^{TETRA}$® or FLIPR® sodium dye assay with KCl assay and electrophysiology (EP) assay for sodium channel blocking activity, which are described in detail above. Representative values are presented in TABLE 2.

TABLE 2

Evaluation of the tested compounds as sodium channel (Na$_v$) blockers

| COMPOUND | FLIPR Na$_v$1.7 IC$_{50}$ (μM) ± SEM | EP Na$_v$1.7 K$_j$ (μM) | EP Na$_v$1.7 K$_r$ (μM) |
|---|---|---|---|
| N$^1$-(4-(4-(4-fluorophenoxy)phenyl)quinazolin-2-yl)-N$^2$,N$^2$-dimethylethane-1,2-diamine (13d) | 0.317 ± 0.026 | | |
| 2-((4-(4-(4-fluorophenoxy)phenyl)quinazolin-2-yl)amino)ethanol (13c) | 0.369 ± 0.046 | | |
| (S)-2-{4-[4-(4-fluorophenoxy)phenyl]quinazolin-2-ylamino}-3-hydroxy-propionamide (13a) | 0.836 ± 0.098 | 0.74 ± 0.05 | |
| 4-(4-(4-(4-fluorophenoxy)phenyl)quinazolin-2-yl)piperazin-2-one (13b) | 0.839 ± 0.066 | | |
| 4-(4-(4-fluorophenoxy)phenyl)quinazolin-2-amine (13e) | 0.426 ± 0.125 | | |
| (S)-methyl 1-(4-(4-(4-fluorophenoxy)phenyl)-quinazolin-2-yl)pyrrolidine-2-carboxylate (13f) | 0.642 ± 0.114 | 0.62 ± 0.19 | 23.90 ± 4.71 |
| 4-(4-(4-fluorophenoxy)phenyl)-2-(1-methylhydrazinyl)quinazoline (13g) | 0.309 ± 0.041 | | |
| 2-(4-ethylpiperazin-1-yl)-4-(4-(4-fluorophenoxy)phenyl)quinazoline (13h) | 0.236 ± 0.041 | | |
| 1-(4-(4-(4-fluorophenoxy)phenyl)quinazolin-2-yl)piperidin-4-ol (13i) | 0.428 ± 0.073 | | |
| 2-(4-(4-(4-fluorophenoxy)phenyl)quinazolin-2-yl)piperazin-1-yl)ethanol (13j) | 0.104 ± 0.010 | | |
| 4-(4-(4-fluorophenoxy)phenyl)-2-(4-methylpiperazin-1-yl)quinazoline (13k) | 0.418 ± 0.058 | 0.07 ± 0.02 | 2.09 ± 0.24 |
| (S)-1-(4-(4-(4-fluorophenoxy)phenyl)quinazolin-2-yl)pyrrolidine-2-carboxamide (13l) | 0.105 ± 0.011 | 0.19 ± 0.07 | |
| (2S,4R)-methyl 1-(4-(4-(4-fluorophenoxy)phenyl)quinazolin-2-yl)-4-hydroxypyrrolidine-2-carboxylate (13m) | 0.833 ± 0.162 | | |
| N-(3-(1H-imidazol-1-yl)propyl)-4-(4-(4-fluorophenoxy)phenyl)quinazolin-2-amine (13o) | 0.325 ± 0.084 | | |
| N$^1$-(4-(4-(4-fluorophenoxy)phenyl)quinazolin-2-yl)-N$^3$,N$^3$-dimethylpropane-1,3-diamine (13p) | 0.205 ± 0.020 | | |
| 4-(4-(4-fluorophenoxy)phenyl)-N-methylquinazolin-2-amine (13n) | 0.294 ± 0.048 | | |
| (R)-3-((4-(4-(4-fluorophenoxy)phenyl)quinazolin-2-yl)amino)propane-1,2-diol (13q) | 0.071 ± 0.011 | 0.22 ± 0.03 | |
| (S)-3-((4-(4-(4-fluorophenoxy)phenyl)quinazolin-2-yl)amino)propane-1,2-diol (13r) | 0.320 ± 0.079 | | |
| (S)-2-((4-(4-(4-fluorophenoxy)phenyl)quinazolin-2-yl)amino)succinamide (13s) | 0.313 ± 0.054 | | |
| 4-(4-(4-fluorophenoxy)phenyl)-N-((1R,3S,5S)-9-methyl-9-azabicyclo[3.3.1]nonan-3-yl)quinazolin-2-amine (13t) | 0.228 ± 0.053 | 0.02 ± 0.00 | |

TABLE 2-continued

Evaluation of the tested compounds as sodium channel (Na$_v$) blockers

| COMPOUND | FLIPR Na$_v$1.7 IC$_{50}$ (μM) ± SEM | EP Na$_v$1.7 K$_j$ (μM) | EP Na$_v$1.7 K$_r$ (μM) |
|---|---|---|---|
| 2-((4-(4-(4-fluorophenoxy)phenyl)quinazolin-2-yl)amino)propane-1,3-diol (13u) | 0.208 ± 0.111 | 0.64 ± 0.02 | 55.33 ± 14.77 |
| 1-(2-((4-(4-(4-fluorophenoxy)phenyl)quinazolin-2-yl)amino)ethyl)imidazolidin-2-one (13v) | 0.204 ± 0.071 | 0.46 ± 0.04 | 23.67 ± 2.91 |
| 2-(1-(4-(4-(4-fluorophenoxy)phenyl)quinazolin-2-yl)hydrazinyl)ethanol (13w) | 0.070 ± 0.017 | | |
| 2-((4-(4-(4-fluorophenoxy)phenyl)quinazolin-2-yl)amino)acetamide (13x) | >20 | | |
| 4-(4-phenoxyphenyl)quinazoline-2-carboxamide (5) | 0.097 ± 0.024 | 0.12 ± 0.01 | |
| ethyl 4-(4-phenoxyphenyl)quinazoline-2-carboxylate (3) | 1.570 ± 0.456 | | |
| 4-(4-phenoxyphenyl)quinazoline-2-carboxylic acid (4) | >20 | | |
| (S)-1-(4-(4-(4-fluorophenoxy)phenyl)quinazolin-2-yl)ethane-1,2-diol (10) | 0.849 ± 0.193 | | |
| 2-ethoxy-4-(4-(4-fluorophenoxy)phenyl)-quinazoline (13y) | 0.995 ± 0.164 | | |
| 4-(4-(4-fluorophenoxy)phenyl)-2-(pyridin-2-yloxy)quinazoline (13z) | 1.910 ± 0.431 | | |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having the Formula I:

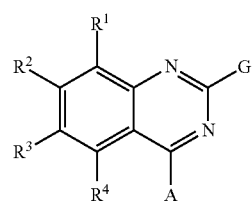

or a pharmaceutically acceptable salt thereof, wherein:
  R$^1$, R$^2$, R$^3$, and R$^4$ are each independently selected from the group consisting of hydrogen, alkyl, alkenyl, alkynyl, halogen, hydroxy, hydroxyalkyl, haloalkyl, cyano, amino, alkylamino, dialkylamino, alkoxy, aminocarbonyl, alkylaminocarbonyl, dialkylaminocarbonyl, alkylcarbonylamino, alkylcarbonyloxy, carboxy, alkoxycarbonyl, aminosulfonyl, alkylsulfonylamino, (alkylsulfonylamino)alkyl, ureido, (aminocarbonyl)alkylamino, and (carboxyalkyl)amino;

G is $G^1$, $G^2$, $G^3$, or $G^4$, wherein
$G^1$ is —$NR^5R^6$, wherein
$R^5$ is H, alkyl, or $NH_2$,
$R^6$ is
a) H,
b) alkyl,
c) hydroxyalkyl,
d) (aminocarbonyl)alkyl,
e) (aminocarbonyl)(hydroxy)alkyl;
f) aminoalkyl,
g) alkylaminoalkyl,
h) dialkylaminoalkyl,
i) cycloalkyl, unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;
j) (cycloalkyl)alkyl, wherein the cycloalkyl is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;
k) aryl, unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;
l) arylalkyl, wherein the aryl group is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;
m) heteroaryl, unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;
n) heteroarylalkyl, wherein the heteroaryl group is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;
o) heterocyclo, unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano; or
p) heterocycloalkyl, wherein the heterocyclo is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano; or
$R^5$ and $R^6$ together with the nitrogen atom to which they are attached form a 5- or 6-membered heterocyclic ring having carbon atoms and 1 or 2 nitrogen atoms, wherein the heterocyclic ring is unsubstituted or substituted with one or more substituents each independently selected from the group consisting of oxo, alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;
$G^2$ is

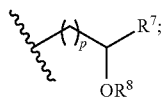

p is 0, 1 or 2;
$R^7$ is
a) —$(CH_2)_qOH$, wherein q is 0, 1, 2, 3, 4, or 5; or
b) selected from the group consisting of hydrogen, amino, alkylamino, dialkylamino, and alkoxy; and
$R^8$ is hydrogen or a bond;
$G^3$ is a 5- or 6-membered heteroaryl containing at least one nitrogen atom, wherein the heteroaryl is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano; and
$G^4$ is —$OR^9$, wherein $R^9$ is alkyl, alkenyl, alkynyl, hydroxyalkyl, aminoalkyl, alkylaminoalkyl, dialkylaminoalkyl, aminocarbonylalkyl, carboxyalkyl, alkoxycarbonylalkyl, arylalkyl, heteroarylalkyl, aryl or heteroaryl, wherein said aryl and heteroaryl are unsubstituted or substituted with one or more substituents selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano;
A is

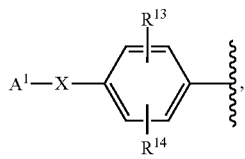

wherein
$A^1$ is aryl or heteroaryl, any of which is optionally substituted;
X is —O—, —S—, —SO—, —$SO_2$—, —$CH_2$—, or —NH—; and
$R^{13}$ and $R^{14}$ are each independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl;
with the proviso that when G is $G^1$, where $R^5$ is hydrogen or alkyl and $R^6$ is hydrogen, alkyl or cycloalkyl, and X is —O—, then no two of $R^1$, $R^2$, $R^3$ and $R^4$ are alkoxy at the same time.

2. The compound of claim 1, or a pharmaceutically acceptable salt thereof, wherein A is A' having the structure:

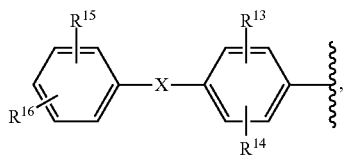

wherein X is —O—, —S—, —SO—, —SO$_2$—, —CH$_2$—, or —NH—, and R$^{13}$, R$^{14}$, R$^{15}$, and R$^{16}$ are each independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl.

3. The compound of claim 1, wherein X is —O—.

4. The compound of claim 1, or a pharmaceutically acceptable salt thereof, wherein A is A″ having the structure:

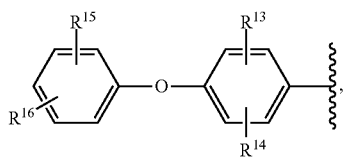

wherein
R$^{13}$, R$^{14}$, R$^{15}$ and R$^{16}$ are each independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl.

5. The compound of claim 1, wherein A is A″, and R$^1$, R$^2$, R$^3$ and R$^4$ are each hydrogen, having the Formula II:

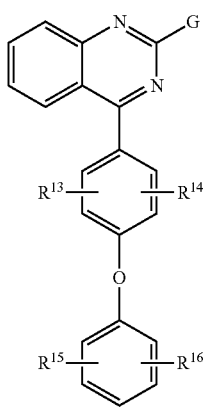

II or a pharmaceutically acceptable salt thereof, wherein G is as defined in claim 1, and R$^{13}$, R$^{14}$, R$^{15}$ and R$^{16}$ are each independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl.

6. The compound of claim 1, or a pharmaceutically acceptable salt thereof, wherein G is G$^1$.

7. The compound of claim 1, or a pharmaceutically acceptable salt thereof, wherein R$^5$ in G$^1$ is H and R$^6$ is as defined in claim 1.

8. The compound of claim 1, or a pharmaceutically acceptable salt thereof, wherein R$^5$ in G$^1$ is alkyl and R$^6$ is as defined in claim 1.

9. The compound of claim 1, or a pharmaceutically acceptable salt thereof, wherein R$^5$ in G$^1$ is NH$_2$ and R$^6$ is as defined in claim 1.

10. The compound of claim 1, or a pharmaceutically acceptable salt thereof, wherein R$^6$ in G$^1$ is hydrogen and R$^5$ is as defined in claim 1.

11. The compound of claim 1, or a pharmaceutically acceptable salt thereof, wherein R$^6$ in G$^1$ is alkyl and R$^5$ is as defined in claim 1.

12. The compound of claim 1, or a pharmaceutically acceptable salt thereof, wherein R$^6$ in G$^1$ is hydroxyalkyl and R$^5$ is as defined in claim 1.

13. The compound of claim 1, or a pharmaceutically acceptable salt thereof, wherein R$^6$ in G$^1$ is (aminocarbonyl)alkyl and R$^5$ is as defined in claim 1.

14. The compound of claim 1, or a pharmaceutically acceptable salt thereof, wherein R$^6$ in G$^1$ is (aminocarbonyl)(hydroxy)alkyl and R$^5$ is as defined in claim 1.

15. The compound of claim 1, or a pharmaceutically acceptable salt thereof, wherein R$^6$ in G$^1$ is aminoalkyl and R$^5$ is as defined in claim 1.

16. The compound of claim 1, or a pharmaceutically acceptable salt thereof, wherein R$^6$ in G$^1$ is alkylaminoalkyl and R$^5$ is as defined in claim 1.

17. The compound of claim 1, or a pharmaceutically acceptable salt thereof, wherein R$^6$ in G$^1$ is dialkylaminoalkyl and R$^5$ is as defined in claim 1.

18. The compound of claim 1, or a pharmaceutically acceptable salt thereof, wherein R$^6$ is cycloalkyl, unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano, and R$^5$ is as defined in claim 1.

19. The compound of claim 1, or a pharmaceutically acceptable salt thereof, wherein R$^6$ is (cycloalkyl)alkyl, wherein the cycloalkyl is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano, and R$^5$ is as defined in claim 1.

20. The compound of claim 1, or a pharmaceutically acceptable salt thereof, wherein R$^6$ is aryl, unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano, and R$^5$ is as defined in claim 1.

21. The compound of claim 1, or a pharmaceutically acceptable salt thereof, wherein R$^6$ is arylalkyl, wherein the aryl group is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano, and R$^5$ is as defined in claim 1.

22. The compound of claim 1, or a pharmaceutically acceptable salt thereof, wherein $R^6$ is heteroaryl, unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano, and $R^5$ is as defined in claim 1.

23. The compound of claim 1, or a pharmaceutically acceptable salt thereof, wherein $R^6$ is heteroarylalkyl, wherein the heteroaryl group is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano, and $R^5$ is as defined in claim 1.

24. The compound of claim 1, or a pharmaceutically acceptable salt thereof, wherein $R^6$ is heterocyclo, unsubstituted or substituted with one or more substituents each independently selected from the group consisting of oxo, alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano, and $R^5$ is as defined in claim 1.

25. The compound of claim 1, or a pharmaceutically acceptable salt thereof, wherein $G^1$ is selected from the group consisting of

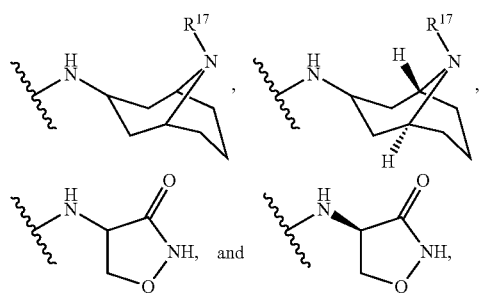

wherein $R^{17}$ is hydrogen or $C_{1-4}$ alkyl.

26. The compound of claim 1, or a pharmaceutically acceptable salt thereof, wherein $R^6$ is heterocycloalkyl, wherein the heterocyclo group is unsubstituted or substituted with one or more substituents each independently selected from the group consisting of oxo, alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano, and $R^5$ is as defined in claim 1.

27. The compound of claim 1, or a pharmaceutically acceptable salt thereof, wherein $R^5$ and $R^6$ together with the nitrogen atom to which they are attached form a 5- or 6-membered heterocyclic ring having carbon atoms and 1 or 2 nitrogen atoms, wherein the heterocyclic ring is unsubstituted or substituted with one or more substituents each independently selected from the group consisting of oxo, alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano.

28. The compound of claim 1, or a pharmaceutically acceptable salt thereof, wherein G is $G^2$

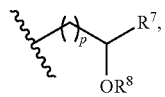

wherein
p is 0, 1 or 2;
$R^7$ is
a) —$(CH_2)_qOH$, wherein q is 0, 1, 2, 3, 4 or 5; or
b) selected from the group consisting of hydrogen, amino, alkylamino, dialkylamino, and alkoxy; and
$R^8$ is hydrogen or a bond.

29. The compound of claim 28 or a pharmaceutically acceptable salt thereof, wherein p is 0.

30. The compound of claim 28 or a pharmaceutically acceptable salt thereof, wherein p is 1.

31. The compound of claim 28, or a pharmaceutically acceptable salt thereof, wherein $R^8$ is hydrogen.

32. The compound of claim 28, or a pharmaceutically acceptable salt thereof, wherein $R^8$ is a bond.

33. The compound of claim 28, or a pharmaceutically acceptable salt thereof, wherein $R^7$ is hydrogen, amino or alkoxy.

34. The compound of claim 28, or a pharmaceutically acceptable salt thereof, wherein $R^7$ is —$(CH_2)_qOH$ and q is 0, 1, 2, or 3.

35. The compound of claim 1, or a pharmaceutically acceptable salt thereof, wherein G is $G^3$, which is a 5- or 6-membered heteroaryl containing at least one nitrogen atom, wherein the heteroaryl is unsubstituted or substituted with one or more substituents each independently selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano.

36. The compound of claim 1, or a pharmaceutically acceptable salt thereof, wherein $G^4$ is —$OR^9$, wherein $R^9$ is alkyl, aryl or heteroaryl, wherein said aryl and heteroaryl are unsubstituted or substituted with one or more substituents selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano.

37. The compound of claim 36, or a pharmaceutically acceptable salt thereof, wherein $R^9$ is alkyl which is unsubstituted or substituted with one or more substituents selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano.

38. The compound of claim 36, or a pharmaceutically acceptable salt thereof, wherein $R^9$ is heteroaryl which is unsubstituted or substituted with one or more substituents selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano.

39. The compound of claim 36, or a pharmaceutically acceptable salt thereof, wherein $R^9$ is aryl which is unsubstituted or substituted with one or more substituents selected from the group consisting of alkyl, alkoxy, halogen, haloalkyl, haloalkoxy, hydroxy, hydroxyalkyl, amino, aminoalkyl, alkylaminoalkyl, dialkylaminoalkyl, aminocarbonyl, carboxy, alkoxycarbonyl, and cyano.

40. The compound of claim 1, having the Formula III:

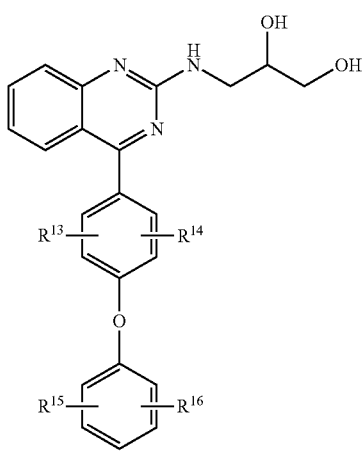

III or a pharmaceutically acceptable salt thereof, wherein $R^{13}$, $R^{14}$, $R^{15}$ and $R^{16}$ are each independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl.

41. The compound of claim 1, having the Formula IV:

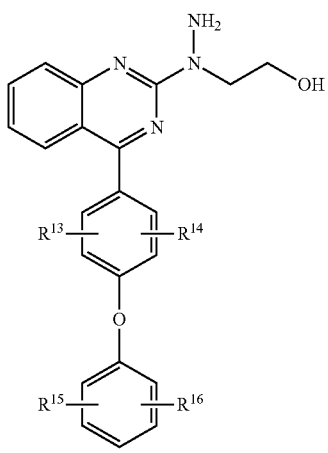

IV or a pharmaceutically acceptable salt thereof, wherein $R^{13}$, $R^{14}$, $R^{15}$ and $R^{16}$ are each independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl.

42. The compound of claim 1, having the Formula V:

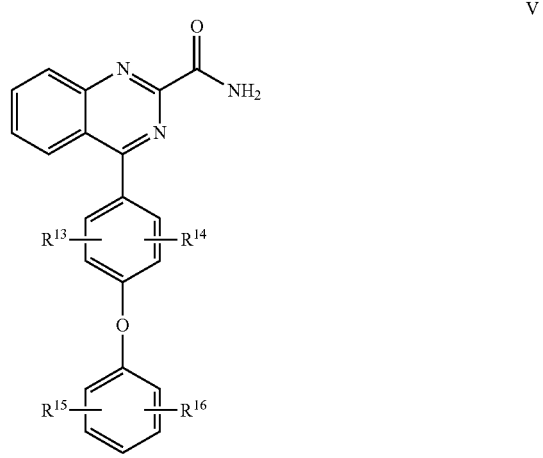

V or a pharmaceutically acceptable salt thereof, wherein $R^{13}$, $R^{14}$, $R^{15}$ and $R^{16}$ are each independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, mercaptoalkyl, alkoxy, carboxy, and aminocarbonyl.

43. The compound of claim 1, wherein said compound is
$N^1$-(4-(4-(4-fluorophenoxy)phenyl)quinazolin-2-yl)-$N^2$,$N^2$-dimethylethane-1,2-diamine;
2-((4-(4-(4-fluorophenoxy)phenyl)quinazolin-2-yl)amino)ethanol;
(S)-2-{4-[4-(4-fluorophenoxy)phenyl]quinazolin-2-ylamino}-3-hydroxy-propionamide;
4-(4-(4-(4-fluorophenoxy)phenyl)quinazolin-2-yl)piperazin-2-one;
4-(4-(4-fluorophenoxy)phenyl)quinazolin-2-amine;
(S)-methyl 1-(4-(4-(4-fluorophenoxy)phenyl)-quinazolin-2-yl)-pyrrolidine-2-carboxylate;
4-(4-(4-fluorophenoxy)phenyl)-2-(1-methylhydrazinyl)quinazoline;
2-(4-ethylpiperazin-1-yl)-4-(4-(4-fluorophenoxy)phenyl)quinazoline;
1-(4-(4-(4-fluorophenoxy)phenyl)quinazolin-2-yl)piperidin-4-ol;
2-(4-(4-(4-fluorophenoxy)phenyl)quinazolin-2-yl)piperazin-1-yl)ethanol;
4-(4-(4-fluorophenoxy)phenyl)-2-(4-methylpiperazin-1-yl)quinazoline;
(S)-1-(4-(4-(4-fluorophenoxy)phenyl)quinazolin-2-yl)pyrrolidine-2-carboxamide;
(2S,4R)-methyl 1-(4-(4-(4-fluorophenoxy)phenyl)quinazolin-2-yl)-4-hydroxy-pyrrolidine-2-carboxylate;
N-(3-(1H-imidazol-1-yl)propyl)-4-(4-(4-fluorophenoxy)phenyl)quinazolin-2-amine;
$N^1$-(4-(4-(4-fluorophenoxy)phenyl)quinazolin-2-yl)-$N^3$,$N^3$-dimethylpropane-1,3-diamine;
4-(4-(4-fluorophenoxy)phenyl)-N-methylquinazolin-2-amine;
(R)-3-((4-(4-(4-fluorophenoxy)phenyl)quinazolin-2-yl)amino)propane-1,2-diol;
(S)-3-((4-(4-(4-fluorophenoxy)phenyl)quinazolin-2-yl)amino)propane-1,2-diol;
(S)-2-((4-(4-(4-fluorophenoxy)phenyl)quinazolin-2-yl)amino)succinamide;

4-(4-(4-fluorophenoxy)phenyl)-N-((1R,3S,5S)-9-methyl-9-azabicyclo[3.3.1]nonan-3-yl)quinazolin-2-amine;
2-((4-(4-(4-fluorophenoxy)phenyl)quinazolin-2-yl)amino)propane-1,3-diol;
1-(2-((4-(4-(4-fluorophenoxy)phenyl)quinazolin-2-yl)amino)ethyl)imidazolidin-2-one;
2-(1-(4-(4-(4-fluorophenoxy)phenyl)quinazolin-2-yl)hydrazinyl)ethanol;
2-((4-(4-(4-fluorophenoxy)phenyl)quinazolin-2-yl)amino)acetamide;
4-(4-phenoxyphenyl)quinazoline-2-carboxamide;
ethyl 4-(4-phenoxyphenyl)quinazoline-2-carboxylate;
4-(4-phenoxyphenyl)quinazoline-2-carboxylic acid;
(S)-1-(4-(4-(4-fluorophenoxy)phenyl)quinazolin-2-yl)ethane-1,2-diol;
2-ethoxy-4-(4-(4-fluorophenoxy)phenyl)-quinazoline;
4-(4-(4-fluorophenoxy)phenyl)-2-(pyridin-2-yloxy)quinazoline;

or a pharmaceutically acceptable salt thereof.

44. A compound having the Formula I as claimed in claim 1, wherein the compound is $^3$H, $^{11}$C, or $^{14}$C radiolabeled, or a pharmaceutically acceptable salt thereof.

45. A pharmaceutical composition, comprising the compound of claim 1, or a pharmaceutically acceptable salt thereof, and a pharmaceutically acceptable carrier.

46. A method for treating pain in a mammal, comprising administering an effective amount of a compound as claimed in claim 1, or a pharmaceutically acceptable salt thereof, to a mammal in need of such treatment.

47. The method of claim 46, wherein the method is for preemptive or palliative treatment of pain.

48. The method of claim 46, wherein said pain is selected from the group consisting of chronic pain, inflammatory pain, neuropathic pain, postsurgical pain, acute pain, and surgical pain.

49. A method of screening a candidate compound for the ability to bind to a binding site on a protein using a radiolabeled compound of claim 44, comprising i) introducing a fixed concentration of the radiolabeled compound to an in vitro preparation comprising a soluble or membrane-associated sodium channel, subunit or fragment under conditions that permit the radiolabeled compound to bind to the channel, subunit of fragment, respectively, to form a conjugate ii) titrating the mixture with a candidate compound; and iii) determining the ability of the candidate compound to displace the radiolabeled compound from said channel, subunit or fragment.

50. A method of preparing a pharmaceutical composition, comprising admixing a therapeutically effective amount of a compound of claim 1, or a pharmaceutically acceptable salt thereof, with a pharmaceutically acceptable carrier.

* * * * *